US006841667B2

(12) United States Patent
Jacobsen et al.

(10) Patent No.: US 6,841,667 B2
(45) Date of Patent: Jan. 11, 2005

(54) NUCLEOPHILIC KINETIC RESOLUTION OF CYCLIC SUBSTRATES USING SILYL AZIDES

(75) Inventors: Eric N. Jacobsen, Boston, MA (US); Makoto Tokunaga, Saitama (JP); Jay F. Larrow, Irvine, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/615,501

(22) Filed: Jul. 7, 2003

(65) Prior Publication Data

US 2004/0044233 A1 Mar. 4, 2004

Related U.S. Application Data

(63) Continuation of application No. 10/206,143, filed on Jul. 26, 2002, which is a continuation of application No. 09/899,516, filed on Jul. 5, 2001, now Pat. No. 6,448,414, which is a continuation of application No. 09/134,393, filed on Aug. 14, 1998, now Pat. No. 6,262,278, which is a continuation-in-part of application No. 08/622,549, filed on Mar. 25, 1996, now Pat. No. 5,929,232, which is a continuation-in-part of application No. 08/403,374, filed on Mar. 14, 1995, now Pat. No. 5,665,890.

(51) Int. Cl.$^7$ .......................................... C07D 203/06
(52) U.S. Cl. .................. 540/604; 544/264; 548/965; 548/969; 549/230; 549/296; 549/513; 549/518; 562/64
(58) Field of Search .................. 540/604; 544/264; 548/965, 969; 549/230, 296, 513, 518; 562/64; 502/158

(56) References Cited

U.S. PATENT DOCUMENTS

| | | | |
|---|---|---|---|
| 3,868,401 A | 2/1975 | Aratani et al. ............... 260/468 |
| 4,151,195 A | 4/1979 | Warnant et al. ............... 260/465 |
| 4,471,130 A | 9/1984 | Katsuki et al. ............... 549/523 |
| 4,538,003 A | 8/1985 | Tam ............................ 568/656 |
| 4,565,845 A | 1/1986 | Inoue et al. .................. 525/25 |
| 4,594,439 A | 6/1986 | Katsuki et al. ............... 549/523 |
| 4,663,467 A | 5/1987 | Kruper, Jr. et al. ........... 549/229 |
| 4,822,899 A | 4/1989 | Groves et al. ............... 549/533 |
| 4,870,208 A | 9/1989 | Chan et al. .................. 562/579 |
| 4,885,376 A | 12/1989 | Verkade ........................ 556/18 |
| 4,965,364 A | 10/1990 | Marko et al. ................ 546/134 |
| 5,126,494 A | 6/1992 | Gilheany et al. ............. 568/807 |
| 5,250,731 A | 10/1993 | Burk ........................... 564/150 |
| 5,254,704 A | 10/1993 | Takano et al. ............... 549/552 |
| 5,258,553 A | 11/1993 | Burk ............................ 568/12 |
| 5,296,595 A | 3/1994 | Doyle .......................... 540/200 |
| 5,310,956 A | 5/1994 | Takano et al. ............... 549/529 |
| 5,312,957 A | 5/1994 | Casalnuovo et al. ......... 558/410 |
| 5,321,143 A | 6/1994 | Sharpless et al. ............. 549/34 |
| 5,352,814 A | 10/1994 | Katsuki et al. ............... 556/50 |
| 5,360,938 A | 11/1994 | Babin et al. .................. 568/449 |
| 5,665,890 A | 9/1997 | Jacobsen et al. ............. 549/230 |
| 5,929,232 A | 7/1999 | Jacobsen et al. ............. 540/145 |
| 6,262,278 B1 | 7/2001 | Jacobsen et al. ............. 549/230 |
| 6,448,414 B1 | 9/2002 | Jacobsen et al. ............. 549/230 |

FOREIGN PATENT DOCUMENTS

| | | |
|---|---|---|
| EP | 0 342 615 | 11/1989 |
| HU | P9500057 | 5/1997 |
| WO | WO 91/14694 | 10/1991 |
| WO | 2 244 055 A | 11/1991 |
| WO | WO 93/03838 | 3/1993 |
| WO | WO 96/28402 | 9/1996 |

OTHER PUBLICATIONS

Adam, W. et al., "Tridentate β–Hydroperoxy Alcohols As Novel Oxygen Donors For The Titanium–Catalyzed Epoxydation of $v_1\delta$–Unsaturated α, β–Diols: A Direct Diastereoselective Synthesis Of Opoxiy Diols", Angew Chem. Int Ed, Engl 33(10):1170–1108 (1994).

Adolfsson, H. et al. "Chiral Lewis Acid Catalyzed Asymmetric Nucleophilic Ring Opening of Cyclohexen Oxide", Tetrahetron(Asymmetry) 6 (8):2023–2031 (1995).

Agarwal, D. et al., "Olefin Expoxidation Using Iron (III) Schiff Base Complexes As Catalyst", Indian Journal of Chemistry 31A : 785–787 (1992).

Barili, P. et al., "Regio– and Stereochemistry Of The Acid Catalyzed And Of a Highly Enantioselective Enzymatic Hydrolysis of Some Epoxyterahydrofurans", Tetrahedron 49(28):6263–6276 (1993).

Brandes, B. and E. Jocobesn, "Highly Enantioselective, Catalytic Epoxidation Of Trisubstituted Olefins", J. of Am. Chem. Soc. 59: 4378–4380 (1994).

Chang, S. et al., "Effect of Chiral Quaternary Ammonium Salts On (Salen) Mn–Catalyzed Epoxidation Of Cis–Olefins. A Highly Enantioselective, Catalytic Route to Trans–Epoxides" J. Am. Chem. Soc. 116 (15):6937–6938 (1994).

Chen, X. et al., "Microbiological Transformations 27. The First Examples for Preparative–Scale Enantioselective or Diastereoselective Epoxide Hydrolyses Using Microorganisms. An Unequivocal Access to All Four Bisabolol Stereoisomers", J. of Am. Chem. Soc. 58(20):5528–5532 (1993).

Collman J. et al., "Regioselective and enantioselective Epoxidation Catalyzed by Metalloporphyrins", Science, 261:1404–1411 (1993).

Collman, J. et al., "Enantioselective Epoxidation Of unfunctionalized Olefins Catalyzed By Threitol–Strapped Manganese Porphyrins", J. of Am. Chem. Soc. 115:3834–3835 (1993).

(List continued on next page.)

*Primary Examiner*—Fiona T. Powers
(74) *Attorney, Agent, or Firm*—Dana M. Gordon; Foley Hoag LLP

(57) ABSTRACT

The present invention relates to a process for stereoselective or regioselective chemical synthesis which generally comprises reacting a nucleophile and a chiral or prochiral cyclic substrate in the presence of a non-racemic, chiral catalyst to produce a stereoisomerically- and/or regioisomerically-enriched product. The present invention also relates to hydrolytic kinetic resolutions of racemic and diastereomeric mixtures of epoxides.

35 Claims, 5 Drawing Sheets-

OTHER PUBLICATIONS

Corey, E. and F. Hannon, "Chiral Catalysts For the Enantioselective Addition Of Organometallic Reagents to Aldehydes", Tetrahedron Letters 28(44):5233–5236 (1987).

Desimoni, G. et al., Copper(II) In Organic Synthesis X(*). The Importance of Steric Hindrance In The Design of Chiral Tridentate Ligand Copper (II) Catalysts For Enantioselective Michael Reactions(**) Gazzetta Chimica Italiana 122: 268–273 (1992).

Emziane, M. et al., "Asymmetric Ring–Opening of Cyclohexene Oxide With Trimethylsilyl Azide In The Presence of Titanium Isopropoxide/Chiral Ligand", J. of Organometallic Chemistry 346: C7–C10(1988).

Groves, J. and R. Neumann, "Regioselective Oxidation Catalysis In Synthetic Phospholipid Vesicles. Membrane–Spanning Steroidal Metalloporphyrins" J. Am. Chem. Soc. 111:2900–2909 (1989).

Groves, G. and R. Neumann, "Membrane–Spanning Steroidal Metalloporphyrins as Site–Selective Catalysts in Synthetic Vesicles" J. Am. Chem. Soc. 109:5045–5047 (1987).

Hayashi, M. et al., "Novel Asymmetric Ring–Opening Reactions of Symmetrical N–Acylaziridines with Arenethiols Catalysed by Chiral Dialkyl Tartrate–Diathylzinc Complexes", J. of Chem. Soc. Chem. Commun. No. 23: 2699–2700 (1994).

Hayashi, M. et al., "Asymmetric Ring–Opening of Symmetrical Epoxides With Trimethylsilyl Azide Using Chiral Titanium Complexes", Sunlett. No. 11:774–776 (1991).

Jameson, D. "2,6 Bis (N–pyrazolyl) Pyridines; The Convenient Synthesis of a Family of Planar Tridentate N3 Ligands that are Terpyridine Analogues", J. of Organ. Chem. 55: 4992–4994 (1990).

Jacobsen, E. et al., "Highly Enantioselective Epoxidation Catalysts Derived from 1,2–Diaminocyclohexane", J. Am. Chem. Soc. 113:7063–7064 (1991).

Knebel, W. and R. Angelici, "Kinetic and Equilibrium Studies of Bi– and Tridentate Chelate Ring –Opening Reactions of Metal Carbonyl Complexes", Inorganic Chemistry 13(3): 632–637 (1974).

Kruper, W. and Dellar, D. "Catalytic Formation of Cyclic Carbonates From Epoxides and Co2 With Chromium Metalloporphirinates", J. Org. Chem. 60:725–727 (1995).

Larrow, J. and E. Jacobsen, "Kinetic Resolution of 1,2–Dihydronaphthalene Oxide and Related Epoxides Via Asymmetric C–H Hydroxylation", J. Am .Chem. Soc. 116: 12129–12130 (1994).

Larrow, J. and E. Jacobsen, "A Practical Method for the Large–Scale Preparation of [N,N'—Bis(3,5–di–tert–butylsalicylidene)–1,2–Cyclohexanediaminato (2–)]managanese(III) Chloride, A Highly Enantiocelective Epoxidation Catalyst", J. Org. Chem. 59: 1939–1942 (1994).

Leighton, J. et al., "Efficient synthesis of (R)–4–((Trimethylsily)oxy)–2–Cyclopentenone by Enantioselective Catalytic Epoxide Ring–Opening", Journal of Organic Chemistry vol. 61: No. 1, pp. 389–390 (1996).

Li, Z. et al., "Asymmetric Alkene Aziridination With Readily Available Chiral Diimine–Based Catalysts", J. Am. Chem. Soc. 115(12):5326–5327 (1993).

Marangoni, G. and B. Pitteri "Crystal Structure of Cationic Square Planar Platinum (II) Complexes Containing The Tridentate Chelate Ligand 2,6–Bis(methylthiomethyl)Pyridine", Polyhdron 12(13):1669–1673 (1993).

Martinez, L. et al., "Highly Enantioselective Ring Opening of Epoxides Catalyzed by (Salen) Cr(III) Complexes", J. Am. Chem. Soc. 117:5897–5898 (1995).

Maruoka, K. et al., "An Efficient, Catalytic Procedure For Epoxide Rearrangement", Tetrahedron Letters 30(41): 5607–5610 (1989).

Maruyama, K. et al., "Cobalt Schiff Base Complex Catalysed Solvolytic Ring Opening of Epoxy Compounds", React. Kinet. Catal. Lett. 45(2): 165–171 (1991).

Narasaka, K. "Chiral Lewis Acids In Catalytic Asymmetric Reactions", Synthesis, pp. 1–11 (Jan. 1991).

Nugent, W. et al., "Beyond Nature's Chiral Pool: Enantioselective Catalysis In Industry", Science 259:479–483 (1993).

Nugent, W. "Chiral Lewis Acid Catalysis. Enantioselective Additon of Azide to Meso Epoxides", J. Am. Chem. Soc. 114: 2768–2769 (1992).

Oppolzer, W. and R. Radinov, "Enantioselective Synthesis of Sec–Allylalcohols by Catalytic Asymmetric Addition of Divinylzinc To Aldehydes", Tetrahedron Letters, 29(44): 5645–5648 (1988).

Ozaki, S. et al., "Synthesis of Chiral Square Planar Cobalt (III) Complexes and Catalytic Asymmetric Epoxidation With There Complxes", J. of Chem. Soc. Perkin Trans. 2, Issue 1:353–359 (1990).

Palucki, M. et al., "Highly Enantioselective, Low–Temperature Epoxidation of Styrene", J. Am. Chem. Soc. 116: 9333–9334 (1994).

Palucki, A. et al., "Asymmetric Oxidation of Sulfides With H2O2 Catalyzed By (Salen) Mn(III) Complexes", Tetrahedron Letters, 33 (47):7111–7114 (1992).

Ready and Jacobsen., "Asymmetric Catalytic Synthesis of α–Aryloxy Alcohols: Kinetic Resolution of Terminal Epoxides via Highly Enantioselective Ring–Opening with Phenols", J. Am. Chem. Soc. 121: 6086–6087 (1999).

Sasaki, H. et al., "Rational Design of Mn–Salen Catalyst 2: Highly Enantioselective Epoxidation of Conjugated cis Olefins", Tetrahedron 50(41): 11827–11838 (1994).

Schurig, V. and F. Betschinger, "Metal–Mediated Enantioselective Access to Unfunctionalized Allphatic Oxiranes: Prochiral and Chiral Recognition", Chem. Rev. 92:873–888 (1992).

Srinivasan, K. et al., "Epoxidation of Olefins With Cationic (Salen) Mn III Complexes. The Modulation of Catalytic Activity By Substituents", J. Am. Chem. Soc. 108:2309–2320 (1986).

Stinson, S. "Chiral Drugs", Chemical and Chemical Engineering News, pp. 46–79 (Sep. 28, 1992).

Tokunaga et al., "Asymmetric Catalytis With Water: Efficient Kinetic Resolution of Terminal Epoxides by Means of Catalytic Hydrolysis", Science, 277:936–938 (1997).

Ward, R. "Non–Enzymatic Asymmetric Transformations Involving Symmetrical Bifunctional Compounds", Chem. Soc. Rev. 19:1–19 (1990).

Woolley, P. "Models For Metal Iron Function In Carbonic Anhydrase", Nature, 258:677–682 (1975).

Yamashita, H. "Metal(II) d–Tartrates Catalyzed Asymmetric Ring Opening Of Oxiranes With Various Nucleophiles", The Chemical Society of Japan 61: 1213–1220 (1988).

Zhang, W. et al., "Enantioselective Epoxidation Of Unfunctionalized Olefins Catalyzed By (Selen)manganese Complexes", J. Am. Chem. Soc. 112:2801–2803 (1990).

Zhang, W. and E. Jacobsen, "Asymmetric Olefin Epoxidation With Sodium Hypochlorite Catalyzed by Easily Preparted Chiral Mn (III) Salen Complexes", J. of Org. Chem. 56:2296–2298 (1991).

International Search Report completed Nov. 18, 1999 and mailed Dec. 12, 1999.

International Search Report completed Jul. 17, 1996 and mailed Jul. 25, 1996.

*HKR of tert-Butylethyleneoxide*

* Yield is expressed as a percentage of the theoretical maximum of 50%

HKR of Alkyl-Substituted Terminal Epoxides

> 99% ee

| R | Catalyst (mole %) | Yield (% of theoretical) |
|---|---|---|
| Me | 0.2 | 94 |
| n-Bu | 0.2 | 86 |
| n-$C_{12}H_{25}$ | 0.5 | 86 |
| $CH_2$=CH$(CH_2)_2$ | 0.5 | 85 |
| cyclohexyl | 0.5 | 87 |
| PhCH$_2$ | 0.5 | 92 |

HKR of 3,4-Epoxy-2-butanone

- without O₂, the catalyst reduces out in 6 h with recovered epoxide in 76% ee

- preoxidation of catalyst is required

Hydrolytic Kinetic Resolution of Terminal Epoxides

| Substrate | % ee (%yield) | Substrate | % ee (%yield) |
|---|---|---|---|
| BnO-epoxide | >99 (93) | EtO(C=O)CH2-epoxide | >99 (92) |
| TBSO-epoxide | >99 (96) | PhO-epoxide | >99 (94) |
| H3C-CH2-C(=O)O-CH2-epoxide | >99 (90) | 1-naphthyl-O-CH2-epoxide | >99 (80) |

\* Yields reported as a theoretical maximum of 50%

Brandes *Tetrahedron: Asymm* 1997, 8, 3927

NUCLEOPHILIC KINETIC RESOLUTION OF CYCLIC SUBSTRATES USING SILYL AZIDES

RELATED APPLICATIONS

This application is a continuation of U.S. Ser. No. 10/206,143, filed Jul. 26, 2002; which is a continuation of U.S. Ser. No. 09/899,516, filed Jul. 5, 2001, now U.S. Pat. No. 6,448,414; which is a continuation of U.S. Ser. No. 09/134,393, filed Aug. 14, 1998, now U.S. Pat. No. 6,262,278; which is a continuation-in-part of U.S. Ser. No. 08/622,549, filed on Mar. 25, 1996, now U.S. Pat. No. 5,929,232; which is a continuation-in-part of U.S. Ser. No. 08/403,374, filed Mar. 14, 1995, now U.S. Pat. No. 5,665,890.

GOVERNMENT FUNDING

Work described herein was supported in part with funding from the National Institutes of Health. The United States Government has certain rights in this invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include fewer side effects and greater potency of enantiomerically pure compounds.

Traditional methods of organic synthesis have often been optimized for the production of racemic materials. The production of enantiomerically pure material has historically been achieved in one of two ways: use of enantiomerically pure starting materials derived from natural sources (the so-called "chiral pool"), or resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus wasting half of the material.

Epoxides are valuable intermediates for the stereocontrolled synthesis of complex organic compounds due to the variety of compounds which can be obtained by epoxide-opening reactions. For example, α-amino alcohols can be obtained simply by opening of an epoxide with azide ion, and reduction of the resulting α-azido alcohol (for example, by hydrogenation). The, reaction of epoxides with other nucleophiles similarly yields functionalized compounds which can be converted to useful materials. A Lewis acid may be added to act as an epoxide-activating reagent.

The utility of epoxides has expanded dramatically with the advent of practical asymmetric catalytic methods for their synthesis (Johnson, R. A.; Sharpless, K. B. In *Catalytic Asymmetric Synthesis*. Ojima, I., Ed.: VCH: New York, 1993; Chapter 4.1. Jacobsen, E. N. *Ibid*. Chapter 4.2). In addition to epoxidation of prochiral and chiral olefins, approaches to the use of epoxides in the synthesis of enantiomerically enriched compounds include kinetic resolutions of racemic epoxides (Maruoka, K.; Nagahara, S.; Ooi, T.; Yamamoto, H. *Tetrahedron Lett* 1989, 30, 5607. Chen, X.-J.; Archelas, A.; Rurstoss, R. *J Org Chem* 1993, 58, 5528. Barili, P. L.; Berti, G.; Mastrorilli, E. *Tetrahedron* 1993, 49, 6263.)

A particularly desirable reaction is the asymmetric ring-opening of symmetrical epoxides, a technique which utilizes easily made achiral starting materials and can simultaneously set two stereogenic centers in the functionalized product. Although the asymmetric ring-opening of epoxides with a chiral reagent has been reported, in most previously known cases the enantiomeric purity of the products has been poor. Furthermore, many previously reported methods have required stoichiometric amounts of the chiral reagent, which is likely to be expensive on a large scale. A catalytic asymmetric ring-opening of epoxides has been reported (Nugent, W. A., *J Am Chem Soc* 1992, 114, 2768); however, the catalyst is expensive to make. Furthermore, good asymmetric induction (>90% e.e.) was observed only for a few substrates and required the use of a Lewis acid additive. Moreover, the catalytic species is not well characterized, making rational mechanism-based modifications to the catalyst difficult.

SUMMARY OF THE INVENTION

In one aspect of the present invention, there is provided a process for stereoselective chemical synthesis which generally comprises reacting a nucleophile and a chiral or prochiral cyclic substrate in the presence of a non-racemic chiral catalyst to produce a stereoisomerically enriched product. The cyclic substrate comprises a carbocycle or heterocycle having a reactive center susceptible to nucleophilic attack by the nucleophile, and the chiral catalyst comprises an asymmetric tetradentate or tridentate ligand complexed with a metal atom. In the instance of the tetradentate ligand, the catalyst complex has a rectangular planar or rectangular pyramidal geometry. The tridentate ligand-metal complex assumes a planar or trigonal pyramidal geometry. In a preferred embodiment, the ligand has at least one Schiff base nitrogen complexed with the metal core of the catalyst. In another preferred embodiment, the ligand provides at least one stereogenic center within two bonds of a ligand atom which coordinates the metal.

In general, the metal atom is a transition metal from Groups 3–12 or from the lanthanide series, and is preferably not in its highest state of oxidation. For example, the metal can be a late transition metal, such as selected from Group 5–12 transition metals. In preferred embodiments, the metal atom is selected from the group consisting of Cr, Mn, V, Fe, Co, Mo, W, Ru and Ni.

In preferred embodiments, the substrate which is acted on by the nucleophile and catalyst is represented by the general formula 118:

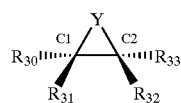

118 in which
Y represents O, S, N(R$_{50}$), C(R$_{52}$)(R$_{54}$), or has the formula A-B-C; wherein R$_{50}$ is selected from the set comprising hydrogen, alkyls, acyls, carbonyl-substituted alkyls, carbonyl-substituted aryls, and sulfonyls; R$_{52}$ and R$_{54}$ each independently represent an electron-withdrawing group; A and C are independently absent, or represent a C$_1$–C$_5$ alkyl, O, S, carbonyl, or N(R$_{50}$); and B is a carbonyl, a thiocarbonyl, a phosphoryl, or a sulfonyl; and $R_{30}$, $R_{31}$, $R_{32}$, and $R_{33}$ independently represent an organic or inorganic substituent which forms a covalent bond with the C1 or C2 carbon atoms of 118, and which permit formation of a stable ring structure including Y. For instance, the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents $R_{30}$, $R_{31}$, $R_{32}$, and $R_{33}$ taken together form a carbocylic or heterocyclic ring having from 4 to 8 atoms in the ring structure. In this formula, $R_7$ represents an aryl, a cycloalkyl, a cycloalkenyl, a heterocycle or a polycycle; and m is an integer in the range of 0 to 8 inclusive. In certain embodiments, $R_{30}$, $R_{31}$, $R_{32}$, and $R_{33}$ are chosen such that the substrate has a plane of symmetry.

Exemplary cyclic substrates for the subject reactions include epoxides, aziridines, episulfides, cyclopropanes, lactones, thiolactones, lactams, thiolactams, cyclic carbonates, cyclic thiocarbonates, cyclic sulfates, cyclic anhydrides, cyclic phosphates, cyclic ureas, cyclic thioureas, and sultones.

In a preferred embodiment, the method includes combining a nucleophilic reactant, a prochiral or chiral cyclic substrate, and a non-racemic chiral catalyst as described herein, and maintaining the combination under conditions appropriate for the chiral catalyst to catalyze stereoselective opening of the cyclic substrate at the electrophilic atom by reaction with the nucleophilic reactant.

In preferred embodiments, the chiral catalyst which is employed in the subject reaction is represented by the general formula:

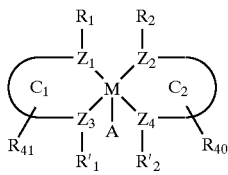

100 in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the transition metal; and

A represents a counterion or a nucleophile, wherein each $R_1$, $R_2$, $R'_1$, $R'_2$ $R_{40}$ and $R_{41}$ are selected to provide at least one stereogenic center in the tetradentate ligand.

In exemplary embodiments, $R_1$, $R_2$, $R'_1$ and $R'_2$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

each $R_{40}$ and $R_{41}$ occurring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

$R_7$ represents an aryl, a cycloalkyl, a cycloalkenyl, a heterocycle or a polycycle;

$Z_1$, $Z_2$, $Z_3$ and $Z_4$ are independently selected from the group consisting of nitrogen, oxygen, phosphorus, arsenic, and sulfur; and m is an integer in the range of 0 to 8 inclusive.

For example, the catalyst can be represented by the general formula:

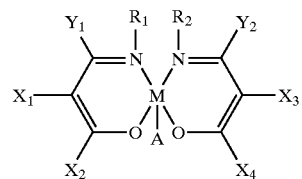

in which the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocycle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;

$R_7$ represents an aryl, a cycloalkyl, a cycloalkenyl, a heterocycle, or a polycycle;

m is an integer in the range of 0 to 8 inclusive;

M represents the transition metal; and

A represents a counterion or a nucleophile, wherein each of the substituents $R_1$, $R_2$, $Y_1$, $Y_2$, $X_1$, $X_2$, $X_3$ and $X_4$, are selected such that the catalyst is asymmetric.

For example, a preferred class of catalysts are represented by the general formula:

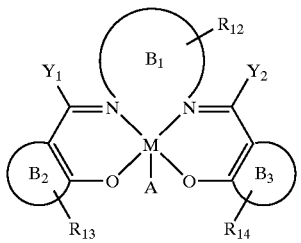

in which
- the $B_1$ moiety represents a diimine bridging substituent represented by $-R_{15}-R_{16}-R_{17}-$, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sufonyl, a selenium, a carbonyl, or an ester;
- each of $B_2$ and $B_3$ independently represent rings selected from a group consisting of cycloalkyls, cycloakenyls, aryls, and heterocyclic rings, which rings comprising from 4 to 8 atoms in a ring structure;
- $Y_1$ and $Y_2$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;
- $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$, wherein $R_{12}$ can occur on one or more positions of $-R_{15}-R_{16}-R_{17}-$,
- or any two or more of the $R_{12}$, $R_{13}$, $R_{14}$, $Y_1$ and $Y_2$ taken together form a bridging substituent;
- $R_7$ represents an aryl, a cycloalkyl, a cycloalkenyl, a heterocycle, or a polycycle;
- m is an integer in the range of 0 to 8 inclusive;
- M represents a transition metal; and
- A represents a counterion or a nucleophile, wherein $R_{12}$, $R_{13}$, $R_{14}$, $Y_1$ and $Y_2$ are selected such that the catalyst is asymmetric.

In yet further preferred embodiments, the catalyst is a metallosalenate catalyst represented by the general formula:

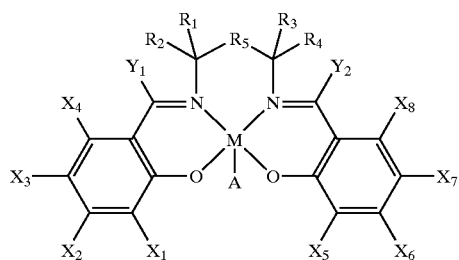

in which
- each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;
- or any two or more of the substituents taken together form a carbocycle or heterocycle having from 4 to 10 atoms in the ring structure;
- $R_7$ represents an aryl, a cycloalkyl, a cycloalkenyl, a heterocycle or a polycycle;
- m is an integer in the range of 0 to 8 inclusive;
- M represents a transition metal; and
- A represents a counterion or a nucleophile;

wherein if $R_5$ is absent, at least one of $R_1$ and $R_2$ is taken together with at least one of $R_3$ and $R_4$ to form a bridging substituent, and each of the substituents of 106 are selected such that the salenate is asymmetric.

Alternatively, the catalyst may comprise a tridentate ligand, such as the catalysts represented by general formula 140:

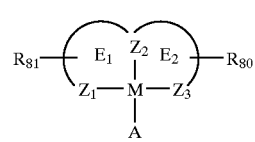

in which
- $Z_1$, $Z_2$, and $Z_3$ each represent a Lewis base;
- the $E_1$ moiety, taken with $Z_1$, $Z_2$ and M, and the $E_2$ moiety, taken with $Z_2$, $Z_3$ and M, each, independently, form a heterocycle;
- $R_{80}$ and $R_{81}$ each, independently, are absent, or represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or $-(CH_2)_m-R_7$, or any two or more of the $R_{80}$ and $R_{81}$ substituents taken together form a bridging substituent;
- $R_7$ represents an aryl, a cycloalkyl, a cycloalkenyl, a heterocycle or a polycycle;
- m is an integer in the range of 0 to 8 inclusive;
- M represents a transition metal; and
- A represents a counteranion or a nucleophile;

wherein the tridentate ligand is asymmetric.

As described herein, the subject method can be used for carrying out enantioselective ring openings, diastereoselective ring openings (including kinetic resolutions), and stereoselective ring expansions of cyclic compounds.

DETAILED DESCRIPTION OF THE INVENTION

Figure 1:
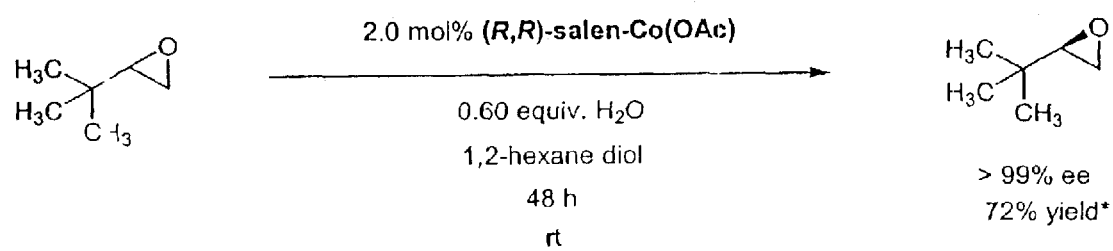
FIG. 1 depicts the hydrolytic kinetic resolution of tert-butylethylene oxide.
Figure 2:
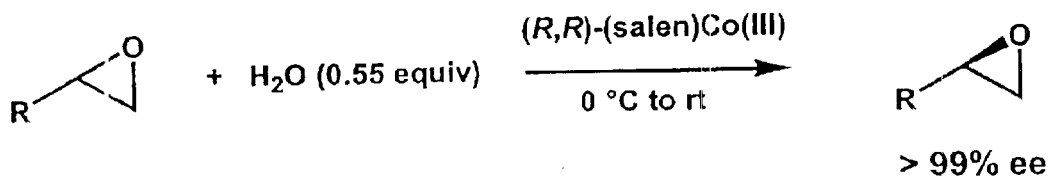
FIG. 2 depicts the hydrolytic kinetic resolution of alkyl-substituted terminal epoxides.
Figure 3:
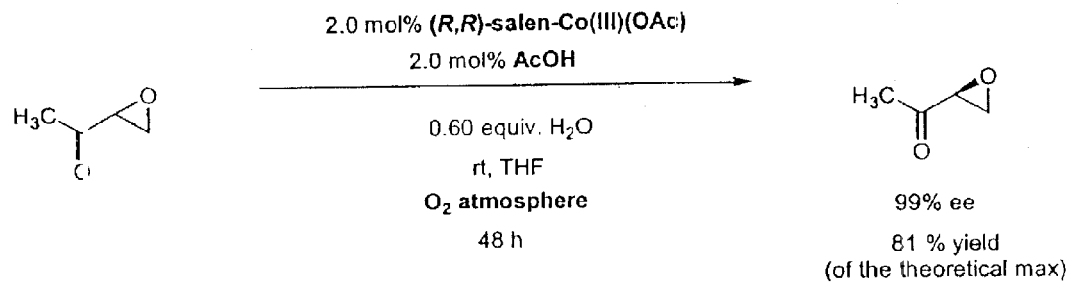
FIG. 3 depicts the hydrolytic kinetic resolution of 3,4-epoxy-2-butanone.
Figure 4:
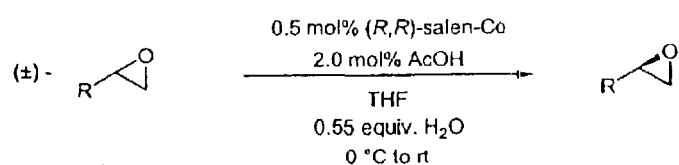
FIG. 4 depicts the hydrolytic kinetic resolution of terminal epoxides.
Figure 5:
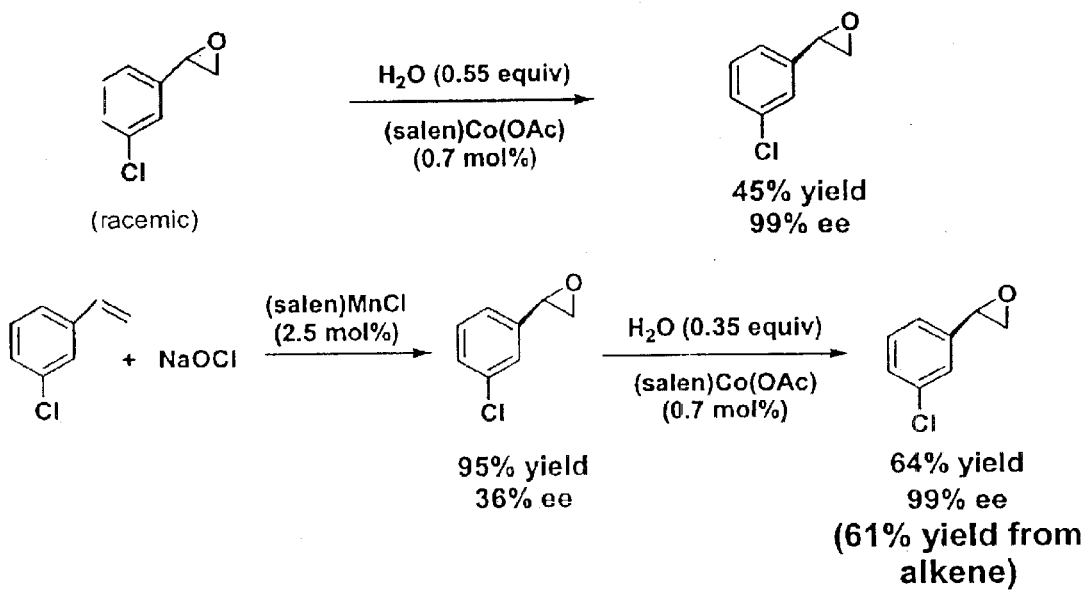
FIG. 5 depicts the kinetic resolution of m-chlorostyrene oxide.

The ability to introduce a stereocenter selectively or to resolve a racemic mixture has broad application, especially in the agricultural and pharmaceutical industries, as well as in the polymer industry. As described herein, the present invention makes available methods and reagents for stereoselective and regioselective synthesis involving nucleophile-mediated ring opening reactions. The primary constituents of the method, set out in more detail below, are a chiral metal catalyst of particular tetradenitate or tridentate geometry; a chiral or prochiral "substrate" including a carbocycle or heterocycle moiety with at least one electrophilic ring atom; and a nucleophilic reactant which is desired to be added at the site of the electrophilic ring atom.

I. Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "ring expansion" refers to a process whereby the number of atoms in a ring of a cyclic compound is increased. An illustrative example of ring expansion is the reaction of epoxides with carbon dioxide to yield cyclic carbonates.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderence of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "complex" as used herein and in the claims means a coordination compound formed by the union of one or more electronically rich molecules or atoms capable of independent existence with one or more electronically poor molecules or atoms, each of which is also capable of independent existence.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\text{\% enantiomeric excess A (ee)} = (\text{\% enantiomer A}) - (\text{\% enantiomer B})$$

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective reaction of an unsymmetrically substituted epoxide substrate would cause preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple carbon-carbon bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, an "amine" can be represented by the general formula:

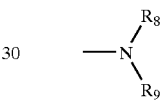

wherein $R_8$ and $R_9$ each independently represent a hydrogen, an alkyl, an alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

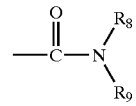

wherein $R_8$ and $R_9$ are as defined above.

The term "alkylimine" refers to an alkyl group having a substituted or unsubstituted imine attached thereto. An "imine" can be represented by the general formula:

wherein $R_8$ is as described above.

The term "thioalkyl" refers to an alkyl group, as defined above, having a sulfhydryl or thioether group attached thereto. In preferred embodiments, the "thioether" moiety is represented by one of —S-alkyl, —S-alkenyl, —S-alkynyl, and —S—$(CH_2)_m$—$R_7$; wherein m and $R_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

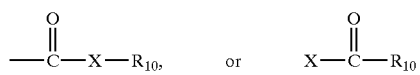

wherein X is absent or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, the formula represents an "ester". Where X is a sulfur, the formula represents a "thioester." Where X is absent, and $R_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refer to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O-alkyl, —O-alkenyl, —O-alkynyl, —O—$(CH_2)_m$—$R_7$, where m and $R_7$ are described above.

Thus, the term "phosphorylalkyl" as used herein means an alkyl group, as defined above, having a substituted or unsubstituted phosphoryl group attached thereto. A "phosphoryl" can in general be represented by the formula:

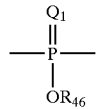

wherein $Q_1$ represented S or O, and $R_{46}$ represents hydrogen, a lower alkyl or an aryl. When used to substitute an alkyl, the phosphoryl group of the phosphorylalkyl can be represented by the general formula:

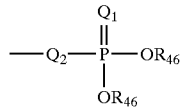

wherein $Q_1$ represented S or O, and each $R_{46}$ independently represents hydrogen, a lower alkyl or an aryl, $Q_2$ represents O, S or N.

The term "metalloalkyl" refers to an alkyl group, as defined above, having a substituted or unsubstituted organometallic group attached thereto. A "silyl alkyl" is an alkyl having a substituted silicon attached thereto. In a preferred embodiment, the "silyl" moiety which may be substituted on the alkyl can be represented by the general formula:

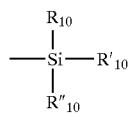

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, a "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

The term "sulfonyl" as used herein means a $S(O)_2$ moiety bonded to two carbon atoms. Thus, in a preferred embodiment, a sulfone has the following structure:

wherein the single bonds are between carbon and sulfur.

The term "sulfonate" as used herein means a sulfonyl group, as defined above, attached to a hydroxyl, alkyloxy or aryloxy group. Thus, in a preferred embodiment, a sulfonate has the structure:

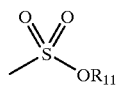

in which $R_{11}$ is absent, hydrogen, alkyl, or aryl.

The term "sulfate", as used herein, means a sulfonyl group, as defined above, attached to two hydroxy or alkoxy groups. Thus, in a preferred embodiment, a sulfate has the structure:

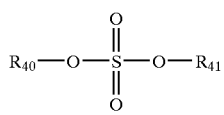

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms, "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R_{15}$—$R_{16}$—$R_{17}$—, wherein $R_{15}$ and $R_{17}$ each independently are absent or represent an alkyl, an alkenyl, or an alkynyl, preferably $C_1$ to $C_{10}$, and $R_{16}$ is absent or represents an amine, an imine, an amide, a phosphoryl a carbonyl, a silyl, an oxygen, a sulfonyl, a sulfer, a selenium, or an ester. Exemplary bridging substituents are given by the "picnic basket" forms of, for instance, the porphoryn catalysts described below.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenlesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

II. Catalyzed Reactions

In one aspect of the present invention there is provided a process for stereoselectively producing compounds with at least one stereogenic center. An advantage of this invention is that enantiomerically enriched products can be synthesized from achiral or racemic reactants. Another advantage is that yield losses associated with the production of an undesired enantiomer can be substantially reduced.

In general, the invention features a stereoselective ring opening process which comprises combining a nucleophilic reactant, a prochiral or chiral cyclic substrate, and at least a catalytic amount of non-racemic chiral catalyst of particular characteristics (as described below). The cyclic substrate of the reaction will include a carbocycle or heterocycle which has an electrophilic atom susceptible to attack by the nucleophile. The combination is maintained under conditions appropriate for the chiral catalyst to catalyze stereoselective opening of the cyclic substrate at the electrophilic atom by reaction with the nucleophilic reactant. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

In an exemplary embodiment, a meso-epoxide can be opened with a nucleophile, e.g., trimethylsilyl azide (TMS-$N_3$), in the presence of a chiral catalyst of the subject reaction.

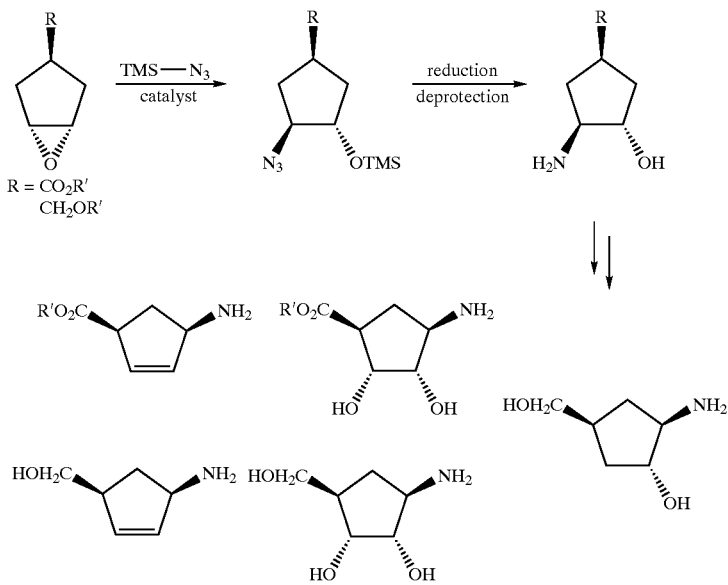

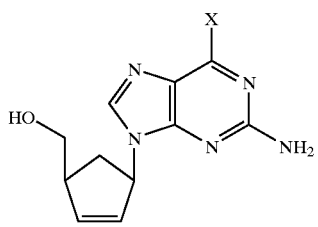

X = OH:Carbovir

X = NH—⌬ :1592U89

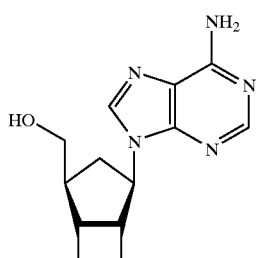

Aristeromycin

The above opening of a meso-epoxide in the presence of a chiral catalyst yields an enantiomerically-enriched silyl-protected α-azidoalcohol, which can be transformed, through standard manipulations, to a variety of products; a few examples of these products are shown above. These products are useful for the synthesis of compounds with potential antiviral activity, such as the three carbocyclic nucleoside analogs shown below, some of which are in clinical trials.

-continued

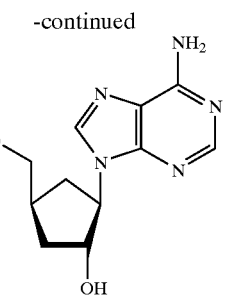

3'-Deoxyaristeromycin

The present invention also provides a practical method of synthesizing precursors for prostaglandins, including key intermediates used in the commercial production of prostaglandins. As shown below, the subject ring-opening of a meso-epoxide produces an enantiomerically enriched product which is easily converted to a useful intermediate.

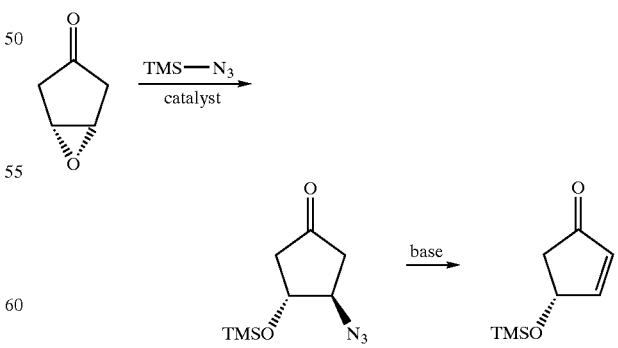

In another illustrative embodiment, the present invention provides a method for synthesizing balanol, a potent protein kinase C inhibitor, as shown below.

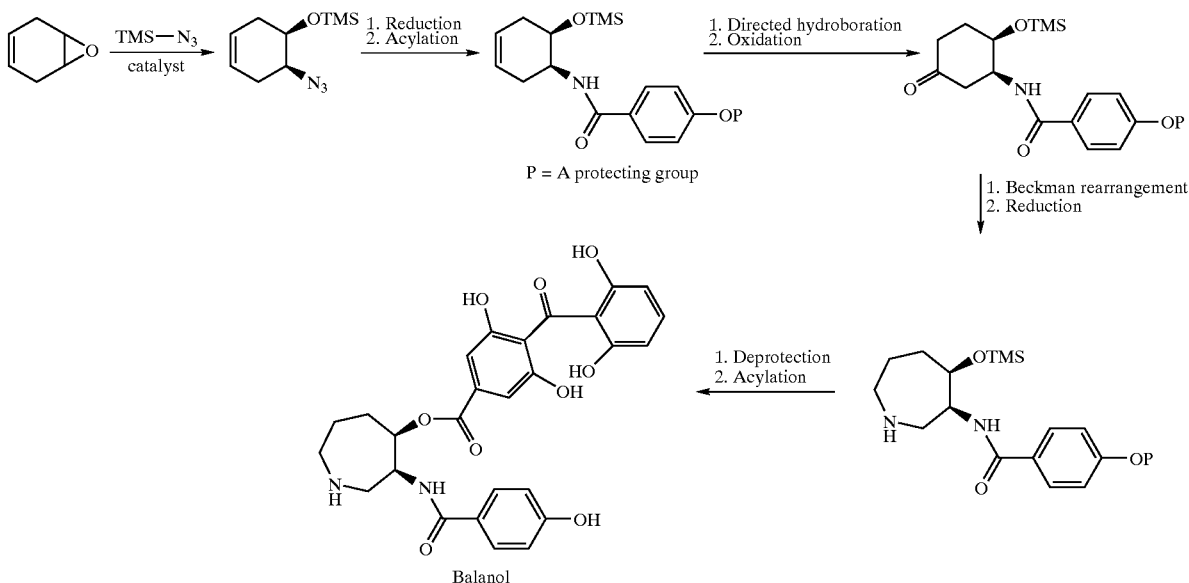

Balanol

In yet another exemplary embodiment, the subject method can be used to catalyze the stereoselective ring-opening of a meso-aziridine with a nucleophile, such as with the nucleophile, ammonia exemplified below:

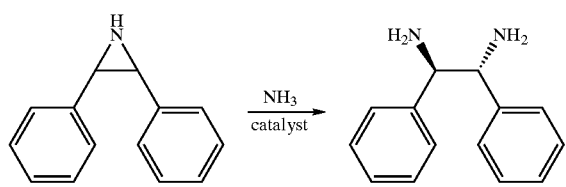

In this case, the chiral diamines are useful in, for example, synthesis of certain of the chiral ligands of the catalyst described herein. For instance, such chiral diamines can be used to make metallosalenate catalysts for use in the method of the present invention.

The ring-opening of a meso-episulfide with an amine in the presence of a chiral catalyst, shown below, is another exemplary reaction of the subject method which can be carried out stereoselectively.

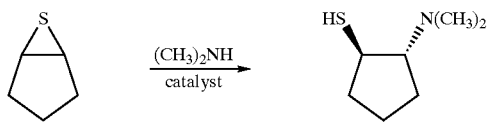

The product non-racemic amino thiols are useful in, for example, the synthesis of asymmetric penicillin analogs.

In another embodiment, the opening of a meso cyclic sulfate with an acetylide can be carried out in the presence of a chiral catalyst of the subject method, such as illustrated below:

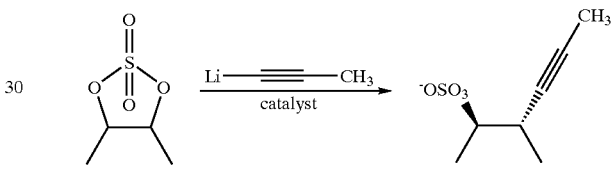

The sulfate group of the product can be removed to reveal the homopropargylic alcohol, or can be exploited as a protecting group in further synthesis steps.

Still another ring-opening reaction contemplated by the present method is the opening of a meso-cyclopropane by a mercaptan in the presence of one of the subject chiral catalyst:

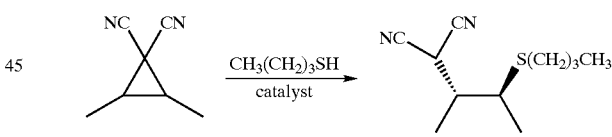

The product may be converted, for example, to a 3,4-substituted carboxylic acid by hydrolysis and decarboxylation.

In certain embodiments, the subject reaction can be used for a reaction involving intramolecular ring-opening. For instance, as illustrated below, an epoxide can be opened by an alcohol moiety of the same molecule in the presence of a chiral catalyst in accordance with the present method:

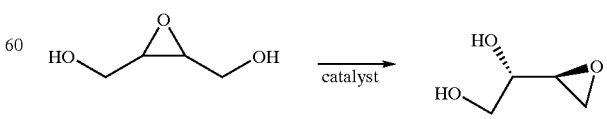

The product 1,2-epoxy diol can easily be converted to a variety of natural and non-natural products such as sugars and sugar analogs.

Still another exemplary ring-opening scheme of the present invention is generally illustrated below by the opening of a cyclic carbonate with an amine:

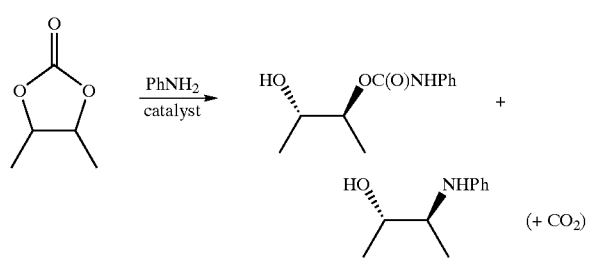

It will be understood that two different products may result from this ring opening, depending on whether nucleophilic attack is favored at the carbonyl carbon or the hydroxylic carbon. The ratio of products can be adjusted to favor one or the other by manipulation of such factors as the nucleophile, the chiral catalyst, and the reaction conditions employed. Both products can be converted to synthetically useful products by conventional methods.

Still another enantioselective reaction is demonstrated by the ring-opening of a meso-epoxide by an organocopper reagent in the presence of a chiral catalyst, as is shown below:

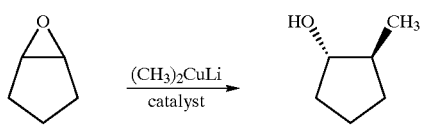

In another aspect of the present invention, kinetic resolution of enantiomers occurs by catalysis, by a subject chiral catalyst, of a ring-opening reaction of a racemic substrate. In the subject metal-mediated kinetic resolution process for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting compounds. For example, propylene oxide is a versatile reagent for introduction of a functionalized three-carbon unit into a molecule. However, pure (S)-propylene oxide is very expensive, costing up to 300 times more than the corresponding racemic mixture. Thus, although kinetic resolution according to the present method may result in the waste of half of the racemic substrate, large cost savings may be realized by use of the racemic mixture. Examples of such kinetic resolutions are shown below.

For instance, catalyst-mediated kinetic resolution of chiral oxiranes (e.g. chiral recognition) described herein represents important alternate approaches to asymmetric epoxidation (prochiral recognition) processes of the prior art because racemic oxiranes are easily accessible and are often produced at a large industrial scale rendering acceptable the loss of the antipode. Stereoselectivity in the kinetic resolution of oxiranes by the subject reaction processes is determined by the chirality of the catalyst.

In an exemplary embodiment, the kinetic resolution of a racemic epoxide is shown below.

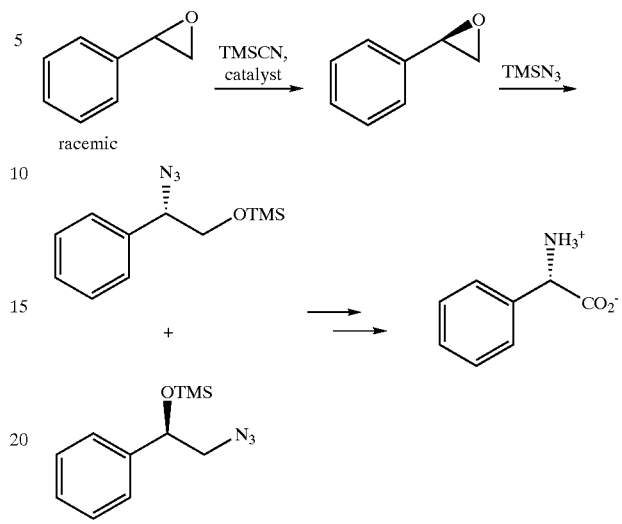

One enantiomer of styrene epoxide is preferentially consumed by trimethylsilyl cyanide in the presence of a chiral catalyst. The remaining enantiomer of styrene oxide is then reacted with TMS-azide to yield a pair of regioisomeric, enantiomerically-pure silyl-protected α-azidoalcohols. The desired regioisomer can be made the major product by choice of appropriate reaction conditions. The α-phenylazide isomer can be converted, through conventional reactions, to the unnatural amino acid (S)-phenylglycine. The ability to carry out this conversion has significant commercial value since optically active amino acids and amino acid analogs are biologically important and have many agricultural and pharmaceutical applications. The β-phenylazide isomer can also be converted to pharmaceutically useful products.

In certain embodiments, the subject catalysts may be used in kinetic resolutions of racemic cyclic substrates wherein the nucleophile is a co-solvent. Suitable nucleophiles of this type include water, alcohols, and thiols. In a preferred embodiment, racemic propylene oxide is reacted, in the presence of a subject catalyst, with about one-half an equivalent of water to yield two valuable, enantiomerically-enriched products: propylene oxide and 1,2-propanediol.

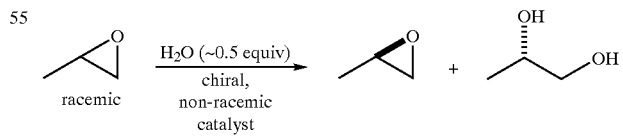

In another preferred embodiment based on the co-solvent invention outlined above, racemic styrene oxide reacts, in the presence of a subject catalyst, with about one-half an equvalent of ethanethiol to yield two enantiomerically-enriched products.

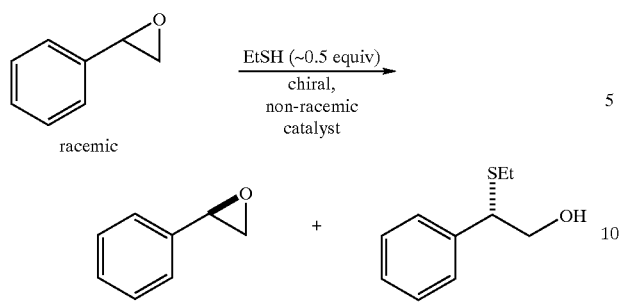

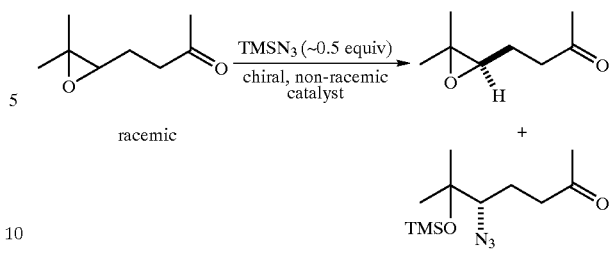

Ring-opening of cyclic sulfates by amines, followed by treatment with a base, is a useful method of producing aziridines, as disclosed in U.S. Pat. No. 5,321,143 to Sharpless. Thus, ring-opening of a racemic chiral cyclic sulfate with an amine, in the presence of a chiral catalyst according to the present invention, followed by treatment with a base, is a method of preparing enantiomerically enriched aziridines.

In another illustrative embodiment, the subject method can be used to provide enantiomerically enriched compounds useful in the synthesis of the anti-anginal drug diltiazem.

treatment of the racemic epoxide with TMS-azide or the like in the presence of one of the subject chiral catalyst which is enantioselective for the (S)-epoxide can yield, after separation, the optically pure (R)-epoxide.

In yet another illustrative embodiment, the subject method can be used for kinetic resolution of α-bisabolol stereoisomers during synthesis from epoxylimonene precursors. The (−)-α-bisabolol enantiomer is used on an industrial scale for the preparation of various skin-care creams, lotions and ointments because of its anti-inflammatory, bactericidal, and anti-mycotic properties. In a representative reaction scheme:

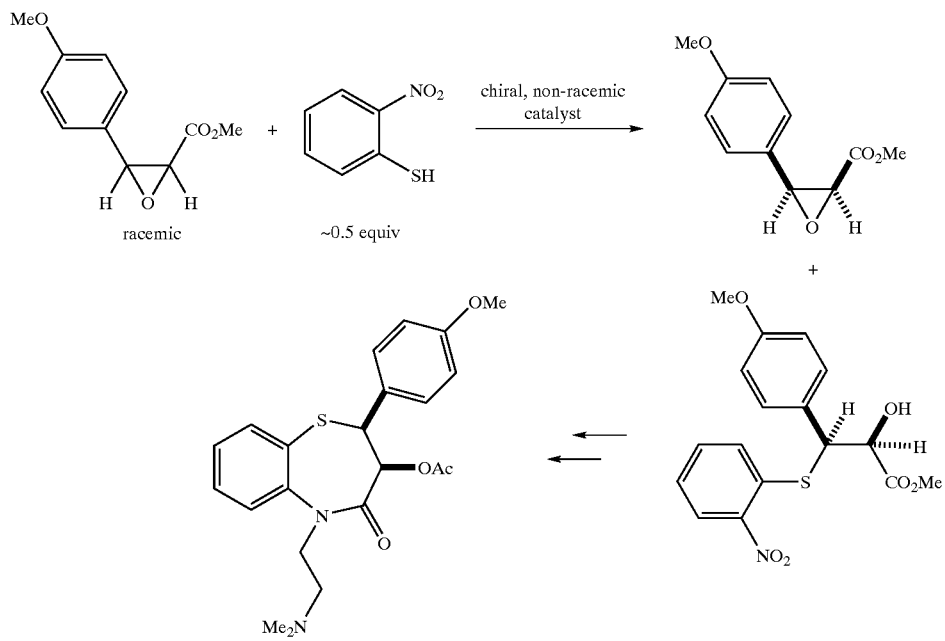

The racemic mixture of cis-epoxides is resolved by reaction with 2-nitrothiophenol in the presence of a chiral catalyst, and the enantiorierically enriched ring-opened product is separated from the unreacted epoxide. The ring-opened product is then transformed to diltiazem by standard techniques.

Still another example of kinetic resolution with a reaction of the present invention involves the synthesis of juvenile hormone. In the reaction scheme:

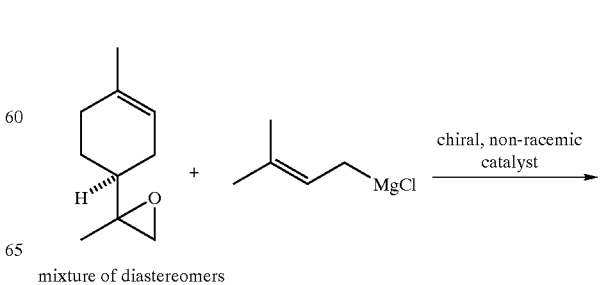

mixture of diastereomers

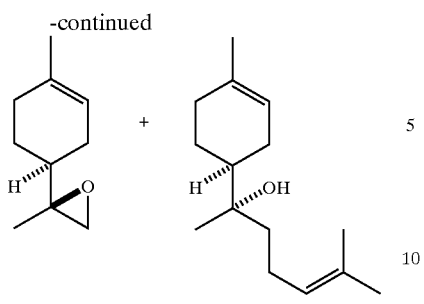

a mixture containing (4S,8R)- and (4S,8S)-8,9-epoxy-p-menth-1-ene, obtained from 4(S)-limonene (Husstedt et al. (1979) *Synthesis* 966), is reacted with (3-methylbut-2-enyl) magnesium chloride in the presence of a chiral catalyst described herein. The resulting (−)-α-bisabolol can be isolated from the unreacted (4S,8R)-epoxide by, for example, flash chromatography. Alternatively, the racemic limonene epoxide mixture can be reacted with TMS-azide or the like in the presence of the antipodal chiral catalyst used in the illustrated reaction scheme in order to remove the (4S,8R)-epoxide, and subsequently reacting the remaining (4S,8S)-epoxide with (3-methylbut-2-enyl)$_m$agnesium chloride in the presence of copper iodide.

An another embodiment of a kinetic resolution reaction, there is provided a scheme for the ring-opening of a lactam with a nucleophile. For example, thiophenol can be reacted with a lactam in the presence of a chiral catalyst according to the present invention:

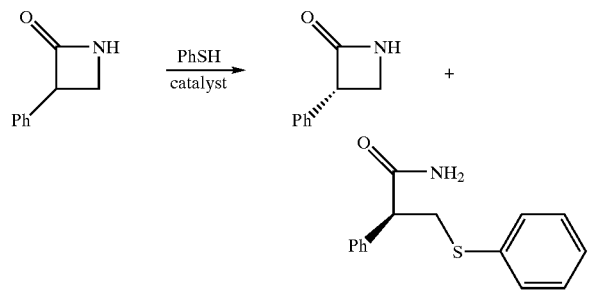

This aspect of the invention provides methods of easily synthesizing functionalized nonracemic products from inexpensive racemic starting materials. It will be noted that lactams have two potential modes of ring opening, viz. at the acyl carbon and at the nitrogen-bearing sp$^3$ carbon. Either mode is suitable for kinetic resolution according to the present invention. Which of the two modes of reaction will predominate will depend upon the particular substrate, nucleophile, catalyst, and reaction conditions employed, and can be determined and accordingly adjusted for the desired reaction by routine experimentation. In general, more highly strained, small-ring (e.g. 3- or 4-membered lactams) will be more likely to undergo cleavage at the sp$^3$ carbon.

In another illustrative embodiment, the present invention provides for the kinetic resolution of lactones by opening with such nucleophiles as a phenyl selenide anion in the presence of a chiral catalyst, as shown below:

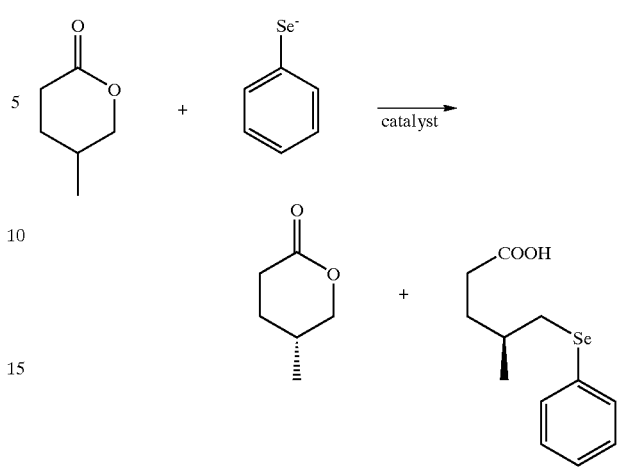

As with the lactan example shown above, two possible modes of ring-opening may operate to kinetically resolve the racemic substrate. As previously noted, more strained substrates will be more prone to undergo addition at the sp$^3$ carbon. However, certain nucleophiles, such as phenylselenide, are known to favor attack at the sp$^3$ carbon under appropriate conditions, even for larger ring lactones.

In another aspect of the present invention, kinetic resolution of enantiomers occurs by catalysis with a chiral catalyst of a ring expansion reaction of a racemic substrate. An example of such a kinetic resolution is shown below.

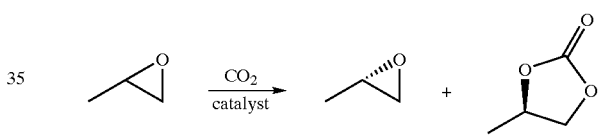

The racemic propylene oxide is resolved by reaction with carbon dioxide in the presence of a chiral catalyst. The resolved propylene oxide is a valuable reagent for use in synthesis of chiral materials, but is very expensive to purchase in enantiomerically pure form. The instant invention provides a highly economical method of producing such enantiomerically enriched materials.

In another aspect of the invention, kinetic resolution of diastereomers occurs by reaction of a diastereomeric mixture of a substrate with a nucleophile in the presence of a chiral catalyst. An illustrative example of such a diastereoselective reaction is shown below.

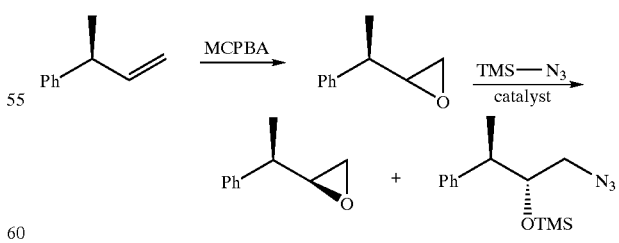

In this example, a mixture of diastereomers is generated by the epoxidation of a chiral alkene with MCPBA. The mixture of diastereomers is then resolved by reaction with trimethylsilyl azide in the presence of a chiral catalyst. The resolved diastereomers may then be easily separated. This method of resolution provides a simple means of separating diastereomers which may not be easily separated by other methods such as distillation or chromatography.

In another aspect of the invention, the reaction of a substrate with a nucleophile in the presence of a chiral catalyst occurs in a regioselective manner. An illustrative example of a regioselective reaction is shown below.

tioselectivity or diastereoselectivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions,

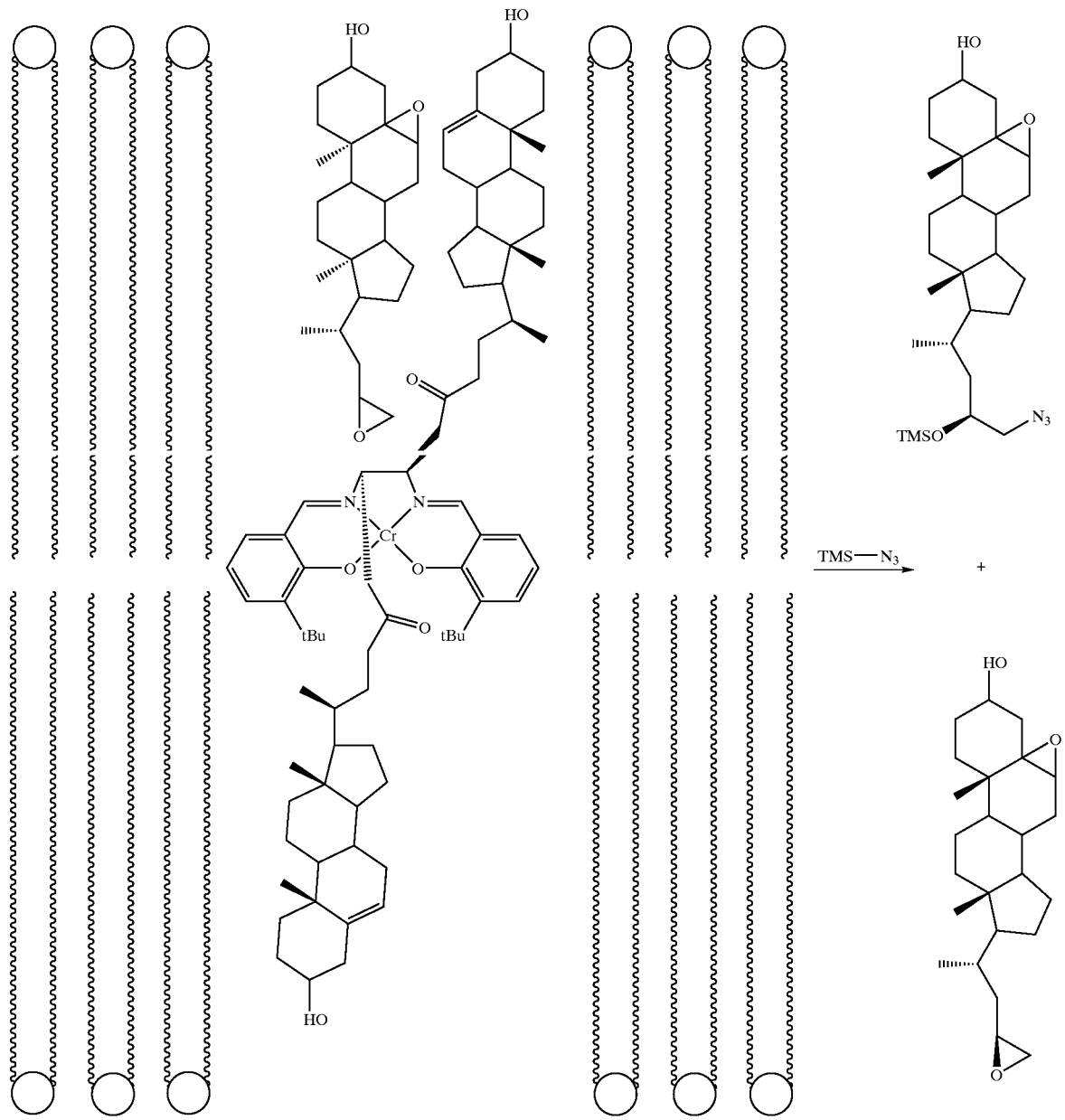

In this example, a steroidal bis-epoxide is reacted with trimethylsilyl azide in the presence of a chiral catalyst in a lipid bilayer. The chiral catalyst in this example is derivatized with steroidal groups, and can be further substituted with alkyl or other substituents to optimize the polarity of the catalyst and the selectivity of the reaction. Only one of the two epoxide moieties is opened by the nucleophile, and only one of the diastereomers is reactive. This reaction is therefore both regioselective and diastereoselective.

The processes of this invention can provide optically active products with very high stereoselectivity (e.g., enanmolar ratios for desired/undesired regioisomers of preferably greater than 5:1, more preferably greater, than 10:1 and most preferably greater than 25:1 can be obtained by the processes of this invention. The processes of this invention can also be carried out at highly desirable reaction rates suitable for commercial use.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes, N-alkylation of amides, addition of aldehydes to amides, nitrile reduction, acylation of ketones by esters, acylation of amines and the like. To further illustrate, exemplary classes of pharmaceuticals which can be synthesized by a scheme including the subject stereoselective reaction are cardiovascular drugs, nonsteroidal anti-inflammatory drugs, central nervous system agents, and antihistaminics.

III. Catalysts

The catalysts employed in the subject method involve chiral complexes which provide controlled steric environments for asymmetric opening of a carbocycle or heterocycle coupled, in certain preferred embodiments, with the generation of one or two new stereocenters upon reaction with a nucleophile. In general, catalysts intended by the present invention can be characterized in terms of a number of features. For instance, a salient aspect of each of the catalysts contemplated by the instant invention concerns the use of metalloligands which provide a rigid or semi-rigid environment near the catalytic site of the molecule. This feature, through imposition of structural rigidity on the chelated metal, can be used to establish selective approach of the substrate to the catalytic site and thereby induce stereoselectivity and/or regioselectivity in a ring opening reaction. Moreover, the ligand preferably places a restriction on the coordination sphere of the metal.

Another aspect of the catalyst concerns the selection of metal atoms for the catalyst. In general, any transition metal (e.g., having d electons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12, in order to provide metal centers which are coordinatively unsaturated and not in their highest oxidation state. For example, suitable metals include Cr, Mn, V, Fe, Co, Mo, W, Ru and Ni. Particularly preferred metals are from group 6, especially Cr(III) and Co(III).

A. Chiral Tetradentate Catalysts

Consistent with these desirable features, one class of particularly preferred chiral catalysts provide a chiral tetradentate ligand which coordinates a transition metal in a substantially square planar or square pyramidal geometry, though some distortion to these geometries is contemplated. Restated, these square geometries refer to tetradentate ligands in which the Lewis basic atoms lie substantially in the same plane, with the metal also in that plane (square planar), or above or below that plane (square pyramidal).

Preferred square tetradentate catalysts which may be employed in the subject reactions can be represented by the general formula 100:

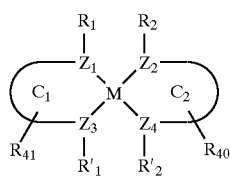

100 wherein $Z_1$, $Z_2$, $Z_3$ and $Z_4$ each represent a Lewis base, such as selected from the group consisting of nitrogen (e.g., imines, amines and amides), oxygen, phosphorus (e.g., phosphines or phosphinites), arsenic (arsines) and sulfur.

The $C_1$ moiety (taken with $Z_1$, $Z_3$ and M) and the $C_2$ moiety, (taken with $Z_2$, $Z_4$ and M) each, independently, form a heterocyclic ring. It will be understood that while the $C_1$ and $C_2$ structures depicted in the above formula may not formally be covalently closed rings for lack of a covalent bond with the metal M, for purposes of this disclosure, this and similar structures involving the metal catalyst atom M will nevertheless be referred to as heterocyclic rings, and substituents thereof will be referenced relative to heterocycle nomenclature (e.g., "fused rings" or "bridged rings"). In addition to substitutions at $R_1$, $R_2$, $R'_1$ and $R'_2$, the $C_1$ and $C_2$ rings can of course be substituted as appropriate at other ring positions, as illustrated by $R_{40}$ and $R_{41}$. Moreover, it will be appreciated that in certain embodiments two or more substituents of $C_1$ can be covalently bonded to each other to provide a fused ring or bridged ring including the $C_1$ ring atoms. Similar structures can be provided on the $C_2$ ring.

Accordingly, in the illustrated structure 100, $R_1$, $R_2$, $R'_1$ and $R'_2$ each independently are absent, or represent some substitution, as permitted by valence requirements, of the Lewis basic atoms, which substitution may be with hydrogen, halogens, alkyls, alkenyls, alkynyls, hydroxyl, amino, nitro, thio amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R_2'$, $R_{40}$, and $R_{41}$ substituent taken together can form a bridging substituent; with the proviso that at least one of $R_1$, $R'_1$ and $R_{41}$ forms a bridging substituent with at least one of $R_2$, $R'_2$ and $R_{40}$ in order to provide $C_1$ and $C_2$ as a tetradentate; $R_7$ represents an aryl, a cycloalkyl, a cycloalkenyl, a heterocycle or a polycycle, and m is an integer in the range of 0 to 8 inclusive.

While the actual substituents of $C_1$ and $C_2$ can vary widely as necessary for a particular reaction scheme, one important proviso is that at least one substituent of $C_1$ must form a covalent bond with at least one substituent of $C_2$ in order to provide a tetradentate ligand which forms a square complex with M. That is, the ligand is a bridged cycle or polycycle which includes $C_1$ and $C_2$. Furthermore, in order for the catalyst to be chiral, e.g., to be capable of catalyzing stereoselective reactions, $R_1$, $R_2$, $R'_1$, $R'_2$ and other substituents of $C_1$ and $C_2$ are selected such that the ligand is asymmetric, e.g. the ligand comprises chiral centers that ae not related by a plane or point of symmetry, and/or comprises an axis of asymmetry due to restricted rotation, helicity, molecular knotting, or the like.

In the general structure 100, M represents a transition metal of Group 3–12 or the lanthide series of the periodic table, though preferably a metal ion which is not in its highest oxidation state. In the most preferred embodiments, M will be selected from the group of late transition metals, e.g., from the Group 5–12 metals. Even more preferably, M will be Cr(III)or Co(III). Moreover, the metal can be coordinated with a counteranion or a nucleophile.

Exemplary catalysts of this class are comprised of ligands derived from, for example, salens, porphyrins, crown ethers, azacrown ethers, cyclams, phthalocyanines, and the like.

In a particularly preferred embodiment, the subject reactions use a chiral catalyst having a metal ion complexed via an imine of a chiral ligand, preferably a diimine bridge. Accordingly, such variants of structure 100 can be provided in embodiments wherein any one or more of the Lewis bases is an imine, with metallo-Schiff base forms of imines being highly preferred.

To further illustrate, a tetradentate catalyst useful in the subject method can be derived using chiral salen or salen-like ligands (hereinafter "salenates"). The asymmetric metallosalenate catalysts offer a distinct advantage over many other chiral tetradentate catalysts, such as the metalloporphyrinates described infra, in that the salenate ligand can have stereogenic centers located just two bond lengths away from the metal. This proximity of the chiral centers to the reactive site can yield a high degree of stereoselectivity.

As disclosed herein, salen complexes are highly effective catalysts for the enantioselective ring-opening of epoxides and other cyclic compounds with nucleophiles, including water, alcohols, and thiols. This reaction is notable not only for its high enantioselectivity and for the utility of its products, but also for its remarkable efficiency as a catalytic process.

Moreover, the synthesis of chiral salenates is well characterized in the art, with more than 150 different chiral metallosalenates having been reported in the literature (for a review, see: Collman et al. (1993) *Science* 261:1404–1411). These ligands are easily and inexpensively synthesized on large scale starting from readily available materials, as described in Larrow et al., *J Org Chem* (1994) 59:1939–1942. Importantly, the general familiarity and ease of synthesis of metallosalenates permits the substituents to be readily varied in a systematic fashion in order to adjust the steric or electronic characteristics of the ligand. This feature makes possible the synthesis of ligands which are optimized for particular types of transformations and/or substrates. It has been found that such steric and electronic "tuning" of the ligands, and hence the catalysts, can have significant effects on the yield and e.e. of products formed in asymmetric reactions (described infra). In particular, the use of bulky blocking substituents is desirable to achieve high product e.e. in the asymmetric ring opening reaction. Furthermore, the stereogenic moiety can easily be modified to improve enantioselectivity.

In general, the salenate ligands which are useful in the subject method as chiral metallosalenate catalysts can be characterized as two substituted β-iminocarbonyls which are linked to form a tetradentate ligand having at least one stereogenic center. In an exemplary embodiment, a metallosalenate catalyst useful in the asymmetric ring-opening processes of the present invention can be represented by a metal complex with two substituted β-iminocarbonyls having general formula 102:

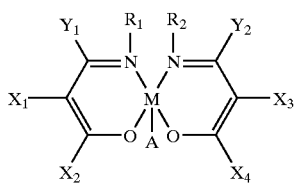

102 in which
the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$, and $X_2$ representing different ends of a single substituent, with the proviso that at least one of $R_1$, $Y_1$, $X_1$ and $X_2$ is covalently bonded to at least one of $R_2$, $Y_2$, $X_3$ and $X_4$ to provide the β-iminocarbonyls as a tetradentate ligand;

$R_7$ represents an aryl, a cycloalkyl, a cycloalkenyl, a heterocycle, or a polycycle;

m is an integer in the range of 0 to 8 inclusive;

M represents a transition metal; and

A represents a counterion or a nucleophile;

wherein each of the substituents of the β-iminocarbonyls, e.g., $R_1$, $R_2$, $Y_1$, $Y_2$, $X_1$, $X_2$, $X_3$ and $X_4$, are selected such that the catalyst is asymmetric.

The choice of each of $R_1$, $R_2$, $Y_1$, $Y_2$, $X_1$, $X_2$, $X_3$ and $X_4$ is also dependent on electronic and steric considerations, e.g., the tuning of the catalyst for a particular set of substrate and nucleophile, as well as the reactivity of the nucleophile, and the solvent system in which the reaction is to be carried out.

The chirality of the salenate ligand may be the result of the presence of one or more chiral atoms (e.g. carbon, sulfur, phosphorus, or other atoms capable of chirality), or may be the result of an axis of asymmetry due to restricted rotation, helicity, molecular knotting or chiral metal complexation. In preferred embodiments, the chiral ligand has at least one chiral atom or axis of asymmetry due to restricted rotation. Further guidance respecting the particular choice of the substituents is set out herein.

In preferred embodiments, the choice of $R_1$, $R_2$, $X_1$, $X_2$, $X_3$ and $X_4$ yield a class of chiral catalysts which are represented by the general formula

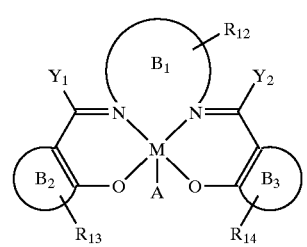

104 in which the $B_1$ moiety represents a diimine bridge, e.g. a bridging substituent which links the imino nitrogens of each β-iminocarbonyl, and preferably contains at least one chiral center of the salen ligand. For example, $B_1$, taken together with the metal-coordinating imines of the β-iminocarbonyl, can represent the diimine of an alkyl, an alkenyl, an alkynyl, or the diimine of —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfur, a sulfonyl, a selenium, or an ester; each of $B_2$ and $B_3$ independently represent rings selected from a group consisting of cycloalkyls, cycloalkenyls, aryls, and heterocycles, which rings comprise from 4 to 8 atoms in a ring structure. The substituents $R_{12}$, $R_{13}$ and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$ (the substituent R$_{12}$ occurring on one or more positions of —R$_{15}$—R$_{16}$—R$_{17}$—). Moreover, any two or more of the R$_{12}$, R$_{13}$, R$_{14}$, Y$_1$ and Y$_2$ substituted taken together can form bridging substituents to bridge the two β-iminocarbonyls and/or bridge different portions of the same β-iminocarbonyl. As above, in order to provide for a chiral catalyst, the choice of B$_2$ and B$_3$ (including their substituents) and/or the choice of substituents on B$_1$ (e.g., B$_1$ has a stereogenic center) is made to establish a chiral ligand. A represents a counteranion or a nucleophile.

In particular, as described in the appended examples, the salenate ligand can be derived from condensation of a substituted salicylaldehyde with a substituted diamine, preferably one stereoisomer of a chiral diamine, and then reacted with a desired metal to form a salen (N,N'-bis(salicylideneamino)alkyl) metal complex. An exemplary reaction for generating the salen ligand is based on Zhang and Jacobsen (1991) *J Org Chem* 56:2296–2298, and Jacobsen et al. PCT WO93/03838, and comprises.

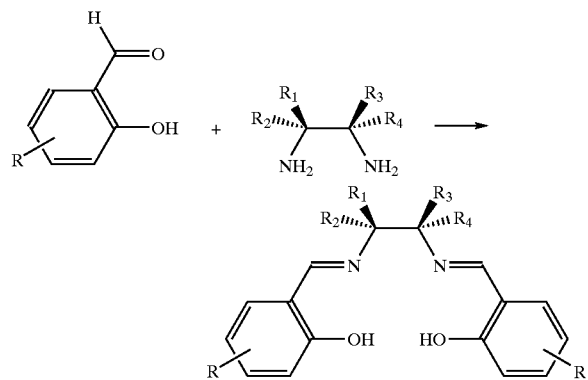

Utilizing this reaction scheme and others generally known in the art can provide a class of salens represented by the general formula:

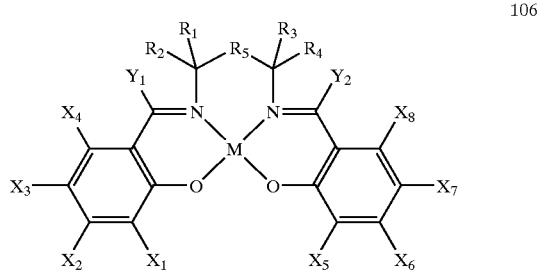

in which
each of the substituents R$_1$, R$_2$, R$_3$, R$_4$, R$_5$, Y$_1$, Y$_2$, X$_1$, X$_2$, X$_3$, X$_4$, X$_5$, X$_6$, X$_7$, and X$_8$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_7$;
or any two or more of the substituents taken together form a carbocycle or heterocycle having at least 4 atoms in the ring structure;

R$_7$ represents an aryl, a cycloalkyl, a cycloalkenyl, a heterocycle or a polycycle;

m is zero or an integer in the range of 1 to 8; and
M represents a transition metal;
wherein
if R$_5$ is absent, at least one of R$_1$ and R$_2$ is covalently bonded to at least one of R$_3$ and R$_4$; and the substituents of the salenate ligand are selected such that the salenate has at least one stereogenic center, e.g., is asymmetric. Moreover, the metal can be coordinated with a counteranion or a nucleophile.

With respect to generating a chiral ligand, it is important to note when selecting particular substituents that the salenate ligand has a potential catalytic site on both "sides" of the catalyst, e.g., relative to the plane of the four coordinating atoms of the ligand. Accordingly, when selecting the appropriate substituents for the β-iminocarbonyls in the above embodiments, it is important that either (1) both sides of the catalyst have stereogenic centers which effect identical stereoselectivity; or (2) the side having a stereogenic center of appropriate stereoselectivity is accessible while the other side has a blocking structure which substantially impairs approach to the metal atom from that side.

The first of the above options is preferred. In other words, it is preferred to have at least one stereogenic center on each side of the salenate ligand, each having the same R/S configuration. For example, (R,R)-1,2-Diphenyl-1,2-bis(3-tert-butylsalicylideamino)ethane, described in Example 1, contains two stereogenic centers on the diimine bridge which give rise to identical stereoselective faces on each side of the catalyst. This bis-faced catalyst has the advantage of not being susceptible to "leakage" reactions because substrate approach, albeit constrained, may occur from either face without loss of selectivity.

In contrast, control of the reactivity of the mono-faced catalyst can be accomplished by sterically hindering substrate approach to the undesired face. For instance, the salenate (R)-2-phenyl-1,2-bis(3-tert-butylsalicylideamino)ethane, e.g., formula 106 wherein R$_1$, R$_2$ and R$_3$ are protons, and R$_4$ is a phenyl, has two non-equivalent faces in terms of enantioselectivity. Accordingly, derivatizing the salenate ligand with a group which blocks access to the "free" face (e.g., the face having both a C1 and C2 proton of the diimine) can establish the ligand as a chiral catalyst with one enantiotopic face. For instance, a "picnic basket" form of the ligand can be generated wherein the phenyl moiety of the diimine bridge is on the "frontside" of the catalyst, and X$_4$ and X$_8$ are covalently linked to form a bridge on the "backside" of the catalyst, which bridge substitution precludes access to the metal ion from the backside. Those skilled in the art will recognize other single- and double-sided embodiments (see, for example, Collman et al. (1993) *Science* 261:1404).

The synthesis schemes for metallosalenates which may be useful in the present method, or precursors thereof, can be adapted from the literature. For example, see Zhang et al. (1990) *J Am Chem Soc* 112:2801; Zhang et al. (1991) *J Org Chem* 56:2296; Jacobsen et al. (1991) *J Am Chem Soc* 113:7063; Jacobsen et al. (1991) *J Am Chem Soc* 113:6703; Lee et al. (1991) *Tetrahedron Lett* 32:5055; Jacobsen, E. N. In *Catalytic Asymmetric Synthesis*, Ojima, I., Ed., VCH: New York, 1993, chapter 4.2; E. N. Jacobsen PCT Publications WO81/14694 and WO93/03838; Larrow et al. (1994) *J Am Chem Soc* 116:12129; Larrow et al. (1994) *J Org Chem* 59:1939; Irie et al. (1990) *Tetrahedron Lett* 31:7345; Irie et al. (1991) *Synlett* 265; Irie et al. (1991) *Tetrahedron Lett* 32:1056; Irie et al. (1991) *Tetrahedron Asymmetry* 2:481; Katsuki et al. U.S. Pat. No. 5,352,814; Coltman et al. (1993) *Science* 261:1404; Sasaki et al. (1994) *Tetrahedron*

50:11827; Palucki et al. (1992) *Tetrahedron Lett* 33:7111; and Srinivasan et al. (1986) *J Am Chem Soc* 108:2309. Exemplary salenate ligands described in the above references are illustrated below, as well as in the appended examples. Ph=phenyl, tBu=t-butyl.

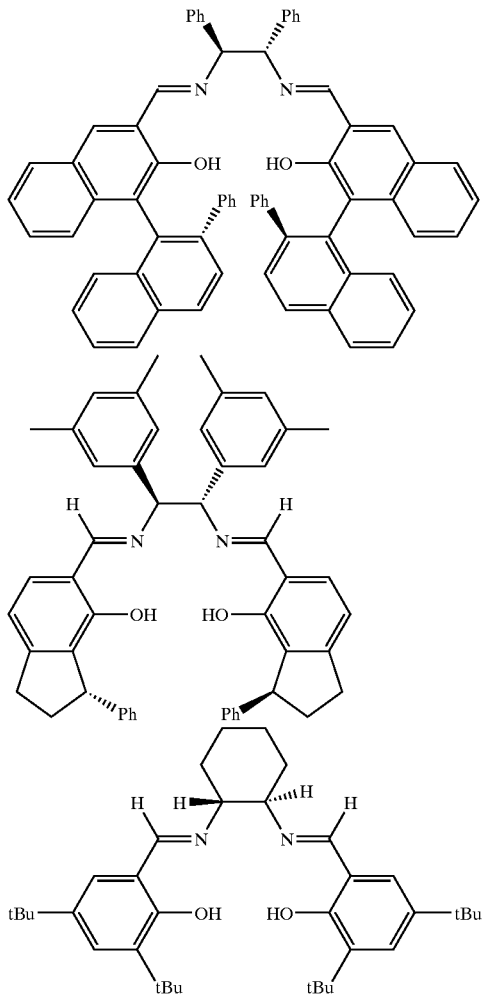

In yet another embodiment of the subject method, the tetradentate catalyst of general formula 100 is derived as a chiral tetradentate ligand represented, with the metal atom, by general formula 108:

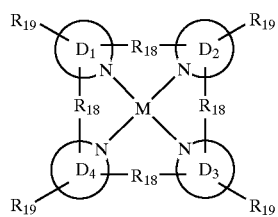

in which

D$_1$, D$_2$, D$_3$ and D$_4$ each represent heterocycles, such as pyrrole, pyrrolidine, pyridine, piperidine, imidazole, pyrazine, or the like;

each R$_{18}$ occurring in the structure represents a bridging substituent which links adjacent heterocycles, and preferably contains at least one stereogenic center of the ligard. For example, each R$_{18}$, represents an alkyl, an alkenyl, an alkynyl, or —R$_{15}$—R$_{16}$—R$_{17}$—, wherein R$_{15}$ and R$_{17}$ each independently are absent or represent an alkyl, an alkenyl, or an alkynyl, and R$_{16}$ is absent or represents an amine, an imine, an amide, a phosphonate, a phosphine, a carbonyl, a carboxyl, a silyl, an oxygen, a sulfonyl, a sulfer, a selenium, or an ester;

each R$_{19}$, independently, is absent or represents one or more substituents of the heterocycle to which it is attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, and —(CH$_2$)$_m$—R$_7$;

or any two or more of the R$_{18}$ and R$_{19}$ substituents are covalently linked to form a bridge substitution;

R$_7$ represents an aryl, a cycloalkyl, a cycloalkenyl, a heterocycle or a polycycle;

m is an integer in the range of 0 to 8 inclusive, and

M represents a transition metal, wherein each of the substituents R$_{18}$ and R$_{19}$ are selected such that the catalyst is asymmetric, e.g., the catalyst contains at least one stereogenic center. The metal will generally be coordinated with a counteranion or a nucleophile;

In preferred embodiments, D$_1$–D$_4$ are substituted pyrroles, and the catalyst is a chiral porphyrin or porphyrin-like ligand (hereinafter "porphyrinates"). As with the salenate ligands above, the synthesis of a vast number of porphyrinates has been reported in the literature. In general, most chiral porphyrins have been prepared in three ways. The most common approach involves attaching chiral units to preformed porphyrins such as amino- or hydroxy-substituted porphyrin derivatives (Groves et al. (1983) *J Am Chem Soc* 105:5791). Alternatively, chiral substituents can be introduced at the porphyrin-forming stage by allowing chiral aldehydes to condense with pyrrole (O'Malley et al. (1989) *J Am Chem Soc* 111:9116). Chiral porphyrins can also be prepared without the attachment of chiral groups. Similar to the bridged enantiotopic faces described for the salenates above, bridged porphyrinates can be generated by cross-linking adjacent and/or opposite pyrrolic positions and then separating the resulting mono-faced enantiomers with preparative HPLC using a chiral stationary phase (Konishi et al. (1992) *J Am Chem Soc* 114:1313). Ultimately, as with the generation of chiral salenate ligands, the resulting porphyrinate must have no internal plane, or point, of symmetry in order to be chiral.

With reference to formula 100, it will be understood that metalloporphyrinate catalysts, in addition to being represented by formula 108, can be represented generally by the compound of formula 100 when each of Z$_1$, Z$_2$, Z$_3$ and Z$_4$ represent nitrogen, and C$_1$ and C$_2$ along with their substituents (including R$_1$, R'$_1$, R$_2$, R'$_2$) form four substituted pyrrole rings which include Z$_1$, Z$_2$, Z$_3$ and Z$_4$. To complete the square tetradentate ligand, each pyrrole ring is covalently attached to the two adjacent pyrrole rings.

In preferred embodiments, the metalloporphyrinate catalyst is represented by general formula 110:

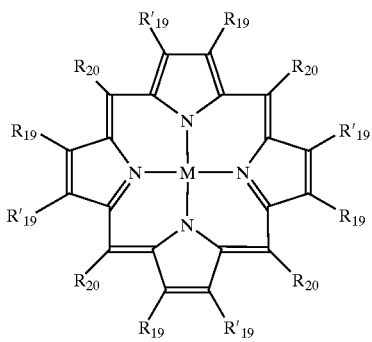

in which each $R_{20}$ occurring in structure 110, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

each $R_{19}$ and $R'_{19}$ occurring in structure 110, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two $R_{19}$ and $R'_{19}$ substituents on the same pyrrole can be taken together to form a fused carbocycle or fused heterocycle having from 4 to 7 atoms in the ring structure;

or any two or more of the $R_{19}$, $R'_{19}$ and $R_{20}$ substituents are covalently cross-linked to form a bridging substituent;

$R_7$ represents an aryl, a cycloalkyl, a cycloalkenyl, a heterocycle or a polycycle;

m is an integer in the range of 0 to 8 inclusive; and

M represents a transition metal, wherein the substituents $R_{19}$, $R'_{19}$ and $R_{20}$ are selected such that the catalyst is asymmetric, e.g. has at least one stereogenic center. The metal will generally be coordinated with a counteranion or a nucleophile.

As with the salenate ligands previously described, it is possible to sterically and electronically "tune" the porphyrin ligands to optimize reaction yield and e.e. Examples of suitable porphyrin ligands and synthesis schemes can be adapted from the art. For example, see Chang et al. (1979) *J Am Chem Soc* 101:3413; Groves et al. (1989) *J Am Chem Soc* 111:8537; Groves et al. (1990) *J Org Chem* 55:3628; Mansuy et al. (1985) *J Chem Soc Chem Commun* p155; Nauta et al. (1991) *J Am Chem Soc* 113:6865; Collman et al. (1993) *J Am Chem Soc* 115:3834; and Kruper et al. (1995) *J Org Chem* 60:725.

Still another class of the tetradentate catalysts represented by the general formula 100 and which are useful in the present asymmetric synthesis reactions can be represented by formula 112:

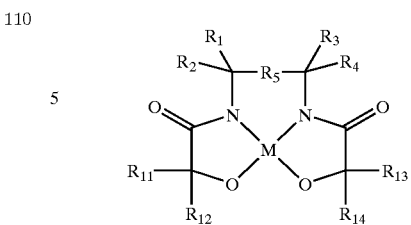

in which each of the substituents $R_1$, $R_2$, $R_3$, $R_4$, $R_5$, $R_{11}$, $R_{12}$, $R_{13}$ and $R_{14}$, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle having at least 4 atoms in the ring structure;

$R_7$ represents an aryl, a cycloalkyl, a cycloalkenyl, a heterocycle or a polycycle;

m is an integer in the range of 0 to 8 inclusive; and

M represents a transition metal, wherein if $R_5$ is absent, at least one of $R_1$ and $R_2$ is covalently bonded to at least one of $R_3$ and $R_4$, and the substituents are selected such that the catalyst is asymmetric. The metal will generally be coordinated with a counteranion or a nucleophile.

Exemplary catalysts of formula 112 include:

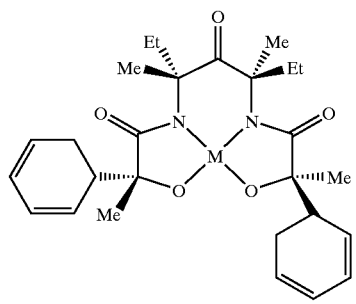

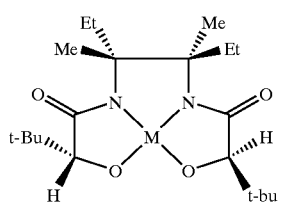

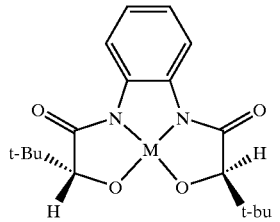

The synthesis of these and other related catalyst can be adapted from the literature. See, for example: Ozaki et al. (1990) *J Chem Soc Perkin Trans*2:353; Collins et al. (1986) *J Am Chem Soc* 108:2088; and Brewer et al. (1988) *J Am Chem Soc* 110:423.

In yet another embodiment, the tetradentate catalysts of formula 100 can be chosen from the class of azamacrocycle having a ligand represented by general formula 114:

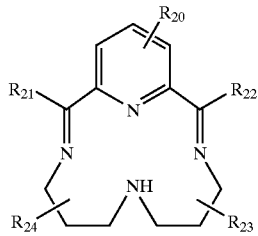

114 wherein

R$_{21}$ and R$_{22}$ each represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

R$_{20}$ is absent or represents one or more substituents of the pyridine to which it is attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

R$_{23}$ and R$_{24}$ each independently are absent or represent one or more substituents of the 1,3-diiminopropyl to which they are attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$;

or any two or more of the R$_{20}$, R$_{21}$, R$_{22}$, R$_{23}$ and R$_{24}$ substituents are covalently linked to form a bridging substituent;

R$_7$ represents an aryl, a cycloalkyl, a cycloalkenyl, a heterocycle or a polycycle; and m is an integer in the range of 0 to 8 inclusive, wherein the substituents R$_{20}$, R$_{21}$, R$_{22}$, R$_{23}$ and R$_{24}$ are selected such that the catalyst is asymmetric.

One advantage to this class of tetradentate catalysts, like the salenates, derives from the fact that the ligand provides a metallo-shiff base complex. Furthermore, stereogenic centers can be sited within two bond lengths of the metal center. Exemplary ligands of formula 114 include:

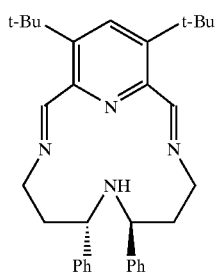

-continued

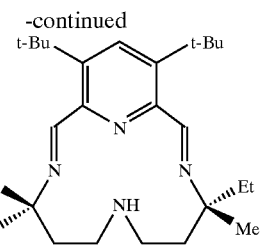

The synthesis of these and other embodiments of 114 are described in Prince et al. (1974) *Inorg Chim Acta* 9:51–54, and references cited therein.

Yet another class of tetradentate ligands of the subject method are the cyclams, such as represented by the general formula 116:

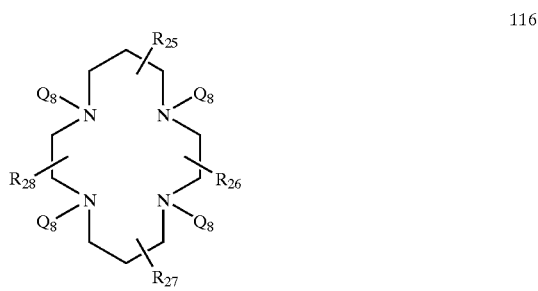

116 in which each of the substituents Q$_8$ independently, are absent or represent hydrogen or a lower alkyl, and each of R$_{25}$, R$_{26}$, R$_{27}$ and R$_{28}$, independently, represent one or more substituents on the ethyl or propyl diimine to which they are attached, which substituents are selected from the group of hydrogen, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, and —(CH$_2$)$_m$—R$_7$; or any two or more of the substituents taken together form a bridging substituent; R$_7$ represents an aryl, a cycloalkyl, a cycloalkenyl, a heterocycle, or a polycycle; and m is an integer in the range of 0 to 8 inclusive. Wherein the substituents are selected such that the catalyst is asymmetric. Exemplary embodiments and synthesis schemes for chiral cyclams useful in the present invention can be adapted from the art. See, for example, the Burrows et al. U.S. Pat. No. 5,126,464, Kimura et al. (1984) *Inorg Chem* 23:4181; Kimura et al. (1984) *J Am Chem Soc* 106: 5497; Kushi et al. (1985) *J Chem Soc Chem Commun* 216; Machida et al. (1986) *Inorg Chem* 25:3461; Kimura et al. (1988) *J Am Chem Soc* 110:3679; and Tabushi et al. (1977) *Tetrahedron Lett* 18:1049.

B. Chiral Tridentate Catalysts

In yet another embodiment of the subject method, the chiral catalyst which is provided in the reaction is from a class of chiral catalyst having a tridentate ligand which coordinates a transition metal in a substantially planar geometry, though as above some distortion to this geometry is contemplated. Accordingly, this planar geometry refers to tridentate ligands in which the Lewis basic atoms lie substantially in the same plane, with the metal also in that plane, or slightly above or below that plane.

Preferred tridentate catalysts; which may be employed in the subject reactions can be represented by the general formula 140:

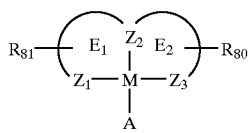

wherein $Z_1$, $Z_2$, and $Z_3$ each represent a Lewis base, such as selected from the group consisting of nitrogen, oxygen, phosphorus, arsenic and sulfur; the $E_1$ moiety, taken with $Z_1$, $Z_2$ and M, and the $E_2$ moiety, taken with $Z_2$, $Z_3$ and M, each, independently, form heterocycles; $R_{80}$ and $R_{81}$ each independently are absent, or represent one or more covalent substitutions of $E_1$ and $E_2$ with an organic or inorganic substituent permitted by valence requirements of the ring atom to which it is attached, or any two or more of the $R_{80}$ and $R_{81}$ substituents taken together form a bridging substituent; and M represents a transition metal, wherein each $R_1$, $R_2$, $R'_1$, $R'_2$ $R_{80}$ and $R_{81}$ substituents are selected to provide at least one stereogenic center in said tridentate ligand. In preferred embodiments, each $R_{80}$ and $R_{81}$ occurring in 140 independently represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is an integer in the range of 0 to 8 inclusive. The metal will generally be coordinated with a counteranion or a nucleophile.

For example, a chiral tridentate catalyst useful in the subject stereoselective reactions can have a ligand represented by general formulas 142 and 144:

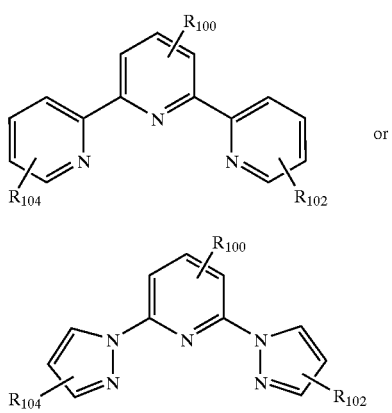

wherein each of $R_{100}$, $R_{102}$ and $R_{104}$ each independently are absent, or represent one or more covalent substitutions of heterocycle to which it is attached, or any two or more of the substituents taken together form a bridging substituent; wherein each $R_{100}$, $R_{102}$ and $R_{104}$ substituents, if present, can be selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is an integer in the range of 0 to 8 inclusive. Again, the substitution of 142 is intended to provide at least one stereogenic center in the tridentate ligand. Exemplary embodiments of the 2,2':6',2"-terpyridine ligands 142 and their synthesis can be adapted from, for example, Potts et al. (1987) *J Am Chem Soc* 109:3961; Hadda et al. (1988) *Polyhedron* 7:575; Potts et al. (1985) *Org Synth* 66:189; and Constable et al. (1988) *Inorg Chim Acta* 141:201. Exemplary 2,6-bis(N-pyrazolyl)pyridine ligands 144 can be adapted from, for example, Steel et al. (1983) *Inorg Chem* 22:1488; and Jameson et al. (1990) *J Org Chem* 55:4992.

Yet another class of planar tridentate catalyst useful in the subject stereoselective reactions can have a ligand represented by the general formula 146:

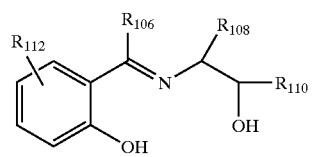

wherein each of $R_{106}$, $R_{108}$ and $R_{110}$ can be selected from the group consisting of hydrogens, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{112}$ is absent or represent one or more covalent substitutions of the heterocycle to which it is attached; or any two or more of the $R_{106}$, $R_{108}$, $R_{110}$ and $R_{112}$ substituents taken together form a bridging substituent; $R_7$ represents an aryl, a cycloalkyl, a cycloalkenyl, a heterocycle or a polycycle; and m is an integer in the range of 0 to 8 inclusive. The choice of substitution of 146 is intended to enhance its chirality. Exemplary embodiments of the salicylaldehyde-derived ligands 146 and their synthesis can be adapted from, for example, Desimoni et al. (1992) *Gazzetta Chimica Italiana* 122:269.

Still another class of planar tridentate catalyst useful in the subject stereoselective reactions can have a ligand represented by the general formula 148:

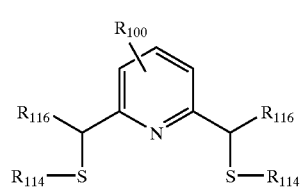

wherein $R_{100}$ is as described above, and each $R_{116}$ and $R_{114}$ can be selected from the group consisting of hydrogens, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents taken together form a bridging substituent; $R_7$ represents an aryl, a cycloalkyl, a cycloalkenyl, a heterocycle or a polycycle; and m is an integer in the range of 0 to 8 inclusive. The choice of substitution of 148 is intended to provide at least one stereogenic center in the tridentate ligand. Exemplary embodiments of the salicylaldehyde-derived ligands 148 and their synthesis can be adapted from, for example, Marangoni et al. (1993) *Polyhedron* 12:1669.

C. Tuning the Catalysts

The ligand substituents are chosen to optimize the selectivity of reaction and the catalyst's stability. The exact mechanism of action of the metallosalenate-catalyzed ring opening has not yet been precisely elucidated. However, the need for stereoselective nonbonded interactions between the substrate and catalyst is a feature of this and other chiral planar catalysts of the subject reaction which is believed to be comparable to the mechanism of olefin epoxidation by similar catalysts. While not wishing to be bound by any particular theory, it is believed that the present ring opening reactions involve two factors largely responsible for induction of asymmetry by formation of stereospecific nonbonded pairs of catalyst and substrate, namely, steric and electronic interactions between the incoming substrate and the ligand of the chiral catalyst. In general, "tuning" refers altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction. For instance, the choice of appropriate substituents as "blocking groups" enforces certain approach geometries and disfavors others.

Furthermore, the choice of substituent may also effect catalyst stability; in general, bulkier substituents are found to provide higher catalyst turnover numbers. It has been found that t-butyl groups (or other tertiary groups) are suitable bulky moieties for optimizing stereoselectivity and increasing catalyst turnover in the asymmetric epoxidation of olefins by (salen)Mn complexes.

A preferred embodiment for each of the embodiments described above provides a catalyst having a molecular weight less than 10,000 g/mol (a.m.u.), more preferably less than 5000 g/mol, and even more preferably less than 2500 g/mol. In another preferred embodiment, none of the substituents of the core ligand, or any molecule coordinated to the metal in addition to the ligand, have molecular weights in excess 1000 g/mol, more preferably they are less than 500 g/mol, and even more preferably, are less than 250 g/mol. The choice of substituent on the ligand can also be used to influence the solubility of the catalyst in a particular solvent system.

As mentioned briefly above, the choice of ligand substituents can also effect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl groups) on the ligand result in lower electron density of the ligand and metal center. The electron density of the ligand is important due to the possibility of interactions (such as π-stacking) with the substrate (see, e.g., Hamada et al. *Tetrahedron* (1994) 50:11827). The electron density at the metal center may influence the Lewis acidity of the metal or the nucleophilicity of a nucleophile coordinated to the metal. Choice of appropriate substituents thus makes possible the "tuning" of the reaction rate and the stereoselectivity of the reaction.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst, e.g. at a rate greater than conversion of the substrate. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen atom is to be joined to the substrate, a nitrogen nucleophile such as azide, ammonia, phthalimide, hydrazine or an amine may be employed. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Nucleophiles which introduce other atoms such as halides, selenium, or phosphorus, will be apparent.

In addition, carbon nucleophiles such as cyanide, acetylides, 1,3-dithiane anion, or stabilized carbanions such as enolates may be useful in the present invention.

For any of the above nucleophiles which exist as anions, the counterion can be any of a variety of conventional cations, including alkali and alkaline earth metal cations and ammonium cations. In some cases, non-ionic reagents may be useful; for example trimethylsilyl azide ($TMSN_3$) and trimethylsilyl cyanide (TMSCN) may be used to deliver the azide and cyanide nucleophiles, respectively.

Organometallic reagents such as simple or higher-order organocuprate or organozinc species may also be useful. In certain embodiments, Grignard reagents or organolithium reagents may be employed as nucleophiles.

In certain embodiments, the nucleophile may be part of the substrate, thus resulting in an intramolecular reaction.

In certain embodiments, the nucleophile may be a hydride, e.g., by use of sodium cyanoborohydride and the like.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain a reactive electrophilic center where a nucleophile may attack. The attack of the nucleophile will cause the breaking of a bond between the electrophilic atom and an atom of a leaving group, and the formation of a bond between the substrate and the nucleophile. It will further be understood that not all electrophiles will react with every nucleophile.

Most of the cyclic electrophiles contemplated for use in the methods of the present invention contain at least one ring having three to five atoms. Such small rings are frequently strained, making them susceptible to ring-opening by nucleophiles. However, in some embodiments a cyclic substrate may not be strained, and may have a larger electrophilic ring. Cyclic electrophiles which have good leaving groups (for example, cyclic sulfates) or which have $sp^2$ reactive centers (for example, carbonates or anhydrides) may have electrophilic rings with greater than 5 atoms, for example, from 6 to 9 atoms. Highly activated carbocycles such as certain substituted cyclopropanes (e.g., those substituted with electron-withdrawing groups) also are reactive toward ring-opening with nucleophiles and thus are contemplated for use in the methods of the invention. Furthermore, in certain embodiments it may be desired to use a substrate which has an allylic functionality which may be opened by attack at the allylic double bond in an "$S_N2'$-type" fashion.

Examples of suitable cyclic substrates which can be opened in the subject method include epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones, and the like.

In certain preferred embodiments, the cyclic substrate will be a meso compound. In other preferred embodiments, the cyclic substrate will be a chiral compound. In certain embodiments, the substrate will be a racemic mixture. In certain embodiments, the substrate will be a mixture of diastereomers.

In exemplary embodiments, a cyclic substrate suitable for use in the present invention has the following formula:

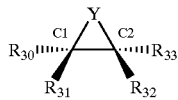

118 in which

Y represents O, S, N($R_{50}$), C($R_{52}$)($R_{54}$), or has the formula A-B-C; wherein $R_{50}$ is selected from the set comprising hydrogen, alkyls, acyls, carbonyl-substituted alkyls, carbonyl-substituted aryls, and sulfonyls; $R_{52}$ and $R_{54}$ each independently represent an electron-withdrawing group; A and C are independently absent, or represent a $C_1$–$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ can be any organic or inorganic substituent which forms a covalent bond with a carbon atom of 118, and which permits formation of the stable ring structure including Y. For instance, $R_{30}$, $R_{31}$, $R_{32}$, and $R_{33}$ can each independently represent hydrogen, a halogen, an alkyl, an alkenyl, an alkynyl, a hydroxyl, a nitro, a thiol, an amino, an amine, an imine, an amide, a phosphoryl, a phosphonate, a phosphine, a carbonyl, a carboxyl, a silyl, an ether, a thioether, a sulfonyl, a selenoether, a ketone, an aldehyde, an ester, or —(CH$_2$)$_m$—$R_7$;

or any two or more of the substituents $R_{30}$, $R_{31}$, $R_{32}$, and $R_{33}$ taken together form a carbocylic or heterocyclic ring having from 4 to 8 atoms in the ring structure;

$R_7$ represents an aryl, a cycloalkyl, a cycloalkenyl, a heterocycle or a polycycle; and m is an integer in the range of 0 to 8 inclusive.

In preferred embodiments, $R_{30}$, $R_{31}$, $R_{32}$, and $R_{33}$ are chosen such that the resulting compound has a plane of symmetry.

A leaving group is a functionality which upon bond cleavage departs with an electron pair. In general, good leaving groups are those moieties which are expelled from the substrate as weak bases. For example, sulfates, sulfonates, chloride, bromide, iodide, phosphates and the like are good leaving groups. In addition, some moieties may be good leaving groups when protonated or complexed with a Lewis acid. For example, alkoxide ions are generally poor leaving groups, but alcohols are good leaving groups. It should be noted that ring strain may, in some cases, allow a rather poor leaving group to be expelled, as in the case of epoxides, aziridines, and the like. Though not intended to be limiting, many compounds which have ring strain of more than 20 kcal/mole (compared to cyclohexane) will generally be suitable substrates.

In certain embodiments, the electrophilic atom may be a heteroatom.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are ran using mild conditions which will not adversely effect the substrate, the catalyst, or the product. For example, the reaction temperature influences the speed of the reaction, as well as the stability of the reactants, products, and catalyst. The reactions will usually be run at temperatures in the range of –78° C. to 100° C., more preferably in the range –20° C. to 50° C. and still more preferably in the range –20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrates under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, ring-opening by the cyanide nucleophile may be performed under an atmosphere of HCN gas. Similarly, in embodiments in which the ring-expansion of an epoxide by carbon dioxide or a similar reaction is desired, the reaction may be performed under an atmosphere of carbon dioxide, or a mixture of carbon dioxide and other gases. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, derivativation with one or more of substituents of the ligand. The immobilized ligands can be complexed with the desired metal to form the chiral metallocatalyst. The catalyst, particularly, an "aged" catalyst, is easily recovered after the reaction as, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

Example 1

Preparation of (R,R)-1,2-Diphenyl-1,2-bis(3-tert-butylsalicylideamino)ethane

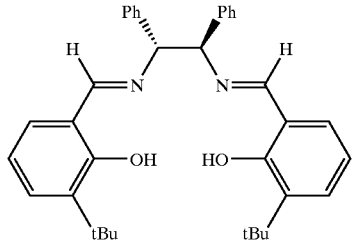

A solution of 360.5 mg (2.0 mmol) of 3-tert-butylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Recrystallization from MeOH/H$_2$O gave 485.8 mg (91%) of yellow powder, mp 73–74° C. $^1$H NMR (CDCl$_3$) δ 1.42 (s, 18H, CH$_3$), 4.72 (s, 2H, CHN=C), 6.67–7.27 (m, 16H, ArH), 8.35 (s, 2H, CH=N), 13.79 (s, 2H, ArOH) ppm; $^{13}$C NMR (CDCl$_3$) δ 29.3, 34.8, 80.1, 117.8, 118.5, 127.5, 128.0, 128.3, 129.6, 130.1, 137.1, 139.5, 160.2, 166.8 ppm. Anal. Calcd. for C$_{36}$H$_{40}$N$_2$O$_2$. C, 81.17; H, 7.57; N, 5.26. Found: C, 81.17; H, 7.60; N, 5.25.

Example 2

Preparation of (R,R)-1,2-Diphenyl-1,2-bis(3-diphenylmethylsilylsalicylideamino)ethane

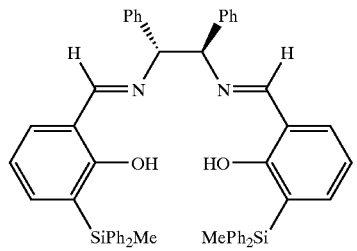

3-(Diphenylmethylsilyl)salicylaldehyde was prepared from 2-bromophenol in 5 steps according to established procedures. A solution of 348.3 mg (1.09 mmol) of 3-(diphenylmethylsilyl)salicylaldehyde and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR (CDCl$_3$) δ 0.95 (s, 3H), 4.68 (s, 2H), 6.72–7.55 (m, 36H, ArH), 8.37 (s, 2H), 13.34 (s, 2H) ppm.

Example 3

Preparation of 2,2'-Bis(3-tert-Butylsalicylideamino)-1,1'-Binaphthyl

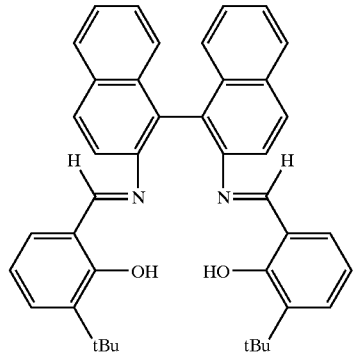

A solution of 725 mg (4.0 mmol) of 3-tert-butylsalicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and then volatile materials were removed under vacuum. The residue was purified by flash chromatography on 80 g $SiO_2$, using 20% $CH_2Cl_2$ in hexane as eluent. The mobile yellow fraction was collected and solvents were removed under vacuum to give 725 mg (1.20 mmol, 59% yield) of the diimine as a yellow powder.

Example 4

Preparation of (S,S)-1,2,-bis(3,5-di-tert-butylsalicylide-amino)cyclohexane (2)

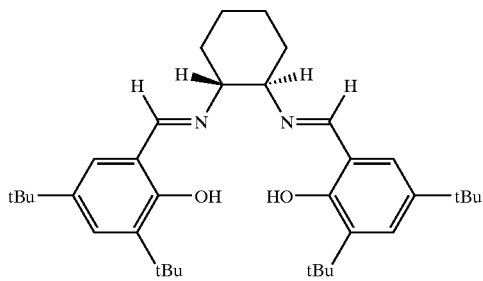

3,5-Di-t-butylsalicylaldehyde (2.0 equivalents) (prepared from the inexpensive, commercially available 2,4-di-t-butylphenol according to Larrow, J. F.; Jacobsen, E. N.; Gao, Y.; Hong, Y.; Nie, X.; Zepp, C. M. *J Org Chem* 1994, 59, 1939) was added as a solid to a 0.2 M solution of (S,S)-1,2-diaminocyclohexane (1.0 equivalent) (Aldrich Chemical Co., Milwaukee, Wis.) in absolute ethanol. The mixture was heated to reflux for 1 hr. and then $H_2O$ was added dropwise to the cooled bright yellow solution. The resulting yellow crystalline solid was collected by filtration and washed with a small portion of 95% ethanol. The yield of analytically pure salen ligand 2 obtained in this manner was 90–97%.

Spectroscopic and analytical data for the salen ligand: $^1H$ NMR ($CDCl_3$) δ 13.72 (s, 1H), 8.30 (S, 1H), 7.30 (d, J=2.3 Hz, 1H), 6.98 (d, J=2.3 Hz, 1H), 3.32 (m, 1H), 2.0–1.8 (m, 2H), 1.8–1.65 (m, 1H), 1.45 (m, 1H), 1.41 (s, 9H), 1.24 (s, 9H). $^{13}C$ NMR ($CDCl_3$): δ 165.8, 158.0, 139.8, 136.3, 126.0, 117.8, 72.4, 34.9, 33.0, 31.4, 29.4, 24.3. Anal. Calcd. for $C_{36}H_{54}N_2O_2$: C, 79.07; H, 9.95; N, 5.12. Found: C, 79.12; H, 9.97; N, 5.12.

Example 5

Preparation of (R,R)- and (S,S)-[1,2-bis(3,5-di-tert-butylsalicylideamino)cyclohexane]-manganese(III) chloride The salen ligand synthesized in Example 4 is redissolved in hot absolute ethanol to give a 0.1 M solution. Solid $Mn(OAc)_2 \cdot 4H_2O$ (2.5 equivalents) is added in one portion and the solution is refluxed for 1 hr. Approximately 5 equivalents of solid LiCl are then added and the mixture is heated to reflux for an additional 0.5 hr. Cooling the mixture to 0° C. and addition of a volume of water equal to the volume of the brown ethanolic solution affords the Mn(III) complex as a dark brown powder which is washed thoroughly with $H_2O$, and isolated by filtration in 81–93% yield. Acceptable C, H, N, Cl and Mn analyses of the catalyst have been obtained (±0.4%), but these vary according to the extent of water and ethanol incorporation in the powdery product. The solvent content of the catalyst does not influence its effectiveness.

Analytical data for this catalyst: Anal. Calcd for $C_{36}H_{52}ClMnN_2O_2 \cdot C_2H_5OH$: C, 67.19; H, 8.31; Cl, 5.22; Mn, 8.09; N, 4.12: Observed: C, 67.05; H, 8.34; Cl, 5.48; Mn, 8.31; N, 4.28.

Example 6

Preparation of (R,R)-[1,2-bis(3,5-di-tert-butylsalicylideamino)cyclohexane]-chromium(III) chloride (1)

The following procedure was found to provide 1 with reproducible catalytic activity. Under a nitrogen atmosphere, 0.309 g (2.52 mmol) of $CrCl_2$ (anhydrous, 99.9%, Alfa/Johnson Matthey) was added to the (R,R)-ligand 2 synthesized in Example 4 (1.25 g, 2.29 mmol) in dry, degassed THF (45 mL). The resulting dark brown solution was stirred under $N_2$ for 3 h and then in air for an additional 3 h. The solution was then diluted with 250 ml of t-butyl methyl ether and washed with satd. $NH_4Cl$ (3×150 ml) and brine (3×150 ml). The organic phase was dried ($Na_2SO_4$) and solvent was removed under reduced pressure, affording 1.41 g (87% yield) of 1 as a brown solid which was >98% pure as determined by HPLC analysis (octadecyl reverse phase, 100% $CH_3CN$). This material was used in the ring opening reactions without further purification. Recrystallization from acetonitrile provided high quality orange-brown crystals with 63% recovery: mp 375–398° C. (dec). IR (KBr, $cm^{-1}$) 3610 (br), 3420 (br), 2951(s), 2866, 1619(s), 1531, 1434, 1390, 1321, 1255, 1170, 1030, 837, 785, 748, 563, 543. Anal. Calcd for $C_{38}H_{59}N_2O_4CrCl \cdot 1.3/2H_2O \cdot 1/2THF$: C, 65.64; H, 8.55; N, 4.03; Cr, 7.48; Cl, 5.10. Found: C, 65.72; H, 8.53; N, 4.04; Cr, 7.45; Cl, 5.15. MS (FD): m/z 631 ([M]+). HRMS (FAB): m/z calcd for $[C_{36}H_{52}N_2O_2Cr]+([1-Cl]+)$ 596.3418, found 596.3434. $\mu_{eff}$=397 $\mu_B$.

Conductance ($CH_3CN$, 0.0045M) 0.57 $\Omega^{-1}$ $cm^2$ $mol^{-1}$.

Example 7

Ring-Opening of Meso-Epoxides Catalyzed by Cr (Salen) Complexes

Metal complexes of the readily available chiral salen ligand 2 were screened as catalysts for the model reaction of cyclohexene oxide with $TMS-N_3$. Complexes of Al, Ti, and Mn each catalyzed the reaction, but the azido silylether product 4 was generated in racemic form. In contrast, the corresponding Cr complex 1 catalyzed ring-opening to generate 4 with up to >80% ee. In addition, trace amounts of the byproducts 5 and 6 were observed, in molar concentrations similar to the concentration of catalyst (2 mol %). The reaction could be carried out under a variety of reaction conditions and in a wide range of solvents, however highest enantioselectivities were obtained using ethereal solvents (t-butyl methyl ether, THF, $Et_2O$).

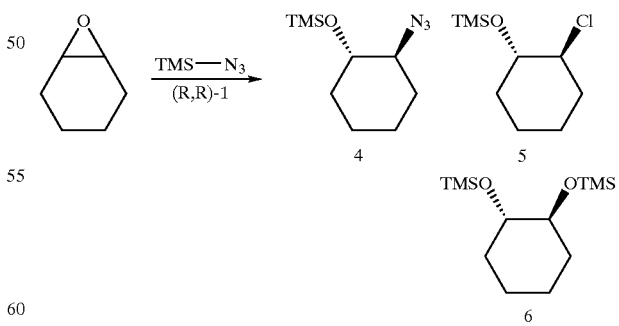

The reaction of a variety of meso epoxides with $Me_3SiN_3$ was screened with catalyst 1 (Table I) according to the following general procedure:

A 5 mL flask is charged with 42 mg (0.060 mmol) of 1 and 1.0 mL of $Et_2O$. The epoxide (3.00 mmol) is added and the mixture is stirred for 15 min, at which time Me₃SiN₃ (0.418 mL, 3.15 mmol) is added. The resulting brown solution is stirred at room temperature for the indicated time (Table I). The solution is then concentrated in vacuo and the residue is filtered through a 10 mL plug of silica gel with 100 mL of 5–20% EtOAc/hexanes. The filtrate is concentrated and the resulting residue is subjected to analysis by GC or HPLC to determine the enantiomeric composition of silylated azidoalcohol.

Desilylation: The product obtained as described above is dissolved in methanol (5 mL). (1S)-(+)-10-Camphorsulfonic acid (35 mg, 0.15 mmol) is added and the resulting solution is stirred for 30 min and then concentrated in vacuo. The residue is purified by flash chromatography to afford pure azidoalcohol.

Five-membered ring epoxides underwent ring-opening with very high levels of enantioselectivity, while 6-membered ring and acyclic epoxides afforded somewhat diminished selectivities. Ether, olefin, and carbonyl-containing functional groups were all tolerated (entries 2–4,7). Interestingly, 3,4-epoxytetrahydrofuran (entry 2) was one of the most reactive epoxides in this study, suggesting that Lewis bases do not inhibit catalytic activity.

TABLE I

Enantioselective opening of meso epoxides with 1.[a]

| entry | epoxide | time (h) | Isolated yield (%)[b] | ee (%)[c] |
|---|---|---|---|---|
| 1 | (cyclopentene oxide) | 28 | 80 | 94 |
| 2 | (3,4-epoxytetrahydrofuran) | 18 | 80 | 98 |
| 3 | (Fmoc-N bicyclic epoxide) | 36 | 80 | 95 |
| 4 | (F₃C-C(O)-N bicyclic epoxide) | 16 | 90 | 95 |
| 5 | (cyclopentanone epoxide) | 14 | 65 | 88 |
| 6 | (cyclohexene oxide) | 18 | 80 | 88 |
| 7 | (cyclohexadiene monoepoxide) | 46 | 72 | 81 |
| 8 | (2,3-dimethyl epoxide) | 30 | 65[d] | 82 |
| 9 | (EtO₂C cyclopentene epoxide) | 24 | 90 | 94 |
| 10 | (TBSO cyclopentene epoxide) | 24 | 93 | 96 |
| 11 | (bis-EtO₂C cyclopentene epoxide) | 24 | 75 | 94 |
| 12 | (TES cyclopentene epoxide) | 24 | 85 | 92 |
| 13 | (TES cyclopentene epoxide) | 24 | 88 | 96 |

[a]All reactions were run on 3.0 mmol scale of epoxide. Absolute configurations for the products from entries 1, 6 and 8 were determined as in H. Yamashita Bull Chem Soc Jpn (1988) 61:1213. The absolute configurations of the remaining products were assigned by analogy.
[b]Isolated yield of azido alcohol, unless noted otherwise.
[c]All ee's were determined by chiral chromatography.
[d]Isolated yield of the trimethylsilylether.

Example 8

Solvent-free Enantioselective Ring-opening Reactions

The enantioselectivity of the epoxide ring-opening reaction was found to be remarkably insensitive to the initial concentration of reagents. We therefore investigated solvent-free reactions in which, in principle, no reaction byproducts of any kind are generated (Table II). Thus, reaction of 5 mmol of cyclohexene oxide with 2 mol % catalyst 1 and 5.25 mmol (1.05 equiv) of TMSN₃ for 18 h, followed by short path distillation under reduced pressure, afforded an 86% yield of the TMS-protected azido alcohol in 84% e.e. (cycle 1). As expected, this product was contaminated with small amounts of ≦2% of each) of silylated chlorohydrin 5 and bis-silylated diol 6. Treatment of the residual catalyst with additional portions of cyclohexene oxide (5 mmol) and TMSN₃(5.25 mmol) resulted in an 88% yield of product (87% ee) that was completely free of any byproducts (cycle 2). An additional recycling of the catalyst gave the product in 91% yield and 88% ee (cycle 3). A fourth reaction was then performed with cyclopentene oxide and the corresponding product was obtained in 81% yield and 94% ee (cycle 4). Finally, 1,4-cyclohexadiene monoepoxide was used for the fifth cycle (75% yield, 83% ee; cycle 5). In all cases, complete conversion of the epoxide was observed at the times indicated.

TABLE II

Solvent-Free enantioselective Opening of Meso Epoxides with Trimethylsilylazide and Recycled Catalyst (R,R)-1[a]

R─△─O + 1. 2 mol % Cat., TMSN$_3$ / 2. Distillation → R─*N$_3$ / R─OTMS

| entry | epoxide | time (h) | Isolated yield (%)[b] | ee (%)[c] |
|---|---|---|---|---|
| 1 | cyclohexene oxide | 18 | 86 | 84 |
| 2 | cyclohexene oxide | 21 | 88 | 87 |
| 3 | cyclohexene oxide | 20 | 91 | 88 |
| 4 | cyclopentene oxide | 4 | 81 | 94 |
| 5 | cyclohexadiene oxide | 18 | 75 | 83 |

[a]All cycles were run with 5.00 μmol of epoxide and 5.25 mmol of TMSN$_3$
[b]Isolated yield of distilled TMS protected azidoalcohol.
[c]Determined by chiral GC.

Based on these results, the first reaction can be thought of as an "aging" of the catalyst. Consistent with the observation of silylated chlorohydrin 5 in the first reaction only, the "aged" catalyst contains no chlorine as judged by elemental analysis. This catalyst also displays an absorbance at 2058 cm$^{-1}$ in its infrared spectrum, consistent with a Cr—N$_3$ N=N stretch. We therefore conclude that the active catalyst is (salen) Cr—N$_3$. While not wishing to be bound by any particular theory, it appears that catalysis involves Lewis acid activation by the chromium center nucleophilic delivery of azide by a Cr—N$_3$ intermediate, or both. The apparent intermediacy of a Cr—N$_3$ intermediate provides circumstantial support for the latter.

Example 9

Kinetic Resolution of Chiral Racemic Epoxides

We have also investigated the use of catalyst 1 for the kinetic resolution of chiral racemic epoxides. Preliminary results are shown in Table III. Thus, treatment of 3 mmol of styrene oxide with 0.70 equiv. of TMSN$_3$ and 2 mol % of catalyst 1 resulted in 76% conversion (based on the available enantiomer) of the epoxide to a complex mixture of products. The ee of the unreacted styrene oxide was 98%. Similarly, epichlorohydrin proceeded to 80% conversion (based on the available enantiomer) when treated with 0.60 equiv of TMSN$_3$ and 2 mol % 1. The ee of the unreacted epichlorohydrin was 97%.

TABLE III

Trimethylsilylazide Catalyzed by (R,R)-1[a]

R─△─O + 1. Cat., TMSN$_3$ / 2. Et$_2$O → R─△─O

| epoxide | equiv TMSN$_3$ | time (h) | conv. (%)[b] | ee (%)[c] |
|---|---|---|---|---|
| styrene oxide | 0.70 | 67 | 76 | 98 (R) |
| epichlorohydrin | 0.60 | 21 | 80 | 98 (R) |

[a]All reactions were run with 3.00 mmol of epoxide, 0.060 mmol catalyst and the indicated amount of TMSN$_3$ in 1.0 mL Et$_2$O
[b]Determined by GC employing nonane as internal standard.
[c]Determineded by chiral GC.

As shown in Table III, the kinetic resolution of racemic epoxides can provide trimethylsilyl azidoalcohols, which can in turn be converted to 1-amino-2-ols. The overall process is efficient and procedes with high enantio- and regioselectivity, as shown in Table IV.

TABLE IV

Synthesis of 1-amino-2-ols via kinetic resolution of epoxides catalyzed by (R,R)-1

R─△─O → Cat., TMSN$_3$[a] → R─(OTMS)─N$_3$ + R─△─O → R─(OH)─NH$_2$

| epoxide | regioselectivity | ee (%)[c] |
|---|---|---|
| H$_3$C─△─O (propylene oxide) | >150:1 | 98 (R) |
| CH$_3$(CH$_2$)$_3$─△─O | 50:1 | 98 (R) |

[c]Reactions were run with 1 mol % catalyst and 0.5 equiv TMSN$_3$.

Example 10

Regioselective Ring Opening of Epoxides

The use of the catalyst 1 for selective opening of epoxides which have little inherent steric or electronic bias has also been investigated. The ring opening of a racemic epoxide occurs with little selectivity when an achiral catalyst is used, but ring-opening of the optically-enriched epoxide occurs with good regioselectivity in the presence of either enantiomer of the chiral catalyst.

Catalyst selection can also influence the regioselectivity of ring opening in more biased systems. For example the reaction of optically pure styrene epoxide with an achiral catalyst results in preferential nucleophile attack at the less-substituted carbon atom of the epoxide. This inherent regiochemical preference can be either enhanced or reversed by selection of the appropriate antipode of the chiral catalyst. Thus, the (R,R)-enantiomer of the catalyst 1 reverses the regioselectivity of nucleophile attack, while the (S,S)-enantiomer of catalyst 1 enhances the pre-existing regioselectivity of ring opening.

Example 11

Selective Ring Opening of Epoxides on Solid Support

To test chiral ring-opening reactions on substrates attached to a solid support, meso epoxides were immobilized on resin beads. The immobilized epoxides had the following structures:

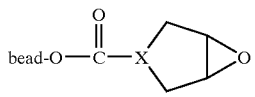

in which X represents —N, —OCH, or —OCH$_2$CH. Both diastereomers of the carbocyclic epoxides were used. The immobilized epoxides were treated with trimethylsilyl azide in ether in the presence of 20–50 mol % of chromium salen catalyst, and the reaction was allowed to proceed. The ring-opened compounds were released from the solid support by treatment with trifluoroacetic acid/trifluoroacetic anhydride in methylene chloride. The released products had the following structures:

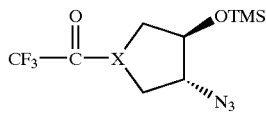

in which X is as described above. The ee of the released products was determined, and the results demonstrate that solid-supported meso epoxides can be ring-opened with excellent optical yields and conversion. Ee's ranged from 91–96% and yields were high.

Example 12

Regioselective Ring Opening of Epoxides with Oxygen and Sulfur Nucleophiles The ability of the salen catalysts to catalyze enantioselective ring-opening reactions with oxygen and sulfur nucleophiles has also been investigated. Cyclohexane epoxide (1,2-epoxycyclohexane) was treated with benzoic acid, methanol, or thiophenol in the presence of a (salen)Cr catalyst. The results are shown below:

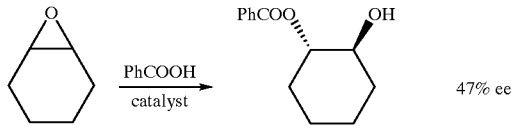

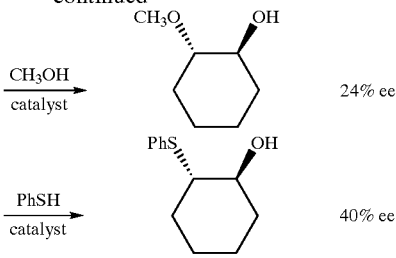

In each case, the reaction proceeded cleanly and with moderate enantioselectivity.

Example 13

Ring Expansion of Epoxides with Carbon Dioxide

The use of catalyst 1 for ring expansion of epoxides was investigated using 1,2-epoxyhexane as substrate, according the scheme below.

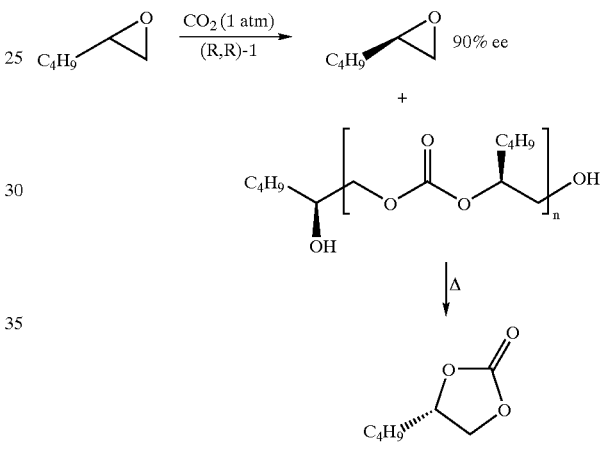

Under one atmosphere of carbon dioxide and in the presence of 1 mol % of catalyst (R,R)-1, racemic 1,2-epoxyhexane selectively underwent reaction. At 90% conversion, the unreacted starting epoxide was found to be enriched in the (R)-enantiomer (90% ee). The polycarbonate product is heated to effect ring closure and the resulting carbonate is analyzed and found to be optically active.

Example 14

Synthesis of Catalyst 200

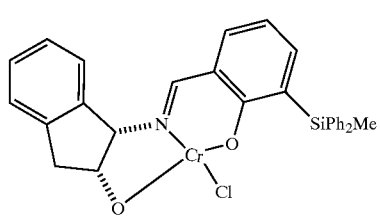

A tridentate catalyst was synthesized as descibed below. To a solution of (S,S)-1-amino-2-hydroxyindane (0.857 g, 5.75 mmol) in 60 ml EtOH was added 2-hydroxy-3-(methyldiphenylsilyl)benzaldehyde (1.829 g, 5.75 mmol)

under a nitrogen atmosphere. The resulting solution was refluxed under N$_2$ for 12 hours. The solution was then cooled to room temperature, and solvent was removed under reduced pressure. The concentrate was purified by recrystallization from hexane to give 2.15 g–2.46 g (83%-95 yield) of the corresponding (S,S)-imine.

In a dry Schlenk flask under a nitrogen atmosphere, (S,S)-imine (0.765 g, 1.7 mmol) was dissolved in dry THF (30 ml). 2,6-lutidine (0.730 g, 6.81 mmol, distilled over CaH$_2$) was added to the flask, followed by 0.638 g (1.70 mmol) chromium (III) chloride:tetrahydrofuran complex (1:3, 97%, Aldrich). The resulting dark brown solution was stirred under N$_2$ for 12 hours. The solution was then diluted with 200 ml of t-butyl methyl ether and washed with saturated NH$_4$Cl (4×150 ml) and brine (3×150 ml). The organic portion was dried over Na$_2$SO$_4$, and the solvent was removed under reduced pressure. Catalyst 200 (0.890 mg, 95% yield) was obtained as a dark brown solid.

In a dry Schlenk flask under a nitrogen atmosphere, 200 (0.653 g, 1.22 mmol) was dissolved in azidotrimethylsilane (3 ml). The reaction mixture was stirred under N$_2$ for 12 hours and was then concentrated under reduced pressure to remove excess azidotrimethylsilane and TMSCl, and the resulting (tridentate ligand)Cr—N$_3$ azide catalyst could be used without further purification.

Example 15

Aziridine Ring Opening with Catalyst 200

The ability of catalyst 200 to catalyze ring-opening of aziridines was tested in two different procedures. Aziridine 205 was used in all the ring-opening reactions of this Example.

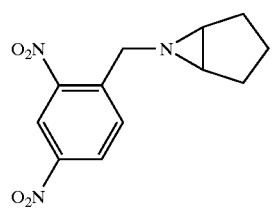

205

Procedure A: To a solution of 1.34 mg (0.0025 mmol) of catalyst 200 in 0.5 ml of acetone under N$_2$ was added aziridine 205 (13.2 mg, 0.05 mmol). The homogenous solution was stirred at room temperature under N$_2$ for 15 min. Azidotrimethylsilane (6.64 μl, 0.05 mmol) was added. Aliquots were taken at different time intervals to determine ee and conversion of the product. The reaction was normally done in 4 hours. The enantiomeric excess of the product was 67% and conversion was greater than 95%.

Procedure B: To a solution of 5.42 mg (0.001 mmol) of catalyst 200 in 0.5 ml of acetone under N$_2$ was added aziridine 205 (26.3 mg, 0.10 mmol). The homogenous solution was cooled to –20° C. under N$_2$. Azidotrimethylsilane (13.3 μl, 0.10 mmol) was added. The reaction mixture was stirred at –20° C. under N$_2$ for 21 hours and was then concentrated under reduced pressure to remove acetone. The residue was chromatographed on silica gel (elution with 15% ethyl acetate in hexane) to give 24.8 mg (81% yield) of the product with 82% ee. Enantiomeric excess was determined by Chiralpak AS column on HPLC.

The structures of tridentate ligands (1–8) that were comprised by additional (tridentate ligand)Cr catalysts tested in the aziridine opening reaction, and the enantiomeric excess of products obtained by treatment of aziridine 205 with these catalysts are shown below. In general, ee's were modest to good, and conversions were high.

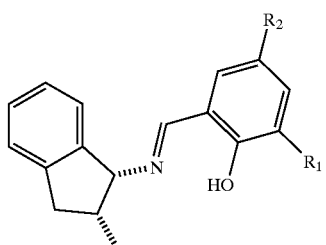

1 R$_1$ = R$_2$ = Cl
2 R$_1$ = R$_2$ = Br
3 R$_1$ = R$_2$ = NO$_2$
4 R$_1$ = tBu; R$_2$ = Br
5 R$_1$ = tBu; R$_2$ = OC(O)tBu
6 R$_1$ = tBu; R$_2$ = Me
7 R$_1$ = tBu; R$_2$ = OMe
8 R$_1$ = tBu; R$_2$ = OSiPh$_3$

| Catalyst | (1)Cr | (2)Cr | (3)Cr | (4)Cr | (5)Cr | (6)Cr | (7)Cr | (8)Cr |
|---|---|---|---|---|---|---|---|---|
| est. % conv. | >90 | >90 | >90 | >90 | >90 | >90 | >90 | >90 |
| % ee | 53 | 50 | 20 | 50 | 54 | 55 | 46 | 56 |

Example 16

Synthesis of (R)-4-((Trimethylsilyl)oxy)-2-cyclopentenone (214)

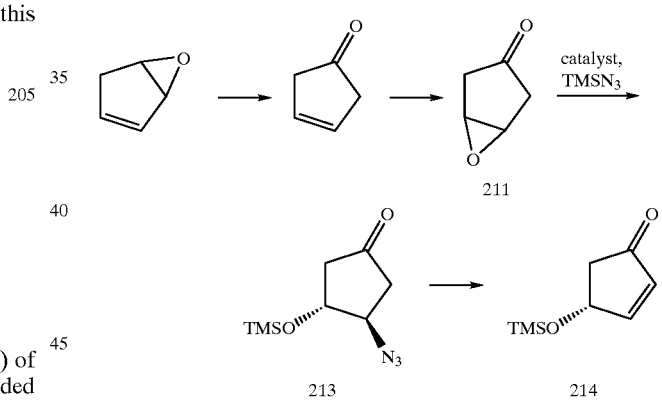

The three-component coupling method of Noyori (see, e.g., Noyori, R. "Asymmetric Catalysis in Organic Synthesis", Wiley, New York, 1994, pp. 298–322) is an effective means of synthesizing prostaglandins and related compounds. The central element, an O-protected (R)-4-hydroxy-2-cyclopentenone, is thus an important synthetic target. Asymmetric ring-opening of epoxides provides a potentially valuable synthetic route to this class of intermediates. A realization of this synthetic route is described below (for example, see: J. L. Leighton and E. N. Jacobsen, J. Org. Chem., (1996) 61:389–390).

The requisite epoxide 211 for the enantioselective ring-opening reaction was prepared according to the method of Noyori (Suzuki, M.; Oda Y., Noyori, R. J Am. Chem. Soc. 1979, 101, 1623–1625). Thus, 3-cyclopentenone was synthesized via the Pd(0)-catalyzed rearrangement of 3,4-epoxycyclopentene, a reaction remarkable both for the efficiency of catalysis and the ease of the experimental procedure. Epoxidation of 3-cyclopantenone was effected with trifluoroperacetic acid to afford 3,4-epoxycyclopentanone (211) in 60% isolated yield after distillation. We found that treatment of the trifluroacetic anhydride with hydrogen peroxide-urea addition compound provided a useful alternative to the literature method for the preparation of trifluoroperacetic acid Noyori's procedure for preparation of trifluoroperacetic acid specifies the use of 90% $H_2O_2$. Overall, this two-step sequence provided multigram quantities of epoxide 211 in pure form with no chromatographic purification necessary.

The asymmetric ring opening of epoxide 211 was effected using a (salen)$CrN_3$ complex (comprising salen ligand 2). This complex catalyzes the ring opening of epoxides by $TMSN_3$ with virtually the same enantioselectivity as the chloride complex 1; preliminary mechanistic studies indicate that 1 is in fact a precatalyst and that this complex is the active catalyst. (see supra, e.g., Example 8; and Martinez, L. E.; Leighton J. L., Carsten, D. H.; Jacobsen, E. N. *J. Am. Chem. Soc.* 1995, 117, 5897–5898). A distinct synthetic advantage to using this catalyst in catalytic ring-opening reactions is that the chloride addition side product observed using catalyst 1 is avoided. A one-pot synthesis of this azide complex can be accomplished by treatment of complex 1 with $AgClO_4$ in $CH_3CN$, followed by filtration to remove the AgCl, and treatment of the filtrate with $NaN_3$; permitting the isolation of the complex in. $\geq$90% yield.

Submission of epoxide 211 to the previously described ring-opening conditions (Martinez, L. E.; Leighton J. L., Carsten, D. H.; Jacobsen, E. N. *J. Am. Chem. Soc.* 1995, 117, 5897–5898) with the azide catalyst produced azido silyl ether 213, which was invariably contaminated with ~10% of 4-((trimethylsilyl)oxy)-2-cyclopentenone (214). Treatment of this mixture with basic alumina induced selective elimination of the azide to cleanly provide the desired enone (R)-214. However, HPLC analysis of this material ((R,R) Whelk-O, 97:3 hexane: 2-propanol, 1.0 mL/min) revealed an overall enantioselectivity of only 80%.

Reasoning that the enone side product 214 obtained in the epoxide ring-opening reaction might be due to non-enantioselective β-elimination from 212 followed by silylation of the resulting alcohol with $TMSN_3$, we examined several reaction parameters with the goal of suppressing this pathway and thus enhancing the enantioselectivity in the ultimate generation of 214. When the ring-opening reaction was run at −10° C. for 22 h and then warmed slowly to 10° C. over 3 h, 213 was obtained in ~90% yield, with only ~2% contamination by enone 214 as judged by $^1$H NMR analysis of the crude product mixture. Basic alumina-promoted azide elimination followed by distillation under reduced pressure then provided the desired enone 214 in 94% ee and in four steps from cyclopentadiene. As such, this asymmetric catalytic method represents an attractive alternative to existing enzyme-based procedures.

Chiral (salen)CrAzide Complex. A 200 mL round bottom flask fitted with a dropping funnel was charged with 2.18 g (10.5 mmol) of $AgClO_4$ and 30 mL of $CH_3CN$. The dropping funnel was charged with a solution of 6.75 g (10.0 mmol) of (salen)CrCl complex (S,S)-1 in 20 mL of $CH_3CN$. This solution was added over 5 min to the $AgClO_4$ solution. A precipitate began forming almost immediately. The heterogeneous brown mixture was stirred 16 h and then filtered through a pad of Celite with two 25 mL $CH_3CN$ washes. The filtrate was concentrated to a volume of ~30 mL. Solid $NaN_3$ (1.30 g, 20.0 mmol) was added, and the brown solution was stirred for 24 h during which time the mixture became heterogeneous. The reaction mixture was diluted with tert-butyl methyl ether (300 mL) and washed with $H_2O$ (3×300 mL). The organic phase was dried ($Na_2SO_4$), filtered, and concentrated to give 5.92% (90%) of (salen)$CrN_3$ as a brown powder. This material was used for the asymmetric ring opening of epoxides as described below.

For the purpose of characterization, an analytical sample of (salen)$CrN_3$ was prepared as follows. In a $N_2$-filled drybox, 1.0 g of (salen)$CrN_3$ prepared as described above was treated with $Et_2O$ (2.0 mL) and $TMSN_3$ (1.0 mL). The initially homogeneous mixture was stirred for 1 h, during which time a precipitate was deposited. The volatiles were removed in vacuo, and the resulting brown powder was placed in a fitted funnel and washed with $Et_2O$ (5×5 mL). The recovered solid material was dried in vacuo to give (salen)$CrN_3$ as a brown powder: IR (KBr) 2953, 2907, 2866, 2084, 1620, 1530, 1434, 1391, 1321, 1254, 1169, 837 cm$^{-1}$ Anal. (H. Kolbe; Ar/$V_2O_3$) Calcd for $C_{36}H_{52}CrN_5O_2$: C, 67.69; H. 8.20; N., 10.96; Cr. 8.14. Found C, 67.75, H, 8.16; N, 10.95; Cr. 8.08.

3,4-Epoxycyclopentanone (211). To a cooled (0° C.) suspension of $H_2O_2$-urea addition compound (9.27 g, 98.5 mmol) in $CH_2Cl_2$ (100 mL) was added 16.1 mL (23.9 g, 114 mmol) of trifluoroacetic anhydride over 3 min. The mixture was stirred 15 min during which time it became slightly cloudy and biphasic. A 1 L round bottom flask fitted with a dropping funnel was charged with 3-cyclopentenone (6.22 g, 75.8 mmol) in methylene chloride (160 mL). The solution was cooled to 0° C., and $NaHCO_3$ (20.7 g, 246 mmol) was added. The biphasic oxidant, solution was transferred to the dropping funnel and was added over 5 min to the 3-cyclopentenone solution. The resulting heterogeneous mixture was stirred for 15 min at 0° C. and then for 16 h at 23° C. The reaction was quenched by the addition of $Na_2S_2O_3$.5 $H_2O$ (20.7 g, 83.4 mmol) and $H_2O$ (300 mL), followed by vigorous stirring for 5 min. The layers were separated, and the aqueous layer was extracted with $CH_2Cl_2$ (150 mL). The combined organic layers were dried ($Na_2SO_4$), filtered and concentrated. Distillation of the residue (short path, ~250 mTorr, bp 46–50° C.) provided 4.43 g (60%) of epoxide 211 as an oil, which was used without further purification.

(R)-4-((Trimethylsilyl)oxy)-2-cyclopentenone (214). To a solution of epoxide 211 (1.30 g, 13.3 mmol) in $Et_2O$ (2.0 mL) was added (salen)$CrN_3$ (0.173 g, 0.266 mmol). After 5 min, the solution was cooled to −10° C. and $TMSN_3$, (1.86 mL, 1.61 g, 14.0 mmol) was added by syringe. The solution was stirred at −10° C. for 22 h and then allowed to warm to 10° C. over 3 h. The reaction mixture was concentrated, and the residue was filtered through a pad (~20 mL) of silica gel with 20:80 EtoAc/hexane (200 mL). The filtrate was concentrated to give azido silyl ether 213, contaminated with ~2% of 214 as judged by $^1$H NMR spectroscopy. Data for 213: $^1$H NMR (CDCl$_3$) δ 4.30 (m, 1H), 4.05 (m, 1H) 2.74–2.52 (m, 2H) 2.25–2.13 (m, 2H), 0.16 (5, 9H); $^{13}$C NMR (CDCl$_3$) δ 211.8, 73–4, 64.9, 45.6, 41.5, −0.2; IR (thin film) 2958, 2105, 1757, 1254, 1134, 1082, 879 cm$^{-1}$.

The azido silyl ether 213 obtained as described above was dissolved in $CH_2Cl_2$ (20 mL) and treated with 10 g of basic alumina (Fisher, Brockman activity 1). The slurry was stirred for 30 min and then filtered through a pad (~20 mL) of basic alumina with 150 mL of 95:5 $CH_2Cl_2$:EtOAc. The filtrate was concentrated, and purification of the residue by distillation (short path, ~250 mTorr, bp 54–55° C.) provided enone 214 as an oil which was >98% pure as determined by $^1$H NMR analysis (1.74 g, 77% overall yield from epoxide 211). Analysis of HPLC ((R,R)) Whelk-O column, 97:3, hexane:2-propanol, 1.0 mL/min; 205 nm) revealed an enantiomeric excess of 94% (t,(minor)=10.7 min, t,(major)=11.9 min). IR (thin film) 2958, 2900, 1723, 1357, 1253, 1109, 1071, 904, 844 $cm^{-1}$; $^1$H NMR($CDCl_3$) 7.46 (dd, 1H, J=2.2 and 5.7 Hz), 6.20 (dd, 1H, J=1.2 and 5.7 Hz), 4.96 (m, 1H), 2.71 (dd, 1H J=6.0 and 18.2 Hz), 2.25 (dd, 1H, J=2.3 and 18.2 Hz), 0.18 (s, 9H); $^{13}$C NMR ($CDCl_3$) δ206.3, 163.6, 134.6, 70.4, 44.8, 0.0.

The absolute configuration of 214 was assigned by desilylation of a small sample of 214 (80% ee) to provide (R)-4-hydroxy-2-cyclopentenone $[\alpha]^{23}D+73.7°$ (c 0.700, $CHCl_3$) lit. $[\alpha]22_D+81°$ (c 0.1035, $CHCl_3$) (Gill, M. et al., *Tet. Lett.* 1979: 1539–42)].

Example 17

Synthesis of a Chiral Porphyrin Ligand

Pyrrole (1.0 equivalents) and salicylaldehyde (1.2 equivalents) are dissolved in propionic acid (1 liter/20ml pyrrole) and the solution is refluxed for 30 minutes. The reaction mixture is allowed to cool to room temperature and stand for one day. The mixture is filtered and the product is recrystallized to yield 5,10,15,20-tetrakis(2'-hydroxyphenyl) porphyrin.

The above-named porphyrin is dissolved in dimethylformamide, cooled to 0° C., and treated with sodium hydride (4 equivalents). The mixture is stirred for 30 minutes, and then a solution of D-threitol 1,4-ditosylate (Aldrich Chemical Co.) in DMF is added slowly. When the addition is finished, the reaction mixture is stirred for 30 minutes more, then carefully quenched. The organic phase is washed with brine and the solvent is evaporated. The residue is purified by HPLC to yield the chiral porphyrin.

Example 18

Kinetic Resolution of Racemic Terminal Epoxides by Means of Catalyzed Hydrolysis Epoxides are versatile building blocks for organic synthesis. However, no general and practical method exists for the production of terminal epoxides, arguably the most important subclass of these compounds, in enantiomerically pure form. Terminal epoxides are available very inexpensively as racemic mixtures, and kinetic resolution is an attractive strategy for the production of optically active epoxides, given an economical and operationally simple method. Readily accessible synthetic catalysts (chiral cobalt-based salen complexes) have been discovered for the highly efficient asymmetric hydrolysis of terminal epoxides. This process uses water as the only reagent, no added solvent, very low loadings of a recyclable catalyst (<0.5 mol %), and affords highly valuable terminal epoxides and 1,2-diols in high yield and with very high enantiomeric enrichment.

Asymmetric catalysis provides access to optically active epoxides either by oxygen-atom-transfer to alkenes[1] or by carbene addition to carbonyl compounds.[2] Both strategies have been developed to varying degrees, but significant gaps still exist in the scope of these methodologies. For example, there are still no effective enantioselective epoxidation methods known for the synthesis of terminal epoxides such as propylene oxide.[3] Such epoxides are readily available as racemic mixtures, so the possibility of using a kinetic resolution strategy for accessing the enantiopure materials is attractive.[4] For kinetic resolutions in which recovery of unreacted substrate is targeted, a cheap and easily-handled reagent is obviously desirable for effecting the resolution. Ideally, the product of reaction might also be of synthetic value. To these ends, water is an extremely appealing reagent for epoxide resolutions. Not only is it completely cost-effective, safe, and environmentally benign, but the 1,2-diols generated from epoxide hydrolysis are also valuable chiral building blocks of demonstrated utility for organic synthesis.[5] We describe the first practical route to terminal epoxides in highly enantio-enriched form via a hydrolytic kinetic resolution (HKR) using simple chiral catalysts (Scheme 1; R=alkyl).[6] This process provides direct access to both unreacted epoxide and 1,2-diol products in high enantiomeric excess (ee) and yield.

Scheme 1

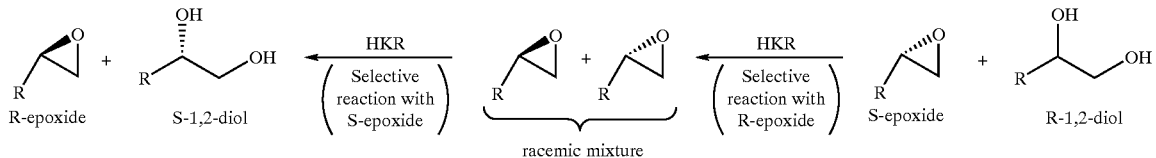

The HKR was discovered unexpectedly during the course of investigations on the reactions of epoxides with carboxylic acids. We had found previously that the (salen)Co(II) complex 1 is oxidized by air in the presence of benzoic acid to generate the corresponding (salen)Co(III)(benzoate) complex 2a, and that complex 2a catalyzes the ring-opening of meso epoxides with benzoic acid with moderate-to-good enantioselectivity.[7] In efforts to extend this methodology to the kinetic resolution of racemic epoxides,[8] we observed that a significant level of epoxide hydrolysis competed with ring-opening by benzoic acid (Scheme 2; Ph, phenyl; Et, ethyl; i-Pr, isopropyl; Bz, benzoyl). The fact that diol was being generated in very high ee suggested the participation of a highly enantioselective HKR involving adventitious water in the reaction medium.

Scheme 2

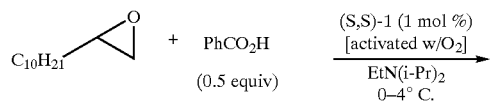

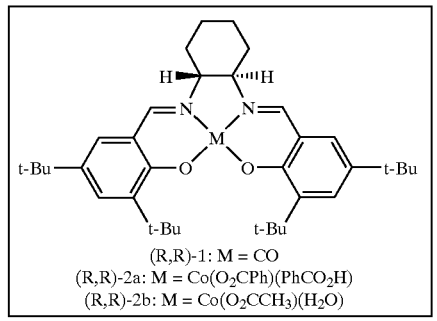

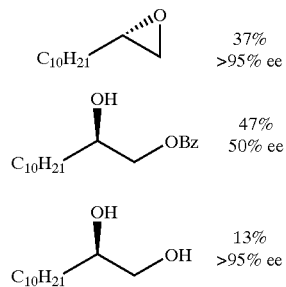

Indeed, terminal epoxides were found to react readily with water alone in the presence of (salen)Co catalysts. The solvent-free reaction of racemic propylene oxide (1.0 mole) with 0.55 equivalents of water in the presence of 0.2 mol % of (salen)Co(III)(OAc) complex 2b[9] proceeded within 12 hours at room temperature to afford a mixture of unreacted epoxide and propylene glycol.[10] Fractional distillation provided both compounds in high chemical and enantiomeric purity ($\geq$98% ee) and in nearly quantitative yield.[11,12] The non-volatile residue obtained after distillation contained reduced complex 1; active catalyst 2b was regenerated from this material by treatment with acetic acid in air, such that the catalyst could be recycled with no observable loss in activity or selectivity (Scheme 3).

Scheme 3

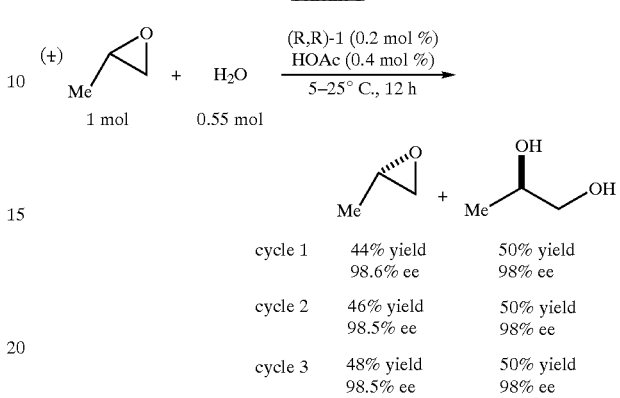

The HKR was also found to be applicable to a series of other terminal epoxides (Table 1). The substrates shown are representative of epoxides that are very inexpensive as racemates and which previously have not been readily accessible in optically pure form. Unbranched alkyl-substituted epoxides[13] such as 1-hexene oxide and 1-octene oxide were found to be superb substrates for the HKR ($k_{rel}$>250). Epichlorohydrin (entry 2) also underwent efficient resolution, although the diol product was formed with lower ee (86%). Conjugated epoxides such as styrene oxide and butadiene monoepoxide were resolved with lower selectivity (entries 5 to 7), but highly enantioenriched epoxide or diol could still be obtained in useful yield by simply adjusting the amount of water used in the reaction (such as entries 6 and 7).

TABLE 1

Hydrolytic kinetic resolution of terminal epoxides with water catalyzed by 2b. The values for $k_{rel}$ were calculated using the equation $k_{rel} = \ln[(1-c)(1-ee)]/\ln[(1-c)(1+ee)]$, where ee is the enantiomeric excess of the epoxide and c is the fraction of epoxide remaining in the final reaction mixture (4).

| | | Concentration | | | Epoxide | | Diol | | |
|---|---|---|---|---|---|---|---|---|---|
| Entry | R | 2b (mol %) | Water (equiv) | Time (hours) | ee (%) | Isolated yield (%) | ee (%) | Isolated yield (%) | $k_{rel}$ |
| 1 | CH$_3$ | 0.2 | 0.55 | 12 | >98 | 44 | 98 | 50 | >400 |
| 2 | CH$_2$Cl | 0.3 | 0.55 | 8 | 98 | 44 | 86 | 38 | 50 |
| 3 | (CH$_2$)$_3$CH$_3$ | 0.42 | 0.55 | 5 | 98 | 46 | 98 | 48 | 290 |
| 4 | (CH$_2$)$_5$CH$_3$ | 0.42 | 0.55 | 6 | 99 | 45 | 97 | 47 | 260 |
| 5 | Ph | 0.8 | 0.70 | 44 | 98 | 38 | 98* | 39* | 20 |
| 6 | CH=CH$_2$ | 0.64 | 0.50 | 20 | 84 | 44 | 94 | 49 | 30 |
| 7 | CH=CH$_2$ | 0.85 | 0.70 | 68 | 99 | 29 | 88 | 64 | 30 |

*After recrystallization.

Preliminary kinetic studies were carried out on the HKR of 1-octene oxide. Although this epoxide is immiscible with water, the reaction mixture was rendered homogeneous by addition of 20 mol % ($\pm$)-1,2-hexanediol. This additive had no measurable effect on the enantioselectivity of the reaction, but it did allow the acquisition of reproducible rate constant data. The reaction was observed to follow a second-order dependence on the concentration of 2b, consistent with a mechanism wherein two discrete catalyst molecules cooperate to activate both the electrophile (epoxide) and the nucleophile (water). Compelling evidence for a similar bimetallic mechanism has been obtained in the asymmetric ring-opening of epoxides by azide nucleophiles catalyzed by related chromium-containing catalysts.[14] It is noteworthy that bimetallic catalysis is apparently operative with such distinct classes of reactions, and it hints at the possible generality of such a mechanism.

The HKR stands as a new and very attractive procedure for the preparation of optically enriched terminal epoxides and 1,2-diols. The criteria for evaluating the practicality of chemical processes such as this one have become increasingly stringent. High standards of yield and selectivity in product formation must be met, but additional issues such as reagent cost, volumetric productivity, waste generation, reagent toxicity, and handling risks weigh more heavily than ever before. With these criteria positively met, the HKR appears to hold significant potential for large-scale application.[15]

References and Notes for Example 18

1. E. N. Jacobsen in *Comprehensive Organometallic Chemistry II*; G. Wilkinson, F. G. A. Stone, E. W. Abel, L S. Hegedus, Eds. (Pergamon, New York, 1995) Vol. 12, Chapter 11.1.
2. V. K. Aggarwal, J. G. Ford, A. Thompson, R. V. H. Jones, M. Standen, *J. Am. Chem. Soc.* 118, 7004 (1996).
3. The highest enantioselectivity reported to date for the epoxidation of propylene is 41%. R. Sinigalia, R. A. Michelin, F. Pinna, G. Strukul, *Organometallics* 6, 728 (1987).
4. For leading references on kinetic resolution, see: E. L. Eliel, S. H. Wilen, L. M. Mander, *Stereochemistry of Organic Compounds*; (Wiley-Interscience, New York, 1994), pp. 395–415; H. B. Kagan, J. C. Fiaud, in *Topics in Stereochemistry*; N. L. Allinger, E. L. Eliel, Eds. (Interscience, New York, 1987) Vol. 14, p 249.
5. H. C. Kolb, M. S. VanNieuwenhze, K. B. Sharpless, *Chem. Rev.* 94, 2483 (1994).
6. Enantioselective hydrolysis of epoxides using biocatalysts has received considerable attention. See: K. Faber, *Biotransformations in Organic Chemistry* (Springer-Verlag, New York, 1992) Chapter 2.1.5; C. A. G. M. Weijers, *Tetrahedron: Asymmetry* 8, 639 (1997), and references cited therein.
7. E. N. Jacobsen, F. Kakiuchi, R. G. Konsler, J. F. Larrow, M. Tokunaga,*Tetrahedron Lett.* 38, 773 (1997).
8. The kinetic resolution of epoxides with $(CH_3)_3SiN_3$ with (salen)Cr complexes has been documented: J. F. Larrow, S. E. Schaus, E. N. Jacobsen,*J. Am. Chem. Soc.* 118, 7420 (1996). Despite the high selectivity observed in these kinetic resolutions, this method is impractical for the recovery of enantioenriched epoxide because it requires consumption of azide, a relatively precious reagent.
9. Complex 2b can be generated in situ from 1 (ref. 7) by treatment with acetic acid (2 equiv.) in toluene under air, followed by evaporation of solvent. $^1$H nuclear magnetic resonance (NMR) (400 MHz, dry acetone-$d_6$) δ (ppm) relative to tetramethylsilane: −1.95 (br s, 2 H, $H_2O$), 1.21 (s, 9 H, $^tBu$), 1.28 (s, 9 H, $^tBu$), 1.33 (s, 9 H, $^tBu$), 1.53 (s, 9 H, $^tBu$), 1.58 (s, 3 H, $CH_3C(O)$), 1.6 (m, 2 H, $CH_2$), 1.9–2.0 (m, 2 H, $CH_2$), 2.23 (br q, J=9.8 Hz, 1 H, CHH), 2.79 (d, J=11.8 Hz, 1 H, CHH), 2.88 (br d, 2 H, $CH_2$), 3.27 (brt, 1 H, CHN), 4.35 (brt, 1 H, CHN), 7.17 (d, J=2.4 Hz, 1 H, ArH), 7.22 (s, 1 H, CH=N), 7.29 (d, J=2.4 Hz, 1 H, ArH), 7.35 (d, J=2.4 Hz, 1 H, ArH), 7.46 (d, J=2.4 Hz, 1 H, ArH), 7.59 (s, 1 H, CH=N). IR (KBr) 1719 w, 1638 s, 1611 s, 1545 s, 1540 s, 1526 s, 1461 s, 1436 s, 1408 s, 1390 s, 1361 s, 1339 s, 1323 s, 1270 s, 1255 s, 1235 m, 1202 m, 1169 s, 834 m, 783 m; mp (open capillary) 108° C. (dec.)
10. The hydrolysis reactions were observed to be mildly exothermic on laboratory scale. For the kinetic resolution of propylene oxide (bp 34° C.), the reaction vessel was cooled with an external ice bath during the addition of water to limit substrate loss due to evaporation.
11. A mixture of (S,S)-1 (1.208 g, 2.0 mmol, 0.2 mol %), toluene (10 ml), and acetic acid (0.23 ml, 4.0 mmol, 2 equiv to catalyst) was stirred open to the air for 1 hour at room temperature. The solvent was removed by rotary evaporation, and the brown residue was dried under vacuum. Propylene oxide (58.7 g, 1.0 mol) was added in one portion, and the stirred mixture was cooled in an ice/water bath. Water (9.9 ml, 0.55 mol, 0.55 equiv) was slowly added until the temperature of the reaction mixture was observed to begin rising, at which point addition was suspended. The temperature rose to ~25° C. before dropping to 15° C., at which point water addition was continued at a rate that maintained the reaction temperature near 20° C. After 1 hour, addition was complete; the ice bath was removed, and the reaction was stirred at room temperature for 11 hours. The flask was then affixed with a distillation head equipped with a receiver cooled to −78° C., and the unreacted epoxide was distilled under $N_2$ until no more material came over with gentle heating. The system was then placed under mild vacuum to collect any residual epoxide (yield: 26.05 g, >99% pure by GC, 0.444 mol, 44% yield). The receiver was changed and the system was carefully placed under full vacuum (<0.5 mm Hg). The diol was then distilled under vacuum into an ice-cooled receiver and isolated as a colorless, viscous liquid (yield: 38.66 g, >99% pure by GC, 0.503 mol, 50% recovery).
12. It is significant that propylene glycol is isolated in high enantiomeric purity and yield. Even though excellent methods exists for the asymmetric dihydroxylation (AD) of most olefins (see ref. 5), the highest enantioselectivity obtained to date in the AD of propylene is only 49%. K. P. M. Vanhessche, K. B. Sharpless, *Chem. Eur. J.* 3, 517 (1997).
13. For a practical method for the epoxidation of α-olefins, see: K. Sato, M. Aoki, M. Ogawa, T. Hashimoto, R. Noyori, *J. Org. Chem.* 61, 8310 (1996).
14. K. B. Hansen, J. L. Leighton, E. N. Jacobsen, *J. Am. Chem. Soc.* 118, 10924 (1996).
15. The HKR of propylene oxide has been carried out successfully on a 10 kg scale in the pilot plant at Chirex, Inc. (Dudley, U K). J. Cummins and G. Thorpe, private communication.

Example 19

Practical Access to Highly Enantioenriched C-3 Building Blocks via Hydrolytic Kinetic Resolution Efficient methods are described for the hydrolytic kinetic resolution (HKR) of a variety of readily available C-3 building blocks using (salen)Co(III) complex 1. Epichlorohydrin undergoes HKR to 50% conversion to afford both recovered epoxide and ring-opened diol in 96% ee. Epoxide can be generated in >99% ee and 42% isolated yield under slightly modified conditions, while diol can be prepared in >99% ee and 41% overall yield by means of HKR with (S,S)-1 and subsequent hydrolysis of the resolved epichlorohydrin catalyzed by (R,R)-1. Epibromohydrin undergoes rapid racemization under the conditions of HKR, thereby allowing a dynamic HKR to produce the corresponding bromopropane diol in 96% ee and 93% yield. The HKR of a series of glycidol derivatives is, also shown to proceed effectively, providing access to corresponding epoxides in >99% ee and 44–48% isolated yields.

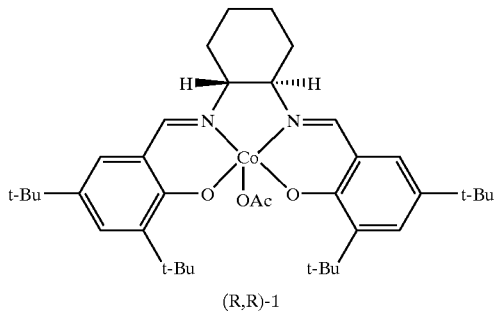

(R,R)-1

Kinetic resolution (KR) can be a highly effective strategy for the preparation of optically pure compounds, particularly if the corresponding racemates are readily available and a practical procedure for KR can be applied. In this light, the recently-disclosed hydrolytic kinetic resolution (HKR) reaction catalyzed by (salen)Co complex 1 (eq. 1) constitutes a very attractive approach toward the preparation of enantiopure terminal epoxides. The features of the HKR include: the use of water as the nucleophile for epoxide ring-opening; the high accessibility of racemic terminal epoxides, the low loadings and recyclability of the commercially available catalyst; and the ease of product separation from unreacted epoxide due to large boiling point and polarity differences.

(1)

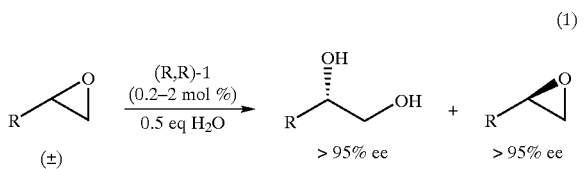

Epihalohydrins and glycidol derivatives are particularly attractive substrates for HKR because the racemates are available inexpensively and on large scale, and the chiral three-carbon (C-3) building blocks derived from these compounds are extremely versatile synthetic intermediates. In the initial report on the HKR, 2 epichlorohydrin was the only C-3 substrate evaluated and its resolution was described to afford recovered epoxide in 44% yield and 98% ee, but the diol was obtained in only 38% yield and 86% ee. In this communication we describe a highly-optimized protocol for the HKR of epichlorohydrin to provide either epoxide or diol in >99% ee, as well as the highly efficient dynamic HKR of epibromohydrin. The HKR methodology is also shown to be applicable to a variety of important glycidol derivatives.

Epihalohydrins are susceptible to racemization catalyzed by adventitious halide ion, and this stands as a critical issue in any kinetic resolution of these substrates. Indeed, this racemization pathway has been used to advantage in the resolution of epichlorohydrin with TMSN$_3$ catalyzed by the Cr analog of 1. In that case, racemization was rapid enough relative to the ring-opening pathway to allow for a dynamic kinetic resolution affording the ring-opened product in 76% yield and 97% ee. In contrast, racemization of epichlorohydrin was found to take place only very slowly relative to hydrolysis under hydrolytic conditions with Co catalyst 1, (eq. 2). This racemization was suppressed by addition of THF as solvent, thereby allowing the HKR of (−)-epichlorohydrin with 0.50 equiv of H$_2$O to provide both epoxide and diol in 96% ee and in isolated yields of 44% and 50%, respectively (eq. 3). Enantiopure epichlorohydrin (>99% ee) could be obtained in 42% isolated yield by resolution under the same conditions using 0.55 equiv of water. In both cases catalyst 1 could be regenerated and reused with no loss of activity or enantioselectivity (see Supporting Information).

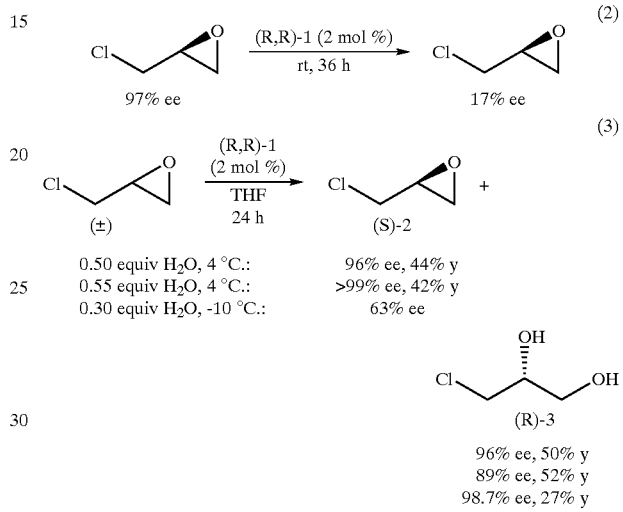

The HKR product of epichlorohydrin, chloropropane diol 3, is also a very valuable chiral C-3 building block, and conditions were sought for its production in high optical purity. The HKR of epichlorohydrin at reduced temperature and lower conversion (−10° C., 0.3 equiv H$_2$O) gave (R)-3 in 98.7% ee and 27% yield (eq. 3). This corresponds to a selectivity factor in the HKR of epichlorohydrin of at least 218. Enantiopure (R)-3 (>99% ee) was easily obtained by HKR of epichlorohydrin to >99% ee with (S,S)-1, as described above, followed by vacuum distillation of the epoxide and THF and subsequent ring opening of the resolved epoxide using (R,R)-1. This sequence, which takes advantage of the equal availability of both enantiomers of catalyst 1, provides an attractive route to (R)-3 or (S)-3 in 41% overall isolated yield from racemic epichlorohydrin (eq. 4).

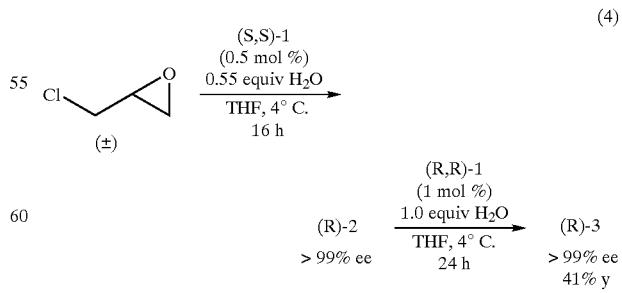

In contrast to the slow rate of racemization observed for epichlorohydrin under HKR conditions, epibromohydrin was found to undergo racemization relatively rapidly. Thus, at 50% conversion in the hydrolysis of epibromohydrin with (R,R)-1, epoxide was recovered in only 6% ee while diol was produced in 96% ee. As a result, epibromohydrin was evaluated as a possibly viable substrate for dynamic kinetic resolution. The reaction of racemic epoxide with 1.5 equivalents of $H_2O$ in THF in the presence of 2 mol % (R,R)-1 gave diol 46 in 96% ee and 93% isolated yield (eq. 5). This therefore represents a particularly effective example of dynamic kinetic resolution, both from the point of view of enantioselectivity and yield.

(5)

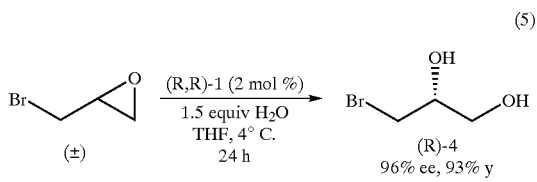

Diols 3 and 4 are immediate precursors to glycidol (5a), another broadly useful C-3 building block. Upon treatment with potassium carbonate, enantiopure (R)-3 obtained as described above was converted to (R)-5a in 88% isolated yield and >99% ee (eq. 6). In the same manner (R)-4 was converted to (R)-5a in 88% yield. These HKR/cyclization sequences represent straightforward, efficient methods for the synthesis of enantioenriched glycidol from racemic epichlorohydrin or epibromohydrin.

(6)

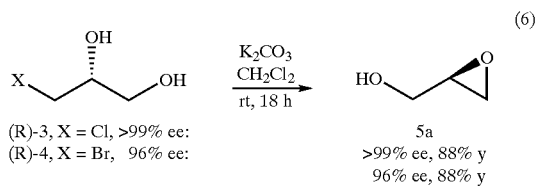

The HKR of glycidol itself provided resolved epoxide in low yield as a result of the participation of undesired oligomerization pathways (eq. 7). In contrast, the HKR was found to be highly effective in the resolution of glycidol derivatives. Under standard conditions employing 0.5 mole % (R,R)-1 and 0.55 equivalents of $H_2O$, benzyl glycidyl ether, tert-butyldimethylsilyl glycidyl ether and glycidyl butyrate were each obtained in >99% ee and 47%, 48%, and 44% yield, respectively.

(7)

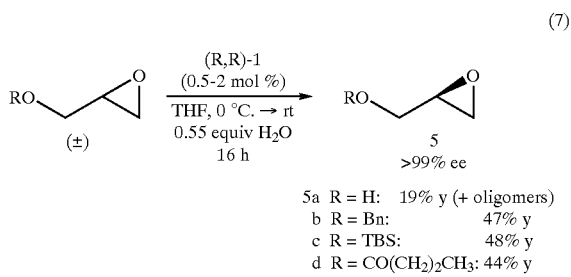

The high enantioselectivity in the HKR of epichlorohydrin and glycidol derivatives makes it possible to isolate either epoxide or the corresponding diols in highly enantioenriched forms. We are hopeful that the ready access to C-3 building blocks in enantiopure form provided by the HKR methodology will have a significant enabling impact on the use of these intermediates in pharmaceutical and natural product synthesis.

Publications and Notes for Example 19

(1) Kagan, H. B.; Fiaud, J. C. in Topics in Stereochemistry, Vol. 14, Eliel, E. L.; Wilen, S. H., eds.; Wiley: New York, 1987, pp. 249–330.
(2) Tokunaga, M.; Larrow, J. F.; Kakiuchi, F.; Jacobsen, E. N. Science 1997, 277, 936.
(3) (S,S)-N,N'-Bis(3,5-di-tert-butylsalicylidene)-1,2-cyclohexanediaminocobalt(II): Aldrich #47,460–6; (R,R)-N,N'-Bis(3,5-di-tert-butylsalicylidene)-1,2-cyclohexanediaminocobalt(II): Aldrich #47,459–2. The corresponding Co(III) complex 1 is generated either in situ in the HKR or in a discrete step by exposure of the Co(II) complex to air in the presence of AcOH. See Supporting Information for complete experimental details.
(4) For an alternative route to enantioenriched epichldrohydrin employing asymmetric catalysis, see: Takeichi, T.; Arihara, M.; Ishimori, M.; Tsuruta, T. Tetrahedron 1980, 36, 3391.
(5) For the synthesis of enantiopure epichlorohydrin by enzymatic resolution of 2,3-dichloro-1-propanol, see: Kasai, N.; Tsujimura, K.; Suzuki, T. Jpn. Patent JP 02 257 895, 1990; Chem. Abstr. 1991, 114, 41064q.
(6) Schaus, S. E.; Jacobsen, E. N. Tetrahedron Lett. 1996, 37, 7937.
(7) For the synthesis of 3 and 4 by asymmetric dihydroxylation, see: Becker, H; Sharpless, K. B. Angew. Chem. Intl. Ed. Engl. 1996, 35, 448.
(8) For a review, see: Noyori, R.; Tokunaga, M.; Kitamura, M. Bull. Chem. Soc. Jpn. 1995, 68, 36.
(9) For a review of, the synthetic applications of glycidol and glycidol derivatives, see: Hansen, R. H. Chem. Rev. 1991, 91, 437.
(10) For the synthesis of glycidol by asymmetric epoxidation of allyl alcohol, see: (a) Klunder, J. M.; Ko, S. Y.; Sharpless, K. B. J. Org. Chem. 1986, 51, 3710. (b) Hanson, R. M.; Ko, S. Y.; Gao, Y.; Masemune, H.; Klunder, J. M.; Sharpless, K. B. J. Am. Chem. Soc. 1987, 109, 5765.
(11) For the enzymatic resolution of benzyl glycidyl ether, see: (a) Weijers, C. A. G. M. Tetrahedron: Asymmetry 1997, 8, 639. (b) Pederson, R. L.; Liu, K. K.-C.; Rutan, J. F.; Chen, L.; Wong, C. -H. J. Org. Chem. 1990, 55, 4897.
(12) For the enzymatic resolution of glycidyl butyrate, see: Ladner, W. E.; Whitesides, G. M. J. Am. Chem. Soc. 1984, 106, 7250.

Supporting Information for Example 19

General: All reactions were conducted in standard glassware with magnetic stirring under an atmosphere of air. Tetrahydrofuran (THF) was distilled from sodium/benzophenone ketyl. (+/−)-Epichlorohydrin and (+/−)-epibromohydrin were purchased from Aldrich and used as received. Racemic benzyl glycidyl ether, (tert-butyldimethylsilyl) glycidyl ether, and glycidyl butyrate were synthesized utilizing known procedures. The (salen) Co(II) precatalyst was utilized directly and oxidized in situ in the hydrolytic kinetic resolutions of 5b-d.

Determination of Enantiomeric Purity: Enantiomeric excesses (ee) were determined by capillary GC analysis or Chiral HPLC analysis using commercially available chiral columns. The following GC columns were employed: Cyclodex-B (30 m×0.25 mm id×0.25 mm film; J&W Scientific); Chiraldex g-TA (20 m×0.25 mm id×0.125 mm film; Advanced Separation Technologies, Inc.). The chiral HPLC column used was a Chiracel OD (25 cm×4.6 mm, Chiral Technologies, Inc.).

Preparation of 1—The (salen)Co(III)(OAc) 1 catalyst was prepared using the (salen)Co(II) precatalyst commercially available from Aldrich. The Co(II) complex was dissolved in $CH_2Cl_2$ and acetic acid (4 equiv.) to generate a 0.2 M brown solution. After stirring in air for 10 min, the mixture was concentrated in vacuo to generate 1 in quantitative yield as a brown solid which was used without any further purification. $^1$H NMR (400 MHz, dry acetone-d6) d_1.95 (br s, 2 H, H2O), 1.21 (s, 9 H, tBu), 1.28 (s, 9 H, tBu), 1.33 (s, 9 H, tBu), 1.53 (s, 9 H, tBu), 1.58 (s, 3 H, CH3C(O)), 1.6 (m, 2 H, CH2), 1.9–2.0 (m, 2 H, CH2), 2.23 (br q, J=9.8 Hz, 1 H, CHH), 2.79 (d, J=11.8 Hz, 1 H, CHH), 2.88 (br d, 2 H, CH2), 3.27 (brt, 1 H, CHN), 4.35 (brt, 1 H, CHN), 7.17 (d, J=2.4 Hz, 1 H, ArH), 7.22 (s, 1 H, CH=N), 7.29 (d, J=2.4 Hz, 1 H, ArH), 7.35 (d, J=2.4 Hz, 1 H, ArH), 7.46 (d, J=2.4 Hz, 1 H, ArH), 7.59 (s, 1 H, CH=N). IR (KBr) 1719 w, 1638 s, 1611 s, 1545 s, 1540 s, 1526 s, 1461 s, 1436 s, 1408 s, 1390 s, 1361 s, 1339 s, 1323 s, 1270 s, 1255 s, 1235 m, 1202 m, 1169 s, 834 m, 783 m; mp (open capillary) 108° C. (dec.)

(R)-3–Chloro-1,2-propanediol (96% ee); (S)-epichlorohydrin (96% ee)—A 500 mL 3-neck flask equipped with a stir bar, addition funnel, and thermometer was charged with 6.81 g (10.0 mmol) of (R,R)-1. The flask was charged with 61 mL THF and cooled to 0° C. followed by the addition of (+/−)-epichlorohydrin (39.1 mL, 500 mmol). To the reaction was added $H_2O$ (4.50 mL, 250 mmol) dropwise, over 1 h, maintaining the temperature between 0° C. and 4° C. The reaction solution was then allowed to stir at 4° C. for 17 h at which time the THF and remaining epichlorohydrin were transferred under reduced pressure to a 500 mL flask cooled with liquid $N_2$. The THF was removed using by rotary evaporation at 20° C. to yield (S)-epichlorohydrin (20.5 g, 221 mmol, 44%). The recovered epichlorohydrin was determined to be 96% ee by chiral GC analysis (Chiraldex g-TA, 40° C., 20 min).

The residual reaction mixture was diluted with 40 mL $H_2O$ and 40 mL $CH_2Cl_2$ and the aqueous layer was separated. The organic layer was extracted with 4×15 mL $H_2O$ and 4×10 mL $H_2O$. The organic layer was concentrated in vacuo and the residue was triturated with 20 mL $H_2O$. The aqueous layers were collected, concentrated in vacuo to approximately one third of the original volume, and then filtered to remove residual catalyst. The resulting aqueous solution was further concentrated in vacuo to yield 27.8 g (R)-3-chloro-1,2-propanediol (251 mmol, 50%). Chiral GC analysis of the corresponding acetal (prepared from 2,2-dimethoxypropane and catalytic p-toluenesulfonic acid) indicated that the product was obtained in 96% ee (Cyclodex-B, 75° C. for 15 min).

The catalyst residue was collected as the Co(II) complex. Complex 1 was regenerated as described above and the HKR procedure was repeated to yield 20.0 g (S)-epichlorohydrin (216 mmol, 96% ee, 43%), and 26.8 g (R)-3-chloro-1,2-propanediol (242 mmol, 96% ee, 48%).

(R)-3-Chloro-1,2-propanediol (89% ee); (S)-Epichlorohydrin (>99% ee)—A 50 mL flask equipped with a stir bar, was charged with (R,R)-1 (1.47 g, 2.16 mmol). The catalyst was dissolved in 13 mL THF and cooled to 0° C. followed by the addition of (+/−)-epichlorohydrin (8.45 mL, 108 mmol). To the reaction was added $H_2O$ (1.07 mL, 59.4 mmol) in one portion. The reaction solution was then allowed to stir at 4° C. for 17 h at which time the THF and remaining epichlorohydrin were transferred under reduced pressure to a 25 mL flask cooled with liquid $N_2$. The THF was removed by rotary evaporation to yield (S)-epichlorohydrin (4.16 g, 45.0 mmol, 42%). The recovered epichlorohydrin was determined to be >99% ee by chiral GC analysis (Chiraldex g-TA, 40° C., 20 min).

The residual reaction mixture was diluted with 4 mL $H_2O$ and 4 mL $CH_2Cl_2$ and the aqueous layer was separated. The organic layer was extracted with 4×5 mL $H_2O$ and 4×10 mL $H_2O$ and the organic layer was concentrated in vacuo. The residue was triturated with 4 mL $H_2O$. The aqueous layers were collected and concentrated in vacuo, yielding 6.31 g (R)-3-chloro-1,2-propanediol (57.1 mmol, 53%). Chiral GC analysis of the corresponding acetal (prepared from 2,2-dimethoxypropane and catalytic p-toluenesulfonic acid) indicated that the product was present in 89% ee (Cyclodex-B, 75° C., 15 min).

The procedure was repeated using 1 regenerated from the recovered catalyst to yield 4.37 g (S)-epichlorohydrin (47.2 mmol, >99% ee, 43%), and 6.44 g (R)-3-chloro-1,2-propanediol (58.2 mmol, 89% ee, 54%).

(R)-3–Chloro-1,2-propanediol (98.7% ee)—A 250 mL flask equipped with a stir bar and a thermometer was charged with (R,R)-1 (1.47 g, 2.15 mmol). The catalyst was dissolved in 13 mL THF and cooled to −10° C. The flask was charged with (+/−)-epichlorohydrin (8.45 mL, 108 mmol) followed by the addition $H_2O$ (584 mL, 32.4 mmol) over 1.5 h via syringe pump. The reaction solution was allowed to stir at −10° C. for 24 h at which time the reaction solution was then cooled to −78° C. and diluted with 250 mL $CH_2Cl_2$. The solution was then transferred to a separatory funnel and 75 mL of water were added. The aqueous layer was separated, extracted with 2×15 mL $CH_2Cl_2$ and vacuum-filtered to remove the remaining catalyst. The filtrate was concentrated in vacuo to give 3.19 g of (R)-3-chloro-1,2-propanediol (28.9 mmol, 27%). Chiral GC analysis of the corresponding acetal (prepared from 2,2-dimethoxypropane and catalytic p-toluenesulfonic acid) indicated that the product was produced in 98.7% ee (Cyclodex-B, 75° C., 15 min).

(R)-3–Chloro-1,2-propanediol (>99% ee)—A 50 mL flask equipped with a stir bar, was charged with (S,S)-1 (511 mg, 0.750 mmol). The catalyst was dissolved in 18 mL THF and cooled to 0° C. followed by the addition of (+/−)-epichlorohydrin (11.73 mL, 150 mmol). The reaction flask was charged $H_2O$ (1.49 mL, 82.5 mmol) dropwise over 1 h. The reaction solution was allowed to stir at 4° C. for 16 h at which time (R)-epichlorohydrin was determined to be >99% ee (Chiraldex g-TA, 40° C., 20 min). The THF and remaining epichlorohydrin were transferred under reduced pressure to a 100 mL flask cooled with liquid $N_2$. To this was then added (R,R)-1 (511 mg, 0.750 mmol). The solution was cooled to 4° C. and $H_2O$ (1.35 mL, 75.0 mmol) was added dropwise over 10 minutes. The reaction solution was then allowed to stir at 4° C. for 24 h at which time the THF was removed in vacuo. The residue was then distilled (65° C., 0.5 torr) to yield (R)-3-chloro-1,2-propanediol (6.86 g, 62.1 mmol, 41%). Chiral GC analysis of the corresponding acetal (prepared from 2,2-dimethoxypropane and catalytic p-toluenesulfonic acid) indicated that the product was obtained in >99% ee (Cyclodex-B, 75° C., 15 min).

(R)-3-Bromo-1,2-propanediol (96% ee)—A 500 mL 3-neck flask equipped with a stir bar, addition funnel, and thermometer was charged with (R,R)-1 (6.81 g, 10.0 mmol). The catalyst was dissolved in 57 mL THF and cooled to 0° C. (+/−)-Epibromohydrin (42.8 mL, 500 mmol) was added and then $H_2O$ (13.5 mL, 750 mmol) was added dropwise over 1 h while the temperature was maintained between 0° C. and 4° C. The mixture was allowed to stir at 4° C. for 48 h at which time the reaction solution was diluted with 80 mL benzene and 80 mL $H_2O$ The aqueous layer was separated and the benzene layer was extracted with 2×25 mL $H_2O$, concentrated in vacuo, and triturated with 25 mL $H_2O$. The aqueous extracts were concentrated in vacuo to approximately one third of the original volume and then vacuum-filtered to remove residual catalyst. The filtrate was concentrated to give 71.7 g (R)-3-bromo-1,2-propanediol (463 mmol, 93%). Chiral GC analysis of the corresponding acetal (prepared from 2,2-dimethoxypropane and catalytic p-toluenesulfonic acid) indicated that the product was obtained in 96% ee (Cyclodex-B, 75° C., 25 min). The catalyst collected from the final filtration was dissolved in $CH_2Cl_2$, added to the rest of the catalyst, and concentrated in vacuo.

The procedure was repeated using 1 generated from the recovered catalyst under identical conditions to yield 73.4 g (R)-3-bromo-1,2-propanediol (474 mmol, 96% ee).

(R)-glycidol (99% ee; from (R)-3-chloro-1,2-propanediol)—An oven-dried 100 mL flask equipped with a stir bar was charged with 3.00 g (27.1 mmol) of (R)-3-chloro-1,2-propanediol (>99% ee). This was dissolved in methylene chloride (30 mL) and treated with $K_2CO_3$ (9.40 g, 67.8 mmol). The flask was sealed and allowed to stir at rt for 24 h at which time the resulting mixture was vacuum filtered through Celite. The filtrate was concentrated in vacuo and azeotroped 2×5 mL benzene to yield 1.78 g (R)-glycidol (24.0 mmol, 88%). Chiral GC analysis of the corresponding acetate (prepared from acetyl chloride in pyridine) indicated that the product was obtained in >99% ee (Chiraldex g-TA, 55_C, 5 min, 1° C./min to 85° C.).

(R)-glycidol (96% ee; from (R)-3-bromo-1,2-propanediol)—An oven dried 100 mL flask equipped with a stir bar was charged with (R)-3-bromo-1,2-propanediol (3.00 g, 19.4 mmol, 96% ee). The diol was dissolved in methylene chloride (30 mL) and treated with $K_2CO_3$ (9.40 g, 67.8 mmol). The flask was sealed and allowed to stir at rt for 18 h at which time the resulting mixture was vacuum filtered through Celite. The filtrate was concentrated in vacuo and azeotroped 2×5 mL benzene to yield 1.27 g (R)-glycidol (17.2 mmol, 88%). Chiral GC analysis of the corresponding acetate (prepared from acetyl chloride in pyridine) indicated that the product was obtained in 96% ee (Chiraldex g-TA, 55° C., 5 min, 1° C./min to 85° C.).

Hydrolytic Kinetic Resolution of Glycidol; (R)-Glycidol 5a: An oven dried 25 mL flask equipped with a stir bar was charged with (R,R)-1 (551 mg, 0.810 mmol). The catalyst was dissolved in 5.4 mL THF and cooled to 0° C. (+/−)-Glycidol (2.69 mL, 40.5 mmol) was added to the solution followed by the addition of $H_2O$ (401 mL, 22.3 mmol). The reaction was allowed to stir at 4° C. for 14 h at which time the remaining glycidol was vacuum distilled from the reaction mixture (30° C., 0.5 Torr) to yield (R)-glycidol 5a (0.580 g, 7.83 mmol, 19%). Chiral GC analysis of the corresponding acetate (prepared from acetyl chloride in pyridine) indicated that the product was obtained in >99% ee (Chiraldex g-TA, 55° C., 5 min, 1° C./min to 85° C.)

General procedure for the Hydrolytic Kinetic Resolution of 5b-d, (R)-benzyl glycidyl ether 5b: A 100 mL flask equipped with a stir bar was evacuated and flushed with air. The flask was charged with the (R,R)-(salen)Co(II) precatalyst (151 mg, 0.250 mmol, 0.5 mol %) and sealed with a rubber septum equipped with an air outlet. The flask was charged sequentially with (+/−)-benzyl glycidyl ether (8.20 g, 50.0 mmol) and AcOH (57 mL, 1.0 mmol, 0.02 equiv). After the reaction mixture turned from a red suspension to a dark brown solution, the flask was cooled to 0° C. and THF (0.5 mL) and H2O (495 mL, 27.5 mmol, 0.55 equiv) were added. The reaction was allowed to warm to rt over 2 h and stir an additional 12 h. The unreacted (R)-benzyl glycidyl ether 5b was distilled under vacuum (110° C., 0.5 Torr) from the reaction mixture to yield 47% of a clear oil. The epoxide thus isolated was determined to be present in >99% ee (Chiralcel OD, 95:5 hexanes:i-PrOH, 1 mL/min, 214 nm).

(S)-(tert-Butyldimethylsilyl) glycidyl ether 5c: Using the (R,R)-(salen)Co(II) precatalyst of 1 (91 mg, 0.15 mmol, 0.005 equiv), (+/−)-(tert-butyldimethylsilyl) glycidyl ether (5.64 g, 30.0 mmol), AcOH (32 mL, 0.6 mmol 0.02 equiv), 0.3 mL THF, and $H_2O$ (297 mL, 16.5 mmol, 0.55 equiv) and a procedure analogous to the one outlined for 5b, (S)-(tert-butyldimethylsilyl) glycidyl ether 5c (2.72 g, 14.5 mmol, 48%) was obtained as a clear oil by vacuum distillation of the reaction mixture (30° C., 0.5 Torr). The product was determined to be present in >99% ee by derivatization through ring opening with 2-napthalenethiol in methanol using 1 equiv TEA at 0° C. and direct analysis of the 2-naptylsulfide thus obtained (Chiralcel OD, 99.25:0.75 hexanes:EtOH, 1 mL/min, 230 nm).

(S)-Glycidyl butyrate 5d: Using the (R,R)-(salen)Co(II) precatalyst of 1 (91 mg, 0.15 mmol, 0.005 equiv), (+/−)-glycidyl butyrate (4.32 g, 30.0 mmol), AcOH (32 mL, 0.6 mmol, 0.02 equiv), 0.3 mL THF, and $H_2O$ (297 mL, 16.5 mmol, 0.55 equiv) and a procedure analogous to the one outlined for 5b, (S)-glycidyl butyrate 5d (1.90 g, 13.2 mmol, 44%) was obtained as a clear oil by vacuum distillation of the reaction mixture (30° C., 0.5 torr). The product was determined to be >99% ee by conversion to and analysis of the 2-napthylsulfide (obtained by ring opening with 2-napthalenethiol in methanol using 1 equiv TEA at 0° C.; Chiralcel OD, 97:3 hexanes:EtOH, 1 mL/min, 260 nm).

Example 20

Synthesis of Enantiopure 3-Chlorostyrene Oxide via an Asymmetric Epoxidation-Hydrolytic Kinetic Resolution Sequence 3–Chlorostyrene oxide was prepared in >99% ee employing the (salen)Co-catalyzed hydrolytic kinetic resolution (HKR) reaction. The HKR was performed successfully on both racemic and enantiomerically enriched epoxides, the latter obtained via (salen)Mn-catalyzed asymmetric epoxidation reactions.

Styrene oxide derivatives are important chiral building blocks for the synthesis of a variety of pharmaceutically significant compounds. One derivative in particular, 3-chlorostyrene oxide (1), is a key intermediate for the preparation of several β-3-adrenergic compounds that exhibit antiobesity and antidiabetic therapeutic properties. As might be expected for such an important target, several different approaches have been documented for its synthesis in enantiomerically enriched form. Reduction of 2,3'-dichloroacetophenone using a oxazaborolidine-based catalyst afforded the chlorohydrin precursor to the epoxide in 85% ee and 36% overall yield from commercially available 3'-chloroacetophenone. Asymmetric dihydroxylation of 3-chlorostyrene followed by a stereospecific dehydrative ring closure afforded 1 in 98% ee and good yield. Enyzmatic resolution of racemic 1 has also yielded enantiopure 1, albeit in less than 5% yield. Unfortunately, the most straightforward route to enantiopure 1—asymmetric epoxidation (AE) of 3-chlorostyrene—has not been developed in a practical manner.

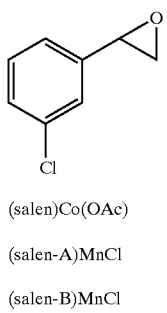

1

(salen)Co(OAc)  2

(salen-A)MnCl  3

(salen-B)MnCl  4

The recently discovered hydrolytic kinetic resolution (HKR) using (salen)Co catalyst 2 presents a highly attractive method for accessing terminal epoxides in high enantiomeric purity. The HKR uses water as the only reagent, no solvent, and low loadings of a readily available and recyclable catalyst. In principle, kinetic resolution strategies are especially viable when the racemic starting material is inexpensive and readily available, and when the enantiopure material is relatively difficult to access. In the case of 1, the latter criterion is clearly met, but racemic 1 is not easily obtained from commercial sources. We have evaluated several approaches to 1, including racemic synthesis, preparation in moderate enantiomeric excess via highly-practical epoxidation with NaOCl and the commercial catalyst 3, and low temperature asymmetric epoxidation with m-CPBA and catalyst 4 under conditions devised to afford optimal enantioselectivity. Herein we report the successful application of these different epoxidation strategies in connection with the HKR for the synthesis of enantiopure 1.

Given the substantially lower cost of 3-chlorobenzaldehyde compared with 3-chlorostyrene, we chose to carry out the synthesis of racemic 1 by means of sulfur ylide addition to the aldehyde rather than epoxidation of the alkene.

Enantiomerically enriched epoxide was accessed from 3-chlorostyrene using 3 different sets of epoxidation conditions. As noted previously, the attainment of high enantioselectivity in the epoxidation of terminal styrene derivatives with (salen)Mn catalysts and related monooxygenase mimics requires both high enantiofacial selectivity in the first C—O bond-forming step and high diastereoselectivity in the second, ring-closure step. Both selectivity factors improve at lower temperature, and as a result enantioselectivities in epoxidations of these substrates display a strong temperature dependence. Epoxidation of 3-chlorostyrene under standard NaOCl conditions using the commercial catalyst 3 proceeded in only 32% ee but very good yield. Enantioselecitivity was improved slightly by carrying out the reaction at −18° C. (36% ee), but lower temperatures were not accessible with this aqueous oxidant. Epoxidation employing the recently-developed homogenous low temperature protocol (m-CPBA/N-methylmorpholine N-oxide (NMO)/catalyst 4) afforded epoxide 1 in excellent yield and 81% ee.

The HKR of 1 was carried out using epoxide prepared by the four different methods outlined above, with the amount of water in the HKR adjusted to correspond to 1.1 equivalents relative to the minor epoxide enantiomer (Table 1). Reactions on 1 g (6.9 mmol) of epoxide were complete within 2 days using 0.7 mol % (R,R)-2, and afforded enantiopure 1 in nearly quantitative yield. Entries 1 and 3 were also carried out on a 6 g (38.9 mmol) scale under the same conditions with consistent results. After the resolution was complete, epoxide was isolated by partitioning the products between pentane and water. The pentane phase contained epoxide and catalyst while the diol remained in the aqueous layer. Phase separation and solvent removal followed by distillation of each product afforded both enantiomerically enriched epoxide (99% ee, R) and diol (up to 91% ee, S). In all cases, an excellent correlation can be seen between overall yields of enantiopure 1 and the theoretical yields obtainable based on the ee of the starting material. While (R)-1 is the desired epoxide in most applications, the epoxidation/HKR sequence allows access to either enantiomer of 1 by simply switching the enantiomers of catalyst.

TABLE 1

HKR of 3-chlorostyrene oxide with 0.7 mol % (R,R)-2.

| | Starting Epoxide Ee (%) | HKR Conditions | HKR Epoxide | | HKR Diol | |
|---|---|---|---|---|---|---|
| Entry | (R) | H₂O (equiv) | Ee (%) | Yield (%)[a] | Ee (%) | Yield (%)[a] |
| 1 | 0 | 0.55 | 99 | 45 | 91 | 45 |
| 2 | 32 | 0.38 | 99 | 61 | 88 | 31 |
| 3 | 36 | 0.35 | 99 | 64 | 87 | 30 |
| 4 | 81 | 0.11 | 99 | 87 | 67 | 8 |

[a]Yield based on starting epoxide.

The determination of which of the above-described methods is most practical for the preparation of enantiopure 1 will clearly depend on the reaction scale and starting material costs. If 3-chlorobenzaldehyde is the most viable starting material, then a racemic epoxidation/HKR sequence is probably the most attractive alternative. If 3-chlorostyrene is employed as the starting material, epoxidation with NaOCl and catalyst 3 is competitive on a practical level with the best racemic methods such as peracid epoxidation, and the catalytic method affords a non-trivial overall yield advantage (61% yield of enantiopure 1 for the two step sequence from the alkene using the −18° C. epoxidation conditions). Low temperature epoxidation with the more exotic catalyst 4 is clearly less attractive for large scale applications, but it affords the highest overall yield (75%) from the corresponding olefin and thus might prove useful for very precious substrates.

Materials

3-Chlorostyrene, 4-phenylpyridine N-oxide (4-PPNO), and (R)-(+)-3-chlorostyrene oxide were obtained from Aldrich and used as received. 3-Chlorobenzaldehyde was purchased from Avocado and also used as received. The complex 3 is available from a variety of commercial sources or it can be conveniently prepared. The (salen)Co complex 2 can be made from commercially available ligand as described in the literature, or it is available commercially from ChiRex Ltd. (Dudley, U K). Complex 4 was synthesized as described below.

Methods

Flash chromatography was performed using packed glass columns of EM silica gel 60 (230–400 mesh). Gas chromatography analyses were performed on a Hewlett Packard 5890 Series II instrument equipped with an FID detector using a Hewlett Packard 30 m×0.32 mm i.d. HP-5 capillary column. High performance liquid chromatography was used for the enantiomeric excess analyses of the epoxide and diol. Whelk-O (0.25% isopropyl alcohol in hexane, 1.0 mL/min, λ=220 nm) was used for determination of enantiomeric excess for 3-chlorostyrene oxide. Chiralcel OD (3% isopropyl alcohol/hex, 1 mL/min, λ=220 nm) was used for ee determination of 1-(3-chlorophenyl)-ethane-1,2-diol. $^1$H NMR and $^{13}$C NMR spectra were recorded on a Bruker AM-400 spectrometer. Chemical shifts are reported downfield from tetramethylsilane with the solvent resonance as the internal standard (deuterochloroform, δ 7.26 and 77.06 ppm respectively). Infrared spectra were recorded on a Mattson Galaxy FTIR 3000 spectrometer. The optical rotations was measured on a Jasco DIP 370 digital polarimeter. Mass spectra were performed by the Harvard University Mass Spectrometry Laboratory on a Jeol AX-505 or SX-102 high resolution magnetic sector mass spectrometers.
Chloro-(R,R)-[[2,2'-[(1,2-diphenyl-1,2-ethanediyl)bis(nitrilo-methylidyne)]-bis[4-triisopropylsiloxy-6-(1,1-dimethylethyl)phenolato]]-N,N'O,O']manganese(III) 4

To a solution of diphenylethylenediamine (0.244 g, 1.15 mmol) in 90 mL of EtOH was added 3-t-butyl-5-triisopropylsilyloxysalicylaldehyde (0.800 g, 2.30 mmol). The resulting yellow solution was heated to reflux for 25 min before the addition of a solution of Mn(OAc)$_2$·4H$_2$O (0.564 g, 2.30 mmol) in 5 mL H$_2$O. The resulting brown solution was heated to reflux for 30 min, after which air was bubbled through the solution via a needle for an additional 30 min. Brine (5 mL) was added, and the mixture was further heated at reflux for 30 min before being cooled to ambient temperature. The solvent volume was reduced to ca. 15 mL under vacuum, and CH$_2$Cl$_2$ (100 mL) and water (100 mL) were added. The organic phase was separated, washed with brine (100 mL), and dried over Na$_2$SO$_4$. After solvent removal, the residue was purified by chromatography (SiO$_2$, 5% EtOH/CH$_2$Cl$_2$) to afford 0.854 g of product (77% yield), mp 280–280.8° C. IR (CH$_2$Cl$_2$) 2947, 2868, 1600, 1535, 1464, 1409, 1343, 1230, 1041, 1010, 963, 882, 869 cm$^{-1}$; HRMS (FAB) m/z: calc'd (C$_{54}$H$_{78}$ClMnN$_2$O$_4$Si$_2$) 929.4881 ([M−Cl]$^+$), found 929.4914.

Racemic 1

A) Synthesis of trimethysulfonium hydrogen sulfate: To dimethyl sulfate (10.0 mL, 1.05×10$^{-1}$ mol) at 0° C. was added dimethyl sulfide (10.4 mL, 1.42×10$^{-1}$ mol). After rapidly stirring at 0° C. for 30 minutes, the reaction was slowly warmed to room temperature yielding a crystalline solid, trimethylsulfonium methyl sulfate. After 3 hours, distilled water (20 mL) was added to form a clear solution of trimethylsulfonium sulfate.

B) Synthesis of (±)-1: The aqueous solution of trimethylsulfonium sulfate (20 mL, 1.05×10$^{-1}$ mol) was added slowly to a two-phase mixture of 50% NaOH (100 mL), 3-chlorobenzaldehyde (7.03 g, 5.00×10$^{-2}$ mol), tetrabutylammonium bromide (0.126 g, 3.91×10$^{-4}$ mol), and CH$_2$Cl$_2$ (132 mL). The reaction was heated at 50° C. for 13 hours and then cooled to room temperature. The reaction was diluted carefully with brine (250 mL) and diethyl ether (350 mL), and then filtered to remove solids. The aqueous layer was extracted with diethyl ether (3×350 mL), and the combined organic layers were washed with brine (200 mL) and dried over Na$_2$SO$_4$, filtered, and concentrated in vacuo to afford a pale yellow liquid. Bulb-to-bulb distillation (70° C., 0.6 mm Hg) from CaH$_2$ afforded 1 (7.12 g, 92%) as a colorless liquid. $^1$H NMR (CDCl$_3$) δ 7.27 (m, 3H), 7.17 (m, 1H), 3.83 (dd, J=2.5, 4.1 Hz, 1H), 3.15 (dd, J=4.1, 5.5 Hz, 1H), 2.76 (dd, J=2.5, 5.5 Hz, 1H); $^{13}$C NMR (100 MHz, CDCl$_3$) δ 139.9, 134.7, 129.9, 128.4, 125.6, 123.8, 51.8, 51.3; IR (thin film, cm$^{-1}$) 3057, 2994, 2920, 1603, 1576, 1080; CIHRMS calcd for C$_8$H$_7$ClO (M+NH$_4$)$^+$=172.0529, found 172.0527.

(R)-1 (32% ee)

A 2-necked round-bottom flask equipped with a water-cooled overhead stirrer was charged with 3-chlorostyrene (5.01 g, 3.61×10$^{-2}$ mol), CH$_2$Cl$_2$ (45 mL), (R,R)-3 (0.578 g, 9.10×10$^{-4}$ mol), and 4-PPNO (0.924 g, 5.40×10$^{-3}$ mol). The solution was cooled to 0° C., and precooled buffered bleach (0.6 M, 75 mL, 4.50×10$^{-2}$ mol, Clorox®, buffered to pH=11.3 with 0.05 M Na$_2$HPO$_4$ and 1M NaOH) was added. The two phase system was stirred vigorously, and the course of the reaction was monitored by GC. Upon complete consumption of starting olefin (<6 h), the reaction mixture was filtered through a plug of Celite on a coarse glass frit and washed with CH$_2$Cl$_2$ (75 mL). The organic layer of the filtrate was washed with distilled water (2×25 mL), and the aqueous layers were extracted with CH$_2$Cl$_2$ (2×25 mL). The combined organic layers were dried over Na$_2$SO$_4$ and concentrated in vacuo. Removal of the catalyst was effected by elution through a pad of SiO$_2$ (30 g) using pentane and CH$_2$Cl$_2$ (1:1). The eluent was concentrated in vacuo, and subsequent bulb-to-bulb distillation (70° C., 0.6 mm Hg) from CaH$_2$ afforded (R)-3-chlorostyrene oxide (5.15 g, 92%) as a pale yellow liquid in 32% ee.

(R)-1 (36% ee)

A 2-necked round-bottom flask equipped with an overhead stirrer was charged with 3-chlorostyrene (4.00 g, 2.89×10$^{-2}$ mol), CH$_2$Cl$_2$ (35 mL), (R,R)-3 (0.361 g, 5.68×10$^{-4}$ mol), 4-PPNO (0.724 g, 4.23×10$^{-3}$ mol), and 4.00 g ground NaCl. The solution was cooled to −18° C. while stirring vigorously and precooled 13% bleach (19.5 mL, Acros) was added down the side of the flask to allow for further cooling. The course of the reaction was monitored by GC. Upon complete consumption of starting olefin (<27 h), the reaction mixture was filtered through a plug of Celite using CH$_2$Cl$_2$ as the eluent, and the filtrate was treated as described above to afford (R)-3-chlorostyrene oxide (4.24 g, 95%) as a colorless liquid in 36% ee.

(R)-1 (81% ee)

A round-bottom flask equipped with a overhead stirrer was charged with 3-chlorostyrene (1.00 g, 7.22×10$^{-3}$ mol), CH$_2$Cl$_2$ (78 mL), (R,R)-4 (0.349 g, 3.61×10$^{-4}$ mol), and NMO (4.22 g, 3.62×10$^{-2}$ mol). The solution was cooled to −78° C. before solid m-CPBA (2.51 g, 1.46×10$^{-2}$ mol) was added in portions over 1.5 minutes. The reaction was monitored by GC. Upon completion (3 h), the reaction was quenched by the addition of a solution of dimethyl sulfide (6 mL) in CH$_2$Cl$_2$ (25 mL) precooled to −78° C. The solution was stirred for an additional 10 minutes at −78° C. before removal of the cold bath and addition of 2N NaOH (20 mL) and CH$_2$Cl$_2$ (20 mL). The phases were separated and the aqueous layer was washed with CH$_2$Cl$_2$ (2×50 mL).The combined organic layers were dried over Na$_2$SO$_4$, filtered and concentrated in vacuo. Removal of the catalyst was effected by elution through a pad of SiO$_2$ (10 g) using pentane and CH$_2$Cl$_2$ (1:1). The eluent was concentrated in vacuo, and subsequent bulb-to-bulb distillation from CaH$_2$ afforded (R)-3-chlorostyrene oxide (0.963 g, 86%) as a colorless liquid in 81% ee.

Hydrolytic Kinetic Resolution of (R)-1

To (R)-1 (6.00 g, 3.88×10$^{-2}$ mol, 36% ee) and (R,R)-2 (0.192 g, 2.82×10$^{-4}$ mol) was added water (245 mL, 1.36×10$^{-2}$ mol, 0.35 eq) and the mixture was stirred at room temperature for 48 h. Pentane (2×100 mL) was added, and the resulting mixture was stirred vigorously for 5 minutes, then the solution was separated from the solid residue by decantation. The residue was stirred with a 1:1 pentane-water mixture (2×100 mL) and filtered through glass wool. The layers were separated and the aqueous layer was washed with pentane (3×100 mL) until no color remained. All the pentane layers were combined and dried over Na$_2$SO$_4$, filtered, and concentrated in vacuo. Bulb-to-bulb distillation from CaH$_2$ afforded (R)-1 (3.78 g, 63%, clear, pale yellow liquid) in 99% ee. The aqueous layer was also concentrated and after bulb-to-bulb distillation afforded (1S)-1-(3-chlorophenyl)-ethane-1,2-diol (1.83 g, 27%) in 87% ee. Diol: $^1$H NMR (CDCl$_3$) δ 7.34 (m, 1H), 7.26 (m, 2H), 7.18 (m, 1H), 4.74 (dd, J=3.3, 8.3 Hz, 1H), 3.70 (dd, J=3.3, 11.5 Hz, 1H), 3.57 (dd, J=8.3, 11.5 Hz, 1H), 3.29 (bs, 2H); $^{13}$C NMR (CDCl$_3$) δ 142.5, 134.4, 129.8, 128.0, 126.2, 124.1, 74.0, 67.8; IR (thin film, cm$^{-1}$) 3376, 2928, 1431, 1196, 1076, 1030; CIHRMS calcd for C$_8$H$_9$ClO$_2$ (M+NH4)$^+$=190.0635, found 190.0637. $[\alpha]_D^{26}$=+21.2° (c=2.9, EtOH); lit $[\alpha]_D$=+24.05° (c=1.24, EtOH, 95% ee material).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A kinetic resolution process, comprising the step of reacting a silyl azide and a mixture of stereoisomers of a chiral cyclic substrate in the presence of a non-racemic chiral catalyst to produce by kinetic resolution a stereoisomerically enriched cyclic substrate or a stereoisomerically enriched azide-substituted product or both, wherein said chiral cyclic substrate comprises a carbocycle or heterocycle having a reactive center susceptible to nucleophilic attack by said silyl azide, and said non-racemic chiral catalyst comprises an asymmetric tetradentate ligand complexed with a metal atom, which complex has a rectangular planar or rectangular pyramidal geometry.

2. The process of claim 1, wherein said silyl azide is a trialkylsilyl azide.

3. The process of claim 1, wherein said silyl azide is trimethylsilyl azide.

4. The process of claim 1, wherein the metal atom is a transition metal from Groups 3–12 or from the lanthanide series.

5. The process of claim 1, wherein the metal atom is selected from the group consisting of Co, Rh, and Ir.

6. The process of claim 1, wherein the metal atom is Co.

7. The process of claim 1, wherein the non-racemic chiral catalyst is selected from the group consisting of chiral crown ethers complexed with a transition metal atom; the chiral catalyst represented by 102,

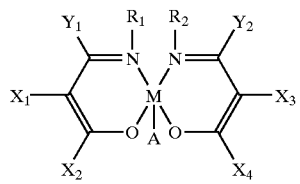

102 in which the substituents R$_1$, R$_2$, Y$_1$, Y$_2$, X$_1$, X$_2$, X$_3$ and X$_4$ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, or any two or more of the substituents taken together form a carbocycle or heterocycle having from 4 to 8 atoms in the ring structure, which ring structure may be a fused ring, as in the case of, for example, X$_1$ and X$_2$ forming a ring, or which ring may be a bridging ring, as in the case of R$_1$ and R$_2$, X$_2$ and X$_4$, or Y$_1$ and X$_2$ representing different ends of a single substituent, with the proviso that at least one of R$_1$, Y$_1$, X$_1$ and X$_2$ is covalently bonded to at least one of R$_2$, Y$_2$, X$_3$ and X$_4$ to provide the β-iminocarbonyls as a tetradentate ligand;

R$_7$ represents an aryl, a cycloalkyl, a cycloalkenyl, a heterocycle, or a polycycle;

m is zero or an integer in the range of 1 to 8;

M represents a transition metal;

A represents a counterion or a nucleophile; and the catalyst is asymmetric;

the chiral catalyst represented by 108,

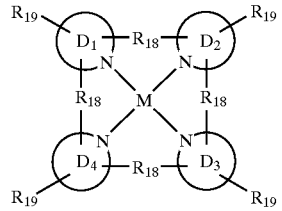

108 in which

D$_1$, D$_2$, D$_3$ and D$_4$ each represent heterocycles, such as pyrrole, pyrrolidine, pyridine, piperidine, imidazole, pyrazine, or the like;

each R$_{18}$ occurring in the structure represents a bridging substituent which links adjacent heterocycles, and preferably contains at least one stereogenic center of the ligand. For example, each R$_{18}$, represents an alkyl, an alkenyl, an alkynyl, or —R$_{15}$—R$_{16}$—R$_{17}$—, wherein R$_{15}$ and R$_{17}$ each independently are absent or represent an alkyl, an alkenyl, or an alkynyl, and R$_{16}$ is absent or represents an amine, an imine, an amide, a phosphonate, a phosphine, a carbonyl, a carboxyl, a silyl, an oxygen, a sulfonyl, a sulfur, a selenium, or an ester;

each R$_{19}$, independently, is absent or represents one or more substituents of the heterocycle to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, and —(CH$_2$)$_m$—R$_7$;

or any two or more of the R$_{18}$ and R$_{19}$ substituents are covalently linked to form a bridge substitution;

R$_7$ represents an aryl, a cycloalkyl, a cycloalkenyl, a heterocycle or a polycycle;

m is zero or an integer in the range of 1 to 8;

M represents a transition metal; and the catalyst is asymmetric;

the chiral catalyst represented by 112,

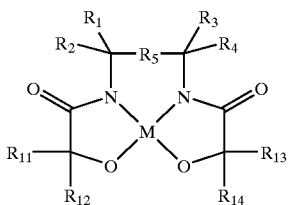

in which
each of the substituents $R_1$, $R_2$, $R_3$, $R_4$, $R_5$, $R_{11}$, $R_{12}$, $R_{13}$ and $R_{14}$, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle having at least 4 atoms in the ring structure;

$R_7$ represents an aryl, a cycloalkyl, a cycloalkenyl, a heterocycle or a polycycle;

m is zero or an integer in the range of 1 to 8; and

M represents a transition metal;

if $R_5$ is absent, at least one of $R_1$ and $R_2$ is covalently bonded to at least one of $R_3$ and $R_4$; and the catalyst is asymmetric;

the chiral catalyst represented by 114 and a complexed transition metal atom,

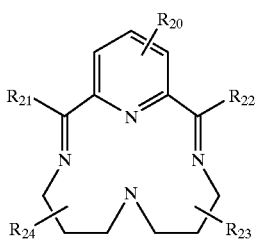

wherein
$R_{21}$ and $R_{22}$ each represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{20}$ is absent or represents one or more substituents of the pyridine to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{23}$ and $R_{24}$ each independently are absent or represent one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ and $R_{24}$ substituents are covalently linked to form a bridging substituent;

$R_7$ represents an aryl, a cycloalkyl, a cycloalkenyl, a heterocycle or a polycycle; and m is zero or an integer in the range of 1 to 8; and the ligand is asymmetric; and the chiral catalyst represented by 116 and a complexed transition metal atom,

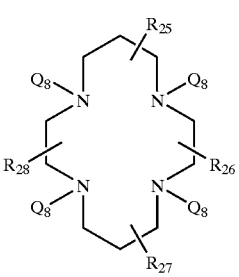

in which
each of the substituents $Q_8$ independently, are absent or represent hydrogen or a lower alkyl;

each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$; or any two or more of the substituents taken together form a bridging substituent;

$R_7$ represents an aryl, a cycloalkyl, a cycloalkenyl, a heterocycle, or a polycycle;

m is zero or an integer in the range of 1 to 8; and the ligand is asymmetric.

8. The process of claim 1, wherein the non-racemic chiral catalyst is represented by structure A or its enantiomer:

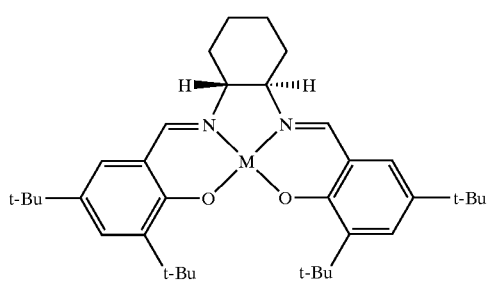

wherein
M represents Co or Co($O_2$CR); and
R represents alkyl or aryl.

9. The process of claim 8, wherein said silyl azide is a trialkylsilyl azide.

10. The process of claim 8, wherein said silyl azide is trimethylsilyl azide.

11. The process of claim 1, wherein the tetradentate ligand has at least one Schiff base that complexes with the metal atom.

12. The process of claim 1, wherein the chiral catalyst has a molecular weight of less than 10,000 a.m.u.

13. The process of claim 1, wherein the chiral cyclic substrate is represented by the general formula 118:

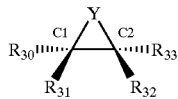

in which
Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y.

14. The process of claim 13, wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —($CH_2$)$_m$—$R_7$;

or any two or more of the substituents $R_{30}$, $R_{31}$, $R_{32}$, and $R_{33}$ taken together form a carbocylic or heterocyclic ring having from 4 to 8 atoms in the ring structure; $R_7$ represents an aryl, a cycloalkyl, a cycloalkenyl, a heterocycle or a polycycle; and m is zero or an integer in the range of 1 to 8.

15. The process of claim 1, wherein the chiral cyclic substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

16. The process of claim 1, wherein the chiral cyclic substrate is an epoxide.

17. The process of claim 1, wherein the chiral cyclic substrate is a terminal epoxide.

18. The process of claim 1, wherein the non-racemic chiral catalyst is immobilized on an insoluble matrix.

19. The process of claim 1, wherein the chiral cyclic substrate is immobilized on an insoluble matrix.

20. A kinetic resolution process, comprising the step of reacting a silyl azide and a mixture of stereoisomers of a chiral cyclic substrate in the presence of a non-racemic chiral catalyst to produce by kinetic resolution a stereoisomerically enriched cyclic substrate or a stereoisomerically enriched azide-substituted product or both, wherein said chiral cyclic substrate comprises a carbocycle or heterocycle having a reactive center susceptible to nucleophilic attack by said silyl azide, and said non-racemic chiral catalyst comprises an asymmetric tridentate ligand complexed with a metal atom, which complex has a trigonal planar or trigonal pyramidal geometry.

21. The process of claim 20, wherein said silyl azide is a trialkylsilyl azide.

22. The process of claim 20, wherein said silyl azide is trimethylsilyl azide.

23. The process of claim 20, wherein the metal atom is a transition metal from Groups 3–12 or from the lanthanide series.

24. The process of claim 20, wherein the metal atom is selected from the group consisting of Co, Rh, and Ir.

25. The process of claim 20, wherein the metal atom is Co.

26. The process of claim 20, wherein the tridentate ligand has at least one Schiff base that complexes with the metal atom.

27. The process of claim 20, wherein the non-racemic chiral catalyst has a molecular weight of less than 10,000 a.m.u.

28. The process of claim 20, wherein the chiral cyclic substrate is represented by the general formula:

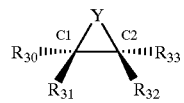

in which
Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y.

29. The process of claim 28, wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —($CH_2$)$_m$—$R_7$;

or any two or more of the substituents $R_{30}$, $R_{31}$, $R_{32}$, and $R_{33}$ taken together form a carbocyclic or heterocyclic ring having from 4 to 8 atoms in the ring structure;

$R_7$ represents an aryl, a cycloalkyl, a cycloalkenyl, a heterocycle or a polycycle; and m is zero or an integer in the range of 1 to 8.

30. The process of claim 20, wherein the chiral cyclic substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones, and sultones.

31. The process of claim 20, wherein the chiral cyclic substrate is an epoxide.

32. The process of claim 20, wherein the chiral cyclic substrate is a terminal epoxide.

33. The process of claim 20, wherein the non-racemic chiral catalyst is immobilized on an insoluble matrix.

34. The process of claim 20, wherein the chiral cyclic substrate is immobilized on an insoluble matrix.

35. The process of any of claims 1–34, wherein said chiral cyclic substrate is racemic.

* * * * *

UNITED STATES PATENT AND TRADEMARK OFFICE
CERTIFICATE OF CORRECTION

PATENT NO.       : 6,841,667 B2
APPLICATION NO.  : 10/615501
DATED            : January 11, 2005
INVENTOR(S)      : Jacobsen et al.

It is certified that error appears in the above-identified patent and that said Letters Patent is hereby corrected as shown below:

Column 1, line 18, remove "in part".

Column 1, line 19, insert -- (grant number GM43214) -- after "Health".

Signed and Sealed this

Fourteenth Day of April, 2009

JOHN DOLL
*Acting Director of the United States Patent and Trademark Office*